(12) United States Patent
Novick et al.

(10) Patent No.: US 7,696,154 B2
(45) Date of Patent: *Apr. 13, 2010

(54) METHODS FOR TREATING INTERLEUKIN-18 MEDIATED DISORDERS WITH INTERLEUKIN-18 BINDING PROTEINS

(75) Inventors: Daniela Novick, Rehovot (IL); Charles Dinarello, Boulder, CO (US); Menachem Rubinstein, Givat Shmuel (IL); Soo Hyun Kim, Denver, CO (US); Yolande Chvatchko, Confignon (CH); Christine Plater-Zyberk, Geneva (CH)

(73) Assignee: Yeda Research and Development Company Ltd., Rehovot (IL)

( * ) Notice: Subject to any disclaimer, the term of this patent is extended or adjusted under 35 U.S.C. 154(b) by 105 days.

This patent is subject to a terminal disclaimer.

(21) Appl. No.: 11/724,737

(22) Filed: Mar. 15, 2007

(65) Prior Publication Data

US 2007/0173439 A1 Jul. 26, 2007

Related U.S. Application Data

(60) Division of application No. 09/790,338, filed on Feb. 21, 2001, now Pat. No. 7,220,717, which is a continuation-in-part of application No. 09/485,632, filed on Oct. 12, 2000, now Pat. No. 6,605,280.

(30) Foreign Application Priority Data

| Aug. 14, 1997 | (IL) | 121554 |
| Aug. 27, 1997 | (IL) | 121639 |
| Sep. 29, 1997 | (IL) | 121860 |
| Nov. 6, 1997 | (IL) | 122134 |
| Jul. 22, 1998 | (IL) | 125463 |
| Feb. 21, 2000 | (EP) | 00103590 |
| Feb. 21, 2000 | (EP) | 00103597 |
| Nov. 23, 2000 | (EP) | 00125633 |

(51) Int. Cl.
*A61K 38/00* (2006.01)

(52) U.S. Cl. .................. 514/2; 530/350; 530/351; 530/387.3; 435/69.7

(58) Field of Classification Search ............... None
See application file for complete search history.

(56) References Cited

U.S. PATENT DOCUMENTS

| 5,776,731 A | 7/1998 | Parnet et al. |
| 5,932,549 A | 8/1999 | Allen et al. |
| 5,985,863 A | 11/1999 | Su et al. |
| 6,087,116 A | 7/2000 | Torigoe et al. |

FOREIGN PATENT DOCUMENTS

| EP | 0850952 | 7/1998 |
| EP | 0864585 | 9/1998 |
| EP | 0974600 | 1/2000 |
| WO | WO 98/22137 | 5/1998 |
| WO | WO 98/24804 | 6/1998 |
| WO | WO 98/41232 | 9/1998 |
| WO | WO 99/06549 | 2/1999 |
| WO | WO 99/06553 | 2/1999 |
| WO | WO 99/55377 | 11/1999 |
| WO | WO 00/12555 | 3/2000 |
| WO | WO 00/56771 | 9/2000 |
| WO | WO 01/03719 | 1/2001 |
| WO | WO 01/19373 | 3/2001 |

OTHER PUBLICATIONS

Afford, et al. (1998). *Journal of Pathology* 186: 82-89.
Baroni, et al. (1999). *Liver* 19: 212-219.
Bird, et al. (1990). *Annals of Internal Medicine* 112: 917-920.
Camoglio, et al. (2000). *Eur. J. Immunol.* 30: 1486-1495.
Dayer, et al. (1999). *The Journal of Clinical Investigation* 104: 1337-1339.
Desreumaux, et al. (1997). *Gastroenterology* 113: 118-126.
DiDonato, et al. (1997). *Nature* 388: 548-554.
Elliott, et al. (1994). *The Lancet* 344: 1125-1127.
Engelmann, et al. (1989). *The Journal of Biological Chemistry* 264: 11974-11980.
Fiore, et al. (1999). *Microbios* 97:29-38.
Galle, et al. (1995). *J. Exp. Med.* 182: 1123-1230.
Grantham, et al. (1974). *Science* 185: 862-864.
Grove, et al. (1997). *Hepatology* 26:143-146.
Harada, et al. (1997). *Hepatology* 25:791-796.
Hill, et al. (1992). *J. Lab. Clin. Med.* 119: 547-552.
Hill, et al. (1993) *Hepatology* 18: 576-580.
Hiramatsu, et al. (1994). *Hepatology* 19: 1354-1359.
Huang, et al. (1996). *Journal of Hepatology* 24: 337-384.
Iio, et al. (1998). *Journal of Hepatology* 29: 517-523.
Izaki (1978). *Jpn. J. Bacteriol* 33: 729-742.
Kashiwamura, et al. (1998) Nippon Rinsho 7: 1798-1806.
Kim, et al. (2000). *Proc. Natl. Acad. Sci.* 97: 1190-1195.
Knight, et al. (1993). *Molecular Immunology* 30: 1443-1453.
Lee, et al. (1999). *J. Korean Med Sci* 14:175-181.
Lukkari, et al. (1999). *Alcohol & Alcoholism* 34:311-319.
Luo, et al. (1997). *Journal of Viral Hepatitis* 4: 303-307.
Martinez, et al. (1992). *Alcohol* 9: 455-458.
McClain, et al. (1998). *Alcoholism: Clinical and Experimental Research* 22 (5 Suppl.): 248S-252S.
McClain and Cohen (1989). *Hepatology* 9: 349-351.
Monteleone, et al. (1999). *The Journal of Immunology* 163: 143-147.
Nanji, et al. (1999). *Hepatology* 30: 934-943.

(Continued)

*Primary Examiner*—Dong Jiang
(74) *Attorney, Agent, or Firm*—Mintz Levin, Cohn, Ferris, Glovsky and Popeo P.C.; Ivor R. Elrifi; Cynthia Kozakiewicz

(57) ABSTRACT

Interleukin-18 binding proteins which are capable of binding IL-18 and of modulating and/or blocking IL-18 activity are provided. Methods for the isolation and recombinant production, DNAs encoding them. DNA vectors expressing them, vectors useful for their expression in humans and other mammals, antibodies against them are also provided. Therapeutic uses of IL-18 binding proteins and further inhibitors of IL-18 are also provided according to the invention.

15 Claims, 16 Drawing Sheets

OTHER PUBLICATIONS

Nishimura and Ohta (1999). *The Journal of Immunology* 162: 6503-6509.
Ohlinger, et al. (1993). *Virchows Archiv A Pathol Anat* (1993). 423: 169-176.
Okamoto, et al. (1998). *Jpn. J. Pharmacol*.78: 233-235.
Okazaki, et al. (1996). *Digestive Diseases and Sciences* 41: 2453-2458.
Okamoto, et al. (1999). *International Journal of Molecular Medicine* 3: 517-520.
Plater-Zyberk and Bonnefoy (1995). *Nature Medicine* 1: 781-785.
Pizarro, et al. (1999). *The Journal of Immunology* 162: 6829-6835.
Reimund, et al. (1996). *Journa of Clinical Immunology* 16: 144-150.
Saha, et al. (1999). *Arthritis & Rheumatism* 42 1577-1587.
Sheron, et al. (1991). *Clin exp. Immunol* 84: 449-453.
Su, et al. (1998). *American Journal of Pathology* 152: 841-849.
Taieb, et al. (1998). *The Lancet* 351: 1930-1931.
Triantaphyllopoulos, et al. (1999). *Arthritis & Rheumatism* 42: 90-99.
Tucci, et al. (1992). *The Journal of Immunology* 148: 2778-2784.
Williams, et al. (1994). *Proc. Natl. Acad. Sci. USA* 91: 2762-2766.
Yoshimoto, et al. (1998). *The Journal of Immunology* 161: 3400-3407.
Adams, M.D. et al., EMBL Database Entry HSZZ16951, GenBank accession No. AA311795 (Apr. 18, 1997).
Adams, M.D. et al., EMBL Database Entry HZZ03012, GenBank accession No. g1950205 (Apr. 18, 1997).
Aizawa Y, Akita K, Taniai M, et al: Cloning and expression of interleukin-18 binding protein FEBS Lett. 445:338-342, 1999.
Akira S: the role of Il-18 in innate immunity. Curr.Opin. Immunol. 12:59-63, 200.
Akita K, Ohtsuki T. Nukada Y, et al: Involvement of caspase-1 and caspase-3 in the production and processing of mature khuman interleukin 18 in monocytic THP.1 cells. J. Biol. Chem. 272:26595-26603, 1997.
Anderson, D.M., et al., *a homologue of the TNF receptor and its ligand enhance T-cell growth and dendritic-cell function*. Nature, 1997. 390(6656): p. 175-179.
Bollon, D..P., et al. (1980) *J. Clin. Hematol. Oncol*. 10:39-48.
Botstein, D., et al. (1982) Miami Wint. Symp. 19:265-274.
Broach, J.R., in "The Molecular Biology of the Yeast Saccharomyces: Life Cycle and Inheritance", Cold Spring Harbor Laboratory, Cold Sprong Harbor, NY, pp. 445-470 (1981).
Broach, J.R., (1982) *Cell* 28:203-204.
Byrn R.A. et al, 1990, *Nature* (London) 344:667-670.
Car, B.D., V.M. Eng. B. Schnyder, L. Ozmen, S. Huang, P. Gallay, D. Heumann, M. Aguet, and B. Ryffel. 1994. Interferon gamma receptor deficient mice are resistant to endotoxic shock. *J. Exp. Med.* 179:1437-44 issn:0022-1007.
Conti, B., J. W. Jahng, C. Tinti, J.H. Son, and T.H. Joh. 1997. Induction of interferon-gamma inducing factor in the adrenal cortex. *J. Biol. Chem.* 272:2035-2037.
Dao, T, Mehal WZ, Crispe 1N: IL-18 augments perforin-dependent cytotoxicity of liver NK-T cells. J. Immunol. 161:2217-2222, 1998.
Dao, T., K. Ohashi, T. Kayano, M. Kurimoto, and H. Okamura. 1996. Interferon-gamma inducing factor, a novel cytokine, enhances Fas ligand-mediated cytotoxicity of murine T helper 1 cells. Cell-Immunol. 173:230-5 issn: 0008-8749.
Debets R, Timans JC, Churakowa T, et al: IL—18 Receptors, Their Role in Ligand Binding and Function: Anti-IL-1RAcPL Antibody, a Potent Antagonist of IL-18. J.Immunol. 165:4950-4956, 2000.
Dinarello CA, Novick D, Puren AJ, et al: Overview of interleukin-18: more than an interferon-gamma inducing factor. J.Leukoc.Biol. 63:658-664, 1998.
Dinarello CA:IL-18: A TH1-inducing, proinflammatory cytokine and new member of the IL-1 family. J.Allergy Clin.Immunol. 103:11-24, 1999.
Dinarello CA: Targeting interleukin 18 with interleukin 18 binding protein. Ann.Rheum.Dis 59 Suppl 1:117-120117-1202000.
EMBL Database Entry 0 00923, GenBank accession No. 0 00923 Jul. 26, 1993.
EMBL Database Entry 0 00919, GenBank accession No. 0 00919 Jan. 15, 1991.
Engelemann, H., D. Novick, and D. Wallach. 1990. Two tumor necrosis factor-binding proteins purified from human urine. Evidence for immunological cross-reactivity with cell surface tumor necrosis factor receptors. *J. Biol. Chem.* 265;1531-1536.
Fantuzzi, G., et al., *IL-18 regulation of IFN-g production and cell proliferation as revealed in interleukin-1b converting enzyme-deficient mice*. Blood, 1998. 91: p. 2118-2125.
Ghayur T, Banerjee S, Hugunin M, et al: Caspase-1 processes IFN-gamma-inducing factor and regulates LPS-induced IFN-gamma production. Nature 386:619-623, 1997.
Gillespie MT, Horwood NJ: Interleukin-18: perspectives on the newest interleukin. Cytokine.Growth Factor. Rev.9:109-116, 1998.
Gracie JA, FOrsey RJ, Chan WL, et al. A proinflammatory role for IL-18 in rheumatoid arthritis. J.Clin.Invest. 104:1393-1401, 1999.
Gryczan, T., "The Molecular Biology of the Bacilli", Academic Press, NY (1982), pp. 307-329).
Gu Y. Kuida K, Tsutsui H, et al: Activation of interferon-gamma inducing factor mediated by interleukin-1beta converting enzyme, Science 275:206-209, 1997.
Gutkind, J.S., et al., *A novel c-fgr exon utilized in Epstein-Barr virus-infected B lymphcytes buyt not in mormal monocytes*. Molec. Cell. Biol., 1991. 11: p. 1500-1507.
Heremans, H., J. Van Damme, C. Dillen, R. Dijkmans, and A. Billiau. 1990. Interferon gamma, a mediator of lethal lipopolysaccharide-induced Shwartzman-like shock reactions in mice. *J. Exp. Med.* 171: 1853-69 issn: 0022-1007.
Hillier, L. et al., EMBL Database Entry HSA10059, GenBank accession No. AA010059 Nov. 29, 1996.
Hochholzer P, Lipford GB, Wagner H, et al: Role of Interleukin-18 (IL-18) during Lethal Shock: Decreased Lipopolysaccharide Sensitivity but Normal Superantigen Reaction in IL-18 Deficient Mice. Infect.Immun. 68:3502-3508, 2000.
Holmes S. Abrahamson JA, Al-Mahdi N, et al: Characterization of the in vitro and in vivo activiity of monoclonal antibodies to human IL-18. Hybridoma 19:363-367, 2000.
Horwood NJ, Udagawa N, Elliott J., et al: Interleukin 18 inhibits osteoclast formation via T cell production of granulocyte macrophage colony-stimulating factor. J. Clin Invest. 101:595-603, 1998.
Hoshino K, Tsutsui H, Kawai T, et al: Cutting edge: generation of IL-18 receptor-deficient mice: evidence for IL-1 receptor-related protein as an essential IL-18 binding receptor. J.Immunol. 162:5041-5044, 1999.
Hyun KS, Reznikov LL, Stuyt RJ, et al: Functional reconstitution and regulation of IL-18 activity by the IL-18RP chain [in Process Citation]. J Immunol 166:148-154, 2001.
Hyun KS, Eisenstein M, et al.: Structural Requirements of SIx naturally Occurring Isoforms of the IL-18 Binding Protein to Inhibit IL-18. PNAS 97(3): 1190-1195.
John, J.F., et al. (1986) Rev. Infect. Dis. 8:693-704).
Kendall, K.J. et al. (1987) *J. Bacteriol*. 169:4177-4183).
Kobayashi K, Nakata N, Kai M, et al: Decreased expression of cytokines that induce type 1 helper T cell/interferon-gamma responses in genetically susceptible mice infected with *Mycobacterium avium*. Clin.Immunopathol. 85:112-116, 1997.
Kohno, K., J. Kataoka, T. Ohtsuki, Y. Suemoto, I. Okamoto, M. Usui, M. Ikeda and M. Kurimoto. 1997. IFN-gamma-inducing factor (IGIF) is a costimulatory factor on the activation of Th1 but not Th2 cells and exerts its effect independently of IL-12. *J. Immunol.* 158:1541-1550.
Kunikata T, Torigoe K, Ushio S, et al: Constitutive and induced IL-18 receptor expression by various peripheral blood cell subsets as determined by anti-hiL-18R monoclonal antibody. Cell Immunol. 189:135-143, 1998.
Lebel-Binay S, Berger A, Zinzindohoue F, et al: Interleukin-18: biological properties and clinical implications [Review]. European Cytokine Network 11:15-25, 2000.
Leung BP, McInnes IB, Esfandiari E, et al: Combined effects of IL-12 and IL-18 on the induction of collagen-induced arthritis. J.Immunol. 164:6495-6502, 2000.
Maliszewski, C.R., T.A. Sato, T. Vanden Bos, S. Waugh, S.K. Dower, J. Slack, M.P. Beckmann, and K. H. Grabstein. 1990. Cytokine receptors and B cell functions. 1. Recombinant soluble receptors specifically inhibit IL-1- and IL-4 induced B cell activities in vitro. *J. Immunol.* 144:3028-3033.

Maniatis, T., in "Cell Biology: A Comprehensive Treatise. vol. 3: Gene Expression". Academic Press. NY, pp. 563-608.

McInnes IB, Gracie JA, Leung BP, et al: Interleukin 18: a pleiotropic participant in chronic inflammation, Immunol.Today 21:312-315, 2000.

Micallef, M.J., T. Ohtsuki, K. Kohno, F. Tanabe, S. Ushio, M. Namba, T. Tanimoto, K. Torigoe, M. Fujii, M. Ikeda, S. Fukuda, and M. Kurimoto. 1996. Interferon-gamma-inducing factor enhances T helper 1 cytokine production by stimulated human T cells: synergism with interleukin-12 for interferon-gamma production *Eur-J-Immunol* 26:1647-51 issn: 0014-2980.

Mizushima, S. and Nagata, S. (1990) pEF-BOS, a powerful mammalian expression vector. *Nucleic Acid Res.* 18:5322-5328.

Muhl HG, Kampfer H, Bosmann, et al: Interferon-gamma mediates gene expression of IL-18 binding protein in nonleukocytic cells [in Process Citation]. Biochem.Biophys.Res.Commun. 267:960-963, 2000.

Muneta Y, kShimoji Y, Yokomizo Y, et al: Molecular cloning of porcine interleukin-1beta convering enzyme and differential gene expression of IL-1beta converting enzyme, IL-1beta, and IL-18 in porcine alveolar macrophages [in Process Citation]. J.Interferon. Cytokine.Res. 19:1289-1296, 1999.

Nakamura, K., H. Okamura, K. Nagata, T. Komatsu, and T. Tamura. 1993. Purification of a factor which provides a costimulatory signal for gamma interferon production. Infect-Immun 61:64-70 issn: 0019-9567.

Nakamura, K., H. Okamura, M. Wada, K. Nagata, and T. Tamura. 1989. Endotoxin-induced serum factor that stimulates gamma interferon production. Infect-Immun 57:590-5 issn: 0019-9567.

Nishida Y, Torigoe K, Aizawa Y, et al: Cloning and expression of a single-chain Fv fragment specific for kthe human interleukin 18 receptor. Hybridoma 17:577-580, 1998.

Novick D, Kim Sh, Fantuzzi G, et al: Interleukin-18 binding protein: a novel modulator of the Th1 cytokine response. Immunity. 10:127-136, 1999.

Novick, D., B. Cohen, and M. Rubinstein. 1994. The Human Interferon alpha/beta Receptor—Characterization and Melecular Cloning. *Cell* 77:391-400.

Novick, D., B. Cohen and M. Rubinstein. 1992. Soluble Interferon-alpha Receptor Molecules Are Present in Body Fluids. FEBS Lett 314:445-448.

Novick, D., H. Engelmann, D. Wallach, and M. Rubinstein. 1989. Soluble cytokine receptors are present in normal human urine. *J. Exp. Med.* 170:1409-1414.

Okumura, H., H. Tsutsui, T. Komatsu, M. Yutsudo, A. Hakura, T. Tanimoto, K. Torigoe, T. Okura, Y. Nukada, K. Hattori, K. Akita, M. Namba, F. Tanabe, K. Konishi, S. Kukuda, and M. Kurimoto. 1995. Cloning of a new cytokine that induces IFN-gamma production by T cells. *Nature* 378:88-91.

Olee T, Hashimoto S, Quach J, et al: IL-18 is produced by articular chondrocytes and induces proinflammatory and catabolic responses. J. Immunol. 162: 1096-1100, 1999.

Parnet et al., the Journal of Biological Chemistry, 271, 3967-3970 (1996).

Puren AJ. Fantuzzi G, Gu Y, et al: Interleukin-18 (IFNgamma-inducing factor)induces IL-8 and IL-1beta via TNFalpha production from non-CD14+ human blood mononuclear cells. J. Clin.Invest. 101:711-721, 1998.

Reznikov LL, Kim SH, Westcott JY, et al. IL-18 binding protein increases spontaneous and IL-1-induced prostaglandin production via inhibition of IFN-gamma. Proc.Natl.Acad.Sci.U.S.A.2000. 97:2174-2179, 2000.

Rothe, H., N. A. Jenkins, N. G. Copeland, and H. Kolb. 1997. Active stage of autoimmune diabetes is associated with the expression of a novel cytokine, IGIF, which is located near Idd2. *J-Clin-Invest.* 99:469-74 issn: 0021-9738.

Sakao Y, Takeda K, Tsutsui H, et al: IL-18 deficient mice are resistant to endotoxin-induced liver injury but highly susceptible to endotoxin shock [in Process Citation]. Int.Immunol. 11:471-480, 1999.

Sarvetnick N: IFN-gamma, IGIF, and IDDM [editorial]. J.Clin.Invest. 99:371-372, 1997.

Senkevich, T.G. et al., EMBL Database Entry U60315, GenBank accession No. AAC55182 Aug. 16, 1996.

Senkevich T.G. et al. EMBL Database Entry U60315, GenBank accession No. AAC55182 Aug. 16, 1996.

Sompayrac, L.H. and K. L. Danna, *Efficient infection of monkey cells with DNA of simian virus* 40. Proc. Nat'l. Acad. Sci. USA, 1981 78: p. 7575-7578.

Sparks, C.A., et al., *Assignment of the nuclear mitotic apparatus protein NuMa gene to human chromosome* 11q13. Genomics, 1993. 17: p. 222-224.

Takeda K, Tsutsui H, Toshimoto T, et al: Defective NK cell activity and Th1 response in IL-18-deficient mice. Immunity.8:383-390, 1998.

Tang, T.K. et al., EMBL Database Entry HSNUMAT3G, GenBank accession No. Z14229 Apr. 15, 1993.

Torigoe K, Ushio S, Okura T, et al: Purification and characterization of the human interleukin-18 receptor. J.Biol.Chem. 272-25737-25742, 1997 vol. 41.

Tsuji H, Mukaida N, Harada A, et al: Alleviation of lipopolysaccharide-incuded actue liver injury in Propionibacterium acnes-primed IFN-gamma-deficient mice by a concomitant reduction of TNF-alpha, IL-12, and IL-18 production. J.Immunol. 162:1049-1055, 1999.

Tsutsui H, Matsui K, Kawada N, et al: IL-18 accounts for both TNF-alpha-and Fas ligand- mediated hepatotoxic pathways in endotoxin-induced liver injury in mice. J.Immunol. 159:3961-3967, 1997.

Tsutsui H, Kayagaki N, Kuida K, et al: Caspase-1-independent, Fas/Fas ligand-mediated IL-18 secretion from macrophages causes acute liver injury in mice. Immunity. 11:359-367, 1999.

Tsutsui H, Matsui K, Okamura H, et al: Phathophysiological roles of interleukin-18 in inflammatory liver diseases [In Process Citation]. Immunol.Rev. 174:192-209:192-209, 2000.

Tsutsui, H., K. Nakanishi, K. Matsui, K. Higashino, H. Okamura, Y. Miyazawa, and K. Kaneda. 1996. IFN-gamma-inducing factor up-regulates Fas ligand-mediated cytotoxic activity of murine natural killer cell clones. *J. Immunol.* 157:3967-73 issn. 0022-1767.

Ushio, S., M. Namba, T. Okura, K. Hattori, Y. Nukada, K. Akita, F. Tanabe, K. Konishi, M. Micallef, M. Fujii, K. Torigoe, T. Tanimoto, S. Fukuda, M. Ikeda, H. Okamura, and M. Kurimoto. 1996. Cloning of the cDNA for human IFN-gamma-inducing factor, expression in *Escherichia coli*, and studies on the biologic activities of the protein. *J. Immunol.* 156:4274-4279.34.

Ushio, S, Namba M. Okura T, et al: Cloning of the cDNA for human IFN-gamma-inducing factor, expression in *Escherichia coli*, and studies on the biologic activities of the protein. J.Immunol. 156:4274-4279, 1996.

Okayama, H. and Berg, P. (1983) A cDNA cloning vector that permits expression of cDNA inserts in mammalian cells. Mol. Cell. Biol. 3:280-289.

Otsuka A..J. et al. EMBL Database Entry U39847, GenBank accession No. AAB41827 Feb. 3, 1997.

Vidal-Vanaclocha F, Fantuzzi G, et al.: IL 18 Regulates IL-18-Dependent Hepatic Melanoma Metastasis Via Vascular Cell Adhesion Molecule-1, PNAS 97(2): 734-739.

Walker W, Aste-Amezaga M, Kastelein RA, et al: IL-18 and CD28 use distinct molecular mechanisms to enhance NK cell production of IL-12-induced IFN-gamma. J.Immunol. 162:5894-5901, 1999.

Wei X, Leung BP, Arthur HM, et al: Reduced incidence and severity of collagen-induced arthritis in mice lacking IL-18 [In Process Citation]. J. Immunol 166:517-521, 2001.

Yamanaka K, Tanaka M, Tsutsui H, et al: Skin-Specific Caspase-1-Transgenic Mice Show Cutaneous Apoltosis and Pre-Endotoxin Shock Condition with a High Serum Level of IL-18. J.Immunol. 165:997-1003, 2000.

Yang, C.H. et al., EMBL Database Entry HSNUMAMR, GenBank accession No. Z115583 Feb. 17, 1997.

Yasuda, H., et al., *Identity of osteoclastogenesis inhibitory factor (OCIF) and osteoprotegerin (OPG): a mechanism by which OPG/OCIF inhibits osteoclastogenesis in vitro.* Endocrinology, 1998. 139: p. 1329-1337.

SEQUENCE LISTING

<160> NUMBER OF SEQ ID NOS: 17

<210> SEQ ID NO 1
<211> LENGTH: 1348
<212> TYPE: DNA
<213> ORGANISM: Homo sapiens

<400> SEQUENCE: 1

```
gagaagagga cgttgtcaca gataaagagc caggctcacc agctcctgac gcatgcatca      60
tgaccatgag acacaactgg acaccagacc tcagcccttt gtgggtcctg ctcctgtgtg     120
cccacgtcgt cactctcctg gtcagagcca cacctgtctc gcagaccacc acagctgcca     180
ctgcctcagt tagaagcaca aaggacccct gccctccca gccccagtg ttcccagcag      240
ctaagcagtg tccagcattg gaagtgacct ggccagaggt ggaagtgcca ctgaatggaa     300
cgctgagctt atcctgtgtg gcctgcagcc gcttcccaa cttcagcatc ctctactggc     360
tgggcaatgg ttccttcatt gagcacctcc caggccgact gtgggagggg agcaccagcc     420
gggaacgtgg gagcacaggt acgcagctgt gcaaggcctt ggtgctggag cagctgaccc     480
ctgccctgca cagcaccaac ttctcctgtg tgctcgtgga ccctgaacag gttgtccagc     540
gtcacgtcgt cctggcccag ctctgggctg ggctgagggc aaccttgccc ccacccaag     600
aagccctgcc ctccagccac agcagtccac agcagcaggg ttaagactca gcacagggcc     660
agcagcagca caaccttgac cagagcttgg gtcctacctg tctacctgga gtgaacagtc     720
cctgactgcc tgtaggctgc gtggatgcgc aacacacccc ctccttctct gctttgggtc     780
ccttctctca ccaaattcaa actccattcc cacctaccta gaaaatcaca gcctcctat      840
aatgcctcct cctcctgcca ttctctctcc acctatccat tagccttcct aacgtcctac     900
tcctcacact gctctactgc tcagaaacca ccaagactgt tgatgcctta gccttgcact     960
ccagggccct acctgcattt cccacatgac tttctggaag cctcccaact attcttgctt    1020
ttcccagaca gctcccactc ccatgtctct gctcatttag tcccgtcttc ctcaccgccc    1080
cagcagggga acgctcaagc ctggttgaaa tgctgcctct tcagtgaagt catcctcttt    1140
cagctctggc cgcattctgc agacttccta tcttcgtgct gtatgttttt tttttccccc    1200
ttcactctaa tggactgttc cagggaaggg atggggcac cagctgcttc ggatccacac     1260
tgtatctgtg tcatccccac atgggtcctc ataaaggatt attcaatgga aaaaaaaaa     1320
aaaaaaaaa aaaaaaaaa aaaaaaaa                                         1348
```

<210> SEQ ID NO 2
<211> LENGTH: 192
<212> TYPE: PRT

<213> ORGANISM: Homo sapiens
<220> FEATURE:
<221> NAME/KEY: SIGNAL
<222> LOCATION: (1)..(28)

<400> SEQUENCE: 2

| | | | | | | | | | | | | | | | |
|---|---|---|---|---|---|---|---|---|---|---|---|---|---|---|---|
| Met | Arg | His | Asn | Trp | Thr | Pro | Asp | Leu | Ser | Pro | Leu | Trp | Val | Leu | Leu |
| 1 | | | | 5 | | | | | 10 | | | | | 15 | |
| Leu | Cys | Ala | His | Val | Val | Thr | Leu | Leu | Val | Arg | Ala | Thr | Pro | Val | Ser |
| | | | 20 | | | | | 25 | | | | | 30 | | |
| Gln | Thr | Thr | Thr | Ala | Ala | Thr | Ala | Ser | Val | Arg | Ser | Thr | Lys | Asp | Pro |
| | | | 35 | | | | | 40 | | | | | 45 | | |
| Cys | Pro | Ser | Gln | Pro | Pro | Val | Phe | Pro | Ala | Ala | Lys | Gln | Cys | Pro | Ala |
| | 50 | | | | | 55 | | | | | 60 | | | | |
| Leu | Glu | Val | Thr | Trp | Pro | Glu | Val | Glu | Val | Pro | Leu | Asn | Gly | Thr | Leu |
| 65 | | | | | 70 | | | | | 75 | | | | | 80 |
| Ser | Leu | Ser | Cys | Val | Ala | Cys | Ser | Arg | Phe | Pro | Asn | Phe | Ser | Ile | Leu |
| | | | | 85 | | | | | 90 | | | | | 95 | |
| Tyr | Trp | Leu | Gly | Asn | Gly | Ser | Phe | Ile | Glu | His | Leu | Pro | Gly | Arg | Leu |
| | | | | 100 | | | | | 105 | | | | | 110 | |
| Trp | Glu | Gly | Ser | Thr | Ser | Arg | Glu | Arg | Gly | Ser | Thr | Gly | Thr | Gln | Leu |
| | | | | 115 | | | | | 120 | | | | | 125 | |
| Cys | Lys | Ala | Leu | Val | Leu | Glu | Gln | Leu | Thr | Pro | Ala | Leu | His | Ser | Thr |
| | 130 | | | | | 135 | | | | | 140 | | | | |
| Asn | Phe | Ser | Cys | Val | Leu | Val | Asp | Pro | Glu | Gln | Val | Val | Gln | Arg | His |
| 145 | | | | | 150 | | | | | 155 | | | | | 160 |
| Val | Val | Leu | Ala | Gln | Leu | Trp | Ala | Gly | Leu | Arg | Ala | Thr | Leu | Pro | Pro |
| | | | | 165 | | | | | 170 | | | | | 175 | |
| Thr | Gln | Glu | Ala | Leu | Pro | Ser | Ser | His | Ser | Ser | Pro | Gln | Gln | Gln | Gly |
| | | | | 180 | | | | | 185 | | | | | 190 | |

<210> SEQ ID NO 3
<211> LENGTH: 1038
<212> TYPE: DNA
<213> ORGANISM: Homo sapiens

<400> SEQUENCE: 3

| | | | | | | |
|---|---|---|---|---|---|---|
| gagaagagga | cgttgtcaca | gataaagagc | caggctcacc | agctcctgac | gcatgcatca | 60 |
| tgaccatgag | acacaactgg | acaccagacc | tcagcccttt | gtgggtcctg | ctcctgtgtg | 120 |
| cccacgtcgt | cactctcctg | gtcagagcca | cctgtctc | gcagaccacc | acagctgcca | 180 |
| ctgcctcagt | tagaagcaca | aaggacccct | gcccctccca | gcccccagtg | ttcccagcag | 240 |
| ctaagcagtg | tccagcattg | gaagtgacct | ggccagaggt | ggaagtgcca | ctgagctggg | 300 |
| ctgagggcaa | ccttgccccc | cacccaagaa | gccctgccct | ccagccacag | cagtccacag | 360 |
| cagcagggtt | aagactcagc | acagggccag | cagcagcaca | accttgacca | gagcttgggt | 420 |
| cctacctgtc | tacctggagt | gaacagtccc | tgactgcctg | taggctgcgt | ggatgcgcaa | 480 |
| cacacccct | cctctctgc | tttgggtccc | ttctctcacc | aaattcaaac | tccattccca | 540 |
| cctacctaga | aaatcacagc | ctccttataa | tgcctcctcc | tcctgccatt | ctctctccac | 600 |
| ctatccatta | gccttcctaa | cgtcctactc | ctcacactgc | tctactgctc | agaaaccacc | 660 |
| aagactgttg | atgccttagc | cttgcactcc | agggccctac | ctgcatttcc | cacatgactt | 720 |
| tctggaagcc | tcccaactat | tcttgctttt | cccagacagc | tcccactccc | atgtctctgc | 780 |
| tcatttagtc | ccgtcttcct | caccgcccca | gcaggggaac | gctcaagcct | ggttgaaatg | 840 |

```
ctgcctcttc agtgaagtca tcctctttca gctctggccg cattctgcag acttcctatc    900
ttcgtgctgt atgttttttt tttccccctt cactctaatg gactgttcca gggaagggat    960
gggggcacca gctgcttcgg atccacactg tatctgtgtc atccccacat gggtcctcat   1020
aaaggattat tcaatgga                                                 1038
```

<210> SEQ ID NO 4
<211> LENGTH: 113
<212> TYPE: PRT
<213> ORGANISM: Homo sapiens
<220> FEATURE:
<221> NAME/KEY: SIGNAL
<222> LOCATION: (1)..(28)

<400> SEQUENCE: 4

```
Met Arg His Asn Trp Thr Pro Asp Leu Ser Pro Leu Trp Val Leu Leu
  1               5                  10                  15

Leu Cys Ala His Val Val Thr Leu Leu Val Arg Ala Thr Pro Val Ser
                 20                  25                  30

Gln Thr Thr Thr Ala Ala Thr Ala Ser Val Arg Ser Thr Lys Asp Pro
             35                  40                  45

Cys Pro Ser Gln Pro Pro Val Phe Pro Ala Ala Lys Gln Cys Pro Ala
         50                  55                  60

Leu Glu Val Thr Trp Pro Glu Val Glu Val Pro Leu Ser Trp Ala Glu
 65                  70                  75                  80

Gly Asn Leu Ala Pro His Pro Arg Ser Pro Ala Leu Gln Pro Gln Gln
                 85                  90                  95

Ser Thr Ala Ala Gly Leu Arg Leu Ser Thr Gly Pro Ala Ala Ala Gln
            100                 105                 110

Pro
```

<210> SEQ ID NO 5
<211> LENGTH: 7063
<212> TYPE: DNA
<213> ORGANISM: Homo sapiens

<400> SEQUENCE: 5

```
gaattcgcgg ccgcgtcgac gccagagggg ctaggatgag agacagaggg tgtgatggtg     60
ggtgctggga aatgtacccg accttggggc tggtggctgg gggagtgggt agcctgggaa    120
aggccaggat gtggacggac tggtatggca ttgagcctga agtggtccaa cttggggttc    180
cccagtgcct aggaaagttg tccccttgaa tgtcagtgtg aaggtgaagg aggaagcaga    240
tgcctgttca tatggaaaca aagacctggc tgtgaagagg ggaggcggac accaaagtcc    300
tgacacttgg gcgggacaga attgatctgt gagagactca tctagttcat accctaggtg    360
accctggggg tggcatgggg gtagattaga gatcccagtc tggtatcctc tggagagtag    420
gagtcccagg agctgaaggt ttctggccac tgaactttgg ctaaagcaga ggtgtcacag    480
ctgctcaaga ttccctggtt aaaaagtgaa agtgaaatag agggtcgggg cagtgctttc    540
ccagaaggat tgctcggcat cctgcccttc ccagaagcag ctctggtgct gaagagagca    600
ctgcctccct gtgtgactgg gtgagtccat attctctctt tgggtctcaa ttttgccttc    660
cctaatgaag gggtaagatt ggactaggta agcatcttac aaccatttgt ggtcatgaga    720
gctggggtgg ggaaggattg tcacttgacc cccccagctc tgtttctaag tgctgaaaga    780
gctccaggct atgctacggg aggagaagcc agctactgag gaaaagccag ctactgagaa    840
aaagcgggag tggtttacca ttctcctccc ccacctttca ccagagaaga ggacgttgtc    900
```

-continued

```
acacataaag agccaggctc accagctcct gacgcatgca tcatgaccat gagacacaac    960
tggacaccag acctcagccc tttgtgggtc ctgctcctgt gtgcccacgt cgtcactctc   1020
ctggtcagag ccacacctgt ctcgcagacc accacagctg ccactgcctc agttagaagc   1080
acaaaggacc cctgcccctc ccagccccca gtgttcccag cagctaagca gtgtccagca   1140
ttggaagtga cctggccaga ggtggaagtg ccactgaatg gaacgctgag cttatcctgt   1200
gtggcctgca gccgcttccc caacttcagc atcctctact ggctgggcaa tggttccttc   1260
attgagcacc tcccaggccg actgtgggag gggagcacca gccgggaacg tgggagcaca   1320
ggtacgcagc tgtgcaaggc cttggtgctg agcagctga  ccctgccct gcacagcacc   1380
aacttctcct gtgtgctcgt ggaccctgaa caggttgtcc agcgtcacgt cgtcctggcc   1440
cagctctggg tgaggagccc aaggagaggc tccaggaac aggaggagct ctgcttccat    1500
atgtggggag gaaagggtgg gctctgccag agcagcctgt gaactaatgc ccagcattcc   1560
tcaaggtcag ccagacaaaa aggaacttag gtcttgggca gaggaggtgt agcctggggc   1620
aaagtgatga gatgtccctc cttccttgg cctgatcctt gtctgccttc acttccctag    1680
gctgggctga gggcaacctt gccccccacc caagaagccc tgccctccag ccacagcagt   1740
ccacagcagc agggttaaga ctcagcacag ggccagcagc agcacaacct tgaccagagc   1800
ttgggtccta cctgtctacc tggagtgaac agtccctgac tgcctgtagg ctgcgtggat   1860
gcgcaacaca cccctccctt ctctgctttg ggtcccttct ctcaccaaat tcaaactcca   1920
ttcccaccta cctagaaaat cacagcctcc ttataatgcc tcctcctcct gccattctct   1980
ctccacctat ccattagcct tcctaacgtc ctactcctca cactgctcta ctgctcagaa   2040
accaccaaga ctgttgatgc cttagccttg cactccaggg ccctacctgc atttcccaca   2100
tgactttctg gaagcctccc aactattctt gcttttccca gacagctccc actcccatgt   2160
ctctgctcat ttagtcccgt cttcctcacc gccccagcag gggaacgctc aagcctggtt   2220
gaaatgctgc ctcttcagtg aagtcatcct cttcagctc tggccgcatt ctgcagactt    2280
cctatcttcg tgctgtatgt tttttttttc cccttcact ctaatggact gttccaggga    2340
agggatgggg gcagcagctg cttcggatcc acactgtatc tgtgtcatcc ccacatgggt   2400
cctcataaag gattattcaa tggaggcatc ctgacatctg ttcatttagg cttcagttcc   2460
actcccagga actttgcctg tcccacgagg gagtatggga gagatggact gccacacaga   2520
agctgaagac aacacctgct tcaggggaac acaggcgctt gaaaagaaa agagagaaca    2580
gcccataatg ctccccggga gcagaggcca ctaatggaga gtgggaagag cctggaaaga   2640
tgtggcctca ggaaaaggga tgagagaaag gaggtggtat ggaagactca gcaggaacaa   2700
ggtaggcttc aaagagccta tattcctctt tttcccacac cgatcaagtc aactcagtac   2760
tcacgggaga aaaatagact ttatttacaa gtaataacat ttagaaaaga tccatccccg   2820
gcccttaaaa accttcccat cactccaaat cccacccag tgcaagtctg ggaaggtag     2880
ggtgtgagct gctgctgaag gctgtccccc aaccccactc ctgagacaca gggcccatcc   2940
gtcctgggaa agagcatcct ctggcaggtg ctcccaccag gtcagaccca gtcctggact   3000
tcaagagtga gggcccctgc tgggcccagc caccaggaca gcaggaacca gggcctactc   3060
ctcttatggt cccttctaga tccagaggct aagaggaaga ctggccaggc caaggaccc    3120
agccatcaaa accagcctca aatctggttg tgatggagaa gtgactttgc tttaagaaaa   3180
aaggaggcaa ggtagggaga gcgcccacac tgtccatgct ccaggccccc tgggccagct   3240
```

```
ccgagaaggc gccagtgaag gaccagggac caggccaggg tgcgggcagg catcactgtc   3300
tctaggggtt tggctactgt tggcctggga gctgagagaa ggcactgaga gggacagtag   3360
gcggaggacc aggtgacggc agcatcgggg acacaggtgg ggccactcac tggtactggc   3420
cctttagtgc tttgcctgaa agagacacag tcacatggcc agatgagaac ttgcgatact   3480
agcctgcacc cactggctgg gaagatctct tcctgctccc acgcccctgt ctggatcccc   3540
tcccttgtga gccccagggt tatcagttgc tggctgtgcc tgagcagctc tgggtgctct   3600
ccatgagaat ggggccatct gtcttctctc cttggagagg agctaccagg acagggacac   3660
ctcttacccc acaccctcca gcagcctggc gtggcccat cttggatgct acttggtggg   3720
gcggtctggg gggtgcccat gctctcatcg ggtttccctc ccccatcctg ccagtgcctc   3780
taccttgccc ttggctcgag gggtggcacc aatggcggca gcagtggcgg cgctggctgt   3840
ggtggtggca atgcgcggag aacggcgggt tccactgcga gtgttggggg aagccttgga   3900
cagggccttc tttgaggctc cccgccgcag aaggctgttc cctagcttct tgggtgtgtt   3960
gaggatgctg aaggccatcg actggcgccg gtcagcctgc aaggaagggc tgtcagaccg   4020
ggagacccaa tgctgccttc caggccagc gtgctgtgcc acgctgtacc agcaaggtcc   4080
cgccagggcg tcgcttcatc cccttcagc cccagcctca cctgtttagt agaagctgga   4140
gctgctttct tctgggcctc agtagtgctc tgtttgcgcc cttcatgtcg gtctcgggga   4200
gtcatggggc gtgggaaaca gctggtggcc ttcttagact atggagaaga ggacagttag   4260
gcagacagta gcaagaggag tcacatctga agccaggtgt cttgtcctct cagagctgag   4320
tggaccttgt aagtcaacgt gcaacctgct ccccttccca actctgggcc agatccttcc   4380
cttcccaaca gttcccatcc atgggtcagg cccttggaga gagggaaaga gaggggaag   4440 tgagggaagg agagagaagg ctcccttag tccttggtga gctgggcctg acctgagcac   4500
agtgctggag taacacccag gagccaccgc gcctacctca ggagttccag ggccctggtg   4560
gggctctagg gagacccgtt tgcgctgctg ccgggtggtg atgccagtgc cctcggctat   4620
ctggattggc tgcatgctgg ctcggcgcag ggtctcttgg gggtctccag ttttcatctc   4680
ctcatctgtg atggtgccca ggctcaggga aggctgcatg ggtggaagag gtggtcagtg   4740
gaccatagct gtatggagat ggaggaggac ctggggctgt tccagaactc tacactcgcc   4800
cgacacttat ggtcgggacc cttcctgcct acgaggtaga aagacacaag cctcctttcc   4860
tgttctgctt tctacctaag ccctgggcaa atggcacaag cagtgcagtc ctgaccagat   4920
tcctctctga gctcctgcct accccaggg acttcacccc tgagtgccct ccagctgtct   4980
gttccacctg gaacatgaga aggtcacccc ttcccctctt cggccagtca gtgatccagg   5040
gccctagtgc tcaggctaga tcagcaggtg ggattccaag gaagggcagg gatgggaggc   5100
cctgcacagt gaccccaggc ctcaccctgg actccaggga tagcaggtct tcagatgtgg   5160
ggggcacact cgattgcgct gctgcagctc tgcaatgcgg ttccagtcat ccagctgctc   5220
aggctcatcc tggcaagtgc ccatgtagaa gctgttcctt cctgtggaag gcagggaagt   5280
gggaacaaat gagcctggag tcggcaggtc acctcctggc cctggcatct tgccagcctt   5340
tgctgccacc tacccataa acttgaagcc cggcacacca gtctgattca gtgccgcagg   5400
tgcaggagta cggcacacag actatttcta tcctaggggc ttgctcacca ccttctcct   5460 ggagagggca gaagaggtca cacgcagaga ctgctactac atcttattca cctgccaagg   5520
cttggtggcc aacacccaga ggaacaaatt aaggaccggg aattaattcc caggggctcc   5580
ctggtgccca aggacaaga gcttccaaga agagtctggc cagcctggcc tttccagcag   5640
```

```
cccatcaccg cctgagaagg gcatggagga ctccccacag ctaagtgtca caattgtgct    5700
gggaatcccg ggcccttaac tctggctaag agtgccccca acacagccag cccctagatg    5760
ggcaggtaag gaaggccctg aggctgcagg aaggaggggc aggtggagct ggatggtagc    5820
aaggaggcca gccttggatt tttaaaaagc tttcctcttt tccctgtgcc acgatccacc    5880
ttccagtcta attttggggt atagtaagtc cctgtagtcc cctcacctgg aggggcccca    5940
ctggacaccc cggcctggga acgacgagca gaactgcgag tggtggggcg gtagccaggc    6000
aagctgagca gggctgagtt gccataatcg ggagaaccca ggcgagctag agactgagta    6060
gaggaggtgg ctcgcaggct agcctgggaa gcaggagcag accgcgtgct gtagaacgat    6120
gagttggcgc tgtctggctc ttccacatct agcttctgga agacagagtg aatctgttgc    6180
agtgtacagt ccctggcact gtacagaagc ttcccattcc cttccgaagc cctcagatcc    6240
cacggcacat ccatgtattc ccaactgctt tgcaaaggtc cttaaagtgt gtgtctgcaa    6300
gaaatgggcc ttgtcgacag aagccctcac aaggtggtgc tgatgttgtc aagactcttc    6360
tacgcatttt tttcatggag tctattcata atgctttgag gtaggaatg cagagtgttt     6420 atcggcccat tttggagatg aagtgcaaag aaataaagtg actagcccca aatcacactg    6480
ctaggaagta tcagagctgg ggctaggccc catgtctcct gactagtcag gctcatccca    6540
cagcctctgc tgtccctcag tccaaacttc cagggccctt accatgttcc agaacttccc    6600
ccaacttctt ggtagcaggg ggcacccaaa acacacaggt ccccccctgct gtaccagggg    6660 cccctctcc cctcctccca aacctcccct tcaagatgtg gaaacaaagg caagggcctg     6720
cagcctgtca ggcagtccac tgggcagcaa caatgcctct cagctgcatg gggcatgctg    6780
ggaggcacag gatgggctgc agcttcgcca cgttctctcc cttcaccctg cacaggctca    6840
gtgctacgca tggagagaat gctagcctta gtcaggaggc agggatctaa tcctagccct    6900 gccttttttct tcagaagtgc ccttaaccaa gtcactgccc ttttttaagac ctctcagctt    6960 tcccactgta acatggactg gctgctcatc cctccctgct cctgactgag tgcccagtgc    7020
aaagatgccc ttgagaggaa gtgggaattg ctgacctgtc gac                      7063
```

<210> SEQ ID NO 6
<211> LENGTH: 197
<212> TYPE: PRT
<213> ORGANISM: Homo sapiens
<220> FEATURE:
<221> NAME/KEY: SIGNAL
<222> LOCATION: (1)..(28)

<400> SEQUENCE: 6

```
Met Arg His Asn Trp Thr Pro Asp Leu Ser Pro Leu Trp Val Leu Leu
 1               5                  10                  15

Leu Cys Ala His Val Val Thr Leu Leu Val Arg Ala Thr Pro Val Ser
                20                  25                  30

Gln Thr Thr Thr Ala Ala Thr Ala Ser Val Arg Ser Thr Lys Asp Pro
            35                  40                  45

Cys Pro Ser Gln Pro Pro Val Phe Pro Ala Ala Lys Gln Cys Pro Ala
        50                  55                  60

Leu Glu Val Thr Trp Pro Glu Val Glu Val Pro Leu Asn Gly Thr Leu
    65                  70                  75                  80

Ser Leu Ser Cys Val Ala Cys Ser Arg Phe Pro Asn Phe Ser Ile Leu
                85                  90                  95

Tyr Trp Leu Gly Asn Gly Ser Phe Ile Glu His Leu Pro Gly Arg Leu
```

|   |   |   |   |   |   |   |   |   |   |   |   |
|---|---|---|---|---|---|---|---|---|---|---|---|
|   |   |   | 100 |   |   |   | 105 |   |   |   | 110 |
| Trp | Glu | Gly | Ser | Thr | Ser | Arg | Glu | Arg | Gly | Ser | Thr | Gly | Thr | Gln | Leu |
|   |   |   | 115 |   |   |   | 120 |   |   |   | 125 |
| Cys | Lys | Ala | Leu | Val | Leu | Glu | Gln | Leu | Thr | Pro | Ala | Leu | His | Ser | Thr |
|   |   |   | 130 |   |   |   | 135 |   |   |   | 140 |
| Asn | Phe | Ser | Cys | Val | Leu | Val | Asp | Pro | Glu | Gln | Val | Val | Gln | Arg | His |
| 145 |   |   |   |   | 150 |   |   |   |   | 155 |   |   |   |   | 160 |
| Val | Val | Leu | Ala | Gln | Leu | Trp | Val | Arg | Ser | Pro | Arg | Arg | Gly | Leu | Gln |
|   |   |   |   | 165 |   |   |   |   | 170 |   |   |   |   | 175 |
| Glu | Gln | Glu | Glu | Leu | Cys | Phe | His | Met | Trp | Gly | Gly | Lys | Gly | Gly | Leu |
|   |   |   | 180 |   |   |   | 185 |   |   |   | 190 |
| Cys | Gln | Ser | Ser | Leu |
|   |   |   | 195 |

```
<210> SEQ ID NO 7
<211> LENGTH: 1360
<212> TYPE: DNA
<213> ORGANISM: Homo sapiens

<400> SEQUENCE: 7
gcggccgcgt cgaccacgca gctaaacaca gctaacttga gtcttggagc tcctaaaggg      60
aagcttctgg aaaggaaggc tcttcaggac ctcttaggag ccaaagaaga ggacgttgtc     120
acagataaag agccaggctc accagctcct gacgcatgca tcatgaccat gagacacaac     180
tggacaccag acctcagccc tttgtgggtc ctgctcctgt gtgcccacgt cgtcactctc     240
ctggtcagag ccacacctgt ctcgcagacc accacagctg ccactgcctc agttagaagc     300
acaaaggacc cctgcccctc ccagccccca gtgttcccag cagctaagca gtgtccagca     360
ttggaagtga cctggccaga ggtggaagtg ccactgaatg gaacgctgag cttatcctgt     420
gtggcctgca ccgcttccc caacttcagc atcctctact ggctgggcaa tggttccttc     480
attgagcacc tcccaggccg actgtgggag gggagcacca gccgggaacg tgggagcaca     540
ggctgggctg agggcaacct tgccccccac ccaagaagcc ctgccctcca gccacagcag     600
tccacagcag cagggttaag actcagcaca gggccagcag cagcacaacc ttgaccagag     660
cttgggtcct acctgtctac ctggagtgaa cagtccctga ctgcctgtag ctgcgtggca     720
tgcgcaacac ccccctcct tctctgcttt gggtcccttc tctcaccaaa ttcaaactcc     780
attcccacct acctagaaaa tcacagcctc cttataatgc ctcctcctcc tgccattctc     840
tctccaccta tccattagcc ttcctaacgt cctactcctc acactgctct actgctcaga     900
aaccaccaag actgttgatg ccttagcctt gcactccagg gccctacctg catttcccac     960
atgactttct ggaagcctcc caactattct tgcttttccc agacagctcc cactcccatg    1020
tctctgctca tttagtcccg tcttcctcac cgccccagca ggggaacgct caagcctggt    1080
tgaaatgctg cctcttcagt gaagtcatcc tctttcagct ctggccgcat tctgcagact    1140
tcctatcttc gtgctgtatg tttttttttt ccccccttcac tctaatggac tgttccaggg    1200
aagggatggg ggcagcagct gcttcggatc cacactgtat ctgtgtcatc cccacatggg    1260
tcctcataaa ggattattca atggaggcat cctgacatct gtccatttag gcttcagttc    1320
cactcccagg aactttgcct gtcccacgag ggagtatggg                          1360

<210> SEQ ID NO 8
<211> LENGTH: 161
<212> TYPE: PRT
<213> ORGANISM: Homo sapiens
```

```
<220> FEATURE:
<221> NAME/KEY: SIGNAL
<222> LOCATION: (1)..(28)

<400> SEQUENCE: 8

Met Arg His Asn Trp Thr Pro Asp Leu Ser Pro Leu Trp Val Leu Leu
 1               5                  10                  15

Leu Cys Ala His Val Val Thr Leu Leu Val Arg Ala Thr Pro Val Ser
                20                  25                  30

Gln Thr Thr Thr Ala Ala Thr Ala Ser Val Arg Ser Thr Lys Asp Pro
            35                  40                  45

Cys Pro Ser Gln Pro Pro Val Phe Pro Ala Ala Lys Gln Cys Pro Ala
 50                  55                  60

Leu Glu Val Thr Trp Pro Glu Val Glu Val Pro Leu Asn Gly Thr Leu
 65                  70                  75                  80

Ser Leu Ser Cys Val Ala Cys Ser Arg Phe Pro Asn Phe Ser Ile Leu
                85                  90                  95

Tyr Trp Leu Gly Asn Gly Ser Phe Ile Glu His Leu Pro Gly Arg Leu
                100                 105                 110

Trp Glu Gly Ser Thr Ser Arg Glu Arg Gly Ser Thr Gly Trp Ala Glu
            115                 120                 125

Gly Asn Leu Ala Pro His Pro Arg Ser Pro Ala Leu Gln Pro Gln Gln
130                 135                 140

Ser Thr Ala Ala Gly Leu Arg Leu Ser Thr Gly Pro Ala Ala Ala Gln
145                 150                 155                 160

Pro

<210> SEQ ID NO 9
<211> LENGTH: 7812
<212> TYPE: DNA
<213> ORGANISM: Homo sapiens

<400> SEQUENCE: 9
gtcgacggta cccccgggaa agatttaata cgactcacta tagggcggga cagaattgat      60
ctgtgagaga ctcatctagt tcataccceta ggtgaccctg ggggtggcat ggggggtagat    120
tagagatccc agtctggtat cctctggaga gtaggagtcc caggagctga aggtttctgg     180
ccactgaact ttggctaaag cagaggtgtc acagctgctc aagattccct ggttaaaaag     240
tgaaagtgaa atagagggtc ggggcagtgc tttcccagaa ggattgctcg gcatcctgcc     300
cttcccagaa gcagctctgg tgctgaagag agcactgcct ccctgtgtga ctgggtgagt     360
ccatattctc tctttgggtc tcaatttgc cttccctaat gaaggggtaa gattggacta     420
ggtaagcatc ttacaaccat ttgtggtcat gagagctggg gtggggaagg attgtcactt     480
gacccccca gctctgtttc taagtgctga aagagctcca ggctatgcta cgggaggaga     540
agccagctac tgaggaaaag ccagctactg agaaaaagcg ggagtggttt accattctcc     600
tcccccacct ttcaccagag aagaggacgt tgtcacacat aaagagccag gctcaccagc     660
tcctgacgca tgcatcatga ccatgagaca caactggaca ccaggtaggc cttgggcta      720
cgcatgggca ggcggggtag ggtgaggtct atgaacagaa tggagcaatg gctaacccg      780
gagccttcac tccaaggcaa accacccagc gcacctggtg ctgttgcttt aagaacctgg     840
gcagatattg tagctctggc tccagtctaa agcttctctg tactctgttc aataaagggc     900
taaggggtgg gtgctgaggg gtccctcttc ccgctctgat tccctggcta gaacccagac     960
atctctgggc tggagttaca tccttacccg ggcagcccac tctgtctcca gagccgctga   1020
```

```
cctgtaactg tcctttcctc agacctcagc cctttgtggg tcctgctcct gtgtgcccac    1080
gtcgtcactc tcctggtcag agccacacct gtctcgcaga ccaccacagc tgccactgcc    1140
tcagttagaa gcacaaagga cccctgcccc tcccagcccc cagtgttccc agcagctaag    1200
cagtgtccag cattggaagt gacctggcca gaggtggaag tgccactgag taagaagcac    1260
agtggtggag ggtgggctat gggcacagag gttcccaggg tcgggttgac tcctgagcgc    1320
cagtccccct ctgcccatgt accaccagct gagccagctg gctgagcac gcaccattct     1380
ccctccccaa cccagtgtca tgggtgcagg cttggcgcag ctcccaagat gctccctatc    1440
aaataggaca gagaactcaa gacataagta atggtcacag gacctcccag agccttggtt    1500
gcagtggacc ccaaggccag cccctccacc cagagcctgc tggcctctgg ccatctcaga    1560
ggagcagcag ccatccagca ctgcctctgt cacctgggct cccaagtcac cgaggctggg    1620
cactagaaaa ggtcatcctg aggagacagg ttcagaagag gattcatcac gtgaaccaag    1680
gaccattcct cacattcccc gtgtttaggg ctagggcctc tcggagacaa ctgcacttct    1740
gtaacgacg ttcccaccta ggtggtgtgc agagcagttc tctaggttcc agatgcatgg     1800
ggactggggg gagctggcag agagggcaca gcagagcagg gtaggggaag ggcctgctct    1860
tctgaagagc taactgctgc ctgtgtccct agatggaacg ctgagcttat cctgtgtggc    1920
ctgcagccgc ttccccaact tcagcatcct ctactggctg gcaatggtt ccttcattga     1980
gcacctccca ggccgactgt gggagggag caccaggtga gggtcgcagc agccaggtgg     2040
gtgggaagga agccttctgc ggccttctca tgaccttcc ttcccttccg ctccagccgg     2100
gaacgtggga gcacaggtac gcagctgtgc aaggccttgg tgctggagca gctgaccct    2160
gccctgcaca gcaccaactt ctcctgtgtg ctcgtggacc ctgaacaggt tgtccagcgt    2220
cacgtcgtcc tggcccagct ctgggtgagg agcccaagga gaggcctcca ggaacaggag    2280
gagctctgct tccatatgtg gggaggaaag ggtgggctct gccagagcag cctgtgaact    2340
aatgcccagc attcctcaag gtcagccaga caaaaaggaa cttaggtctt gggcagagga    2400
ggtgtagcct ggggcaaagt gatgagatgt ccctcctttc cttggcctga tccttgtctg    2460
ccttcacttc cctaggctgg gctgagggca accttgcccc cacccaaga agccctgccc     2520
tccagccaca gcagtccaca gcagcagggt taagactcag cacagggcca gcagcagcac    2580
aaccttgacc agagcttggg tcctacctgt ctacctggag tgaacagtcc ctgactgcct    2640
gtaggctgcg tggatgcgca acacaccccc tccttctctg ctttgggtcc cttctctcac    2700
caaattcaaa ctccattccc acctacctag aaaatcacag cctccttata atgcctcctc    2760
ctcctgccat tctctctcca cctatccatt agccttccta acgtcctact cctcacactg    2820
ctctactgct cagaaaccac caagactgtt gatgccttag ccttgcactc cagggcccta    2880
cctgcatttc ccacatgact ttctggaagc ctcccaacta ttcttgcttt tcccagacag    2940
ctcccactcc catgtctctg ctcatttagt cccgtcttcc tcaccgcccc agcagggaa     3000
cgctcaagcc tggttgaaat gctgcctctt cagtgaagtc atcctctttc agctctggcc    3060
gcattctgca gacttcctat cttcgtgctg tatgttttt ttttcccct tcactctaat      3120
ggactgttcc agggaaggga tggggcagc agctgcttcg gatccacact gtatctgtgt    3180
catccccaca tgggtcctca taaggatta ttcaatggag gcatcctgac atctgttcat     3240
ttaggcttca gttccactcc caggaacttt gcctgtccca cgagggagta tgggagagat    3300
ggactgccac acagaagctg aagacaacac ctgcttcagg ggaacacagg cgcttgaaaa    3360
```

```
agaaaagaga gaacagccca taatgctccc cgggagcaga ggccactaat ggagagtggg   3420
aagagcctgg aaagatgtgg cctcaggaaa agggatgaga gaaaggaggt ggtatggaag   3480
actcagcagg aacaaggtag gcttcaaaga gcctatattc ctcttttcc cacaccgatc    3540 aagtcaactc agtactcacg ggagaaaaat agactttatt tacaagtaat aacatttaga   3600
aaagatccat ccccggccct taaaaacctt cccatcactc caaatcccac cccagtgcaa   3660 gtctgggaa ggtagggtgt gagctgctgc tgaaggctgt cccccaaccc cactcctgag    3720
acacagggcc catccgtcct gggaaagagc atcctctggc aggtgctccc accaggtcag   3780
acccagtcct ggacttcaag agtgagggcc cctgctgggc ccagccacca ggacagcagg   3840
aaccagggcc tactcctctt atggtccctt ctagatccag aggctaagag gaagactggc   3900
caggcccaag gacccagcca tcaaaaccag cctcaaatct ggttgtgatg agaagtgac    3960 tttgctttaa gaaaaagga ggcaaggtag ggagagcgcc cacactgtcc atgctccagg    4020 cccctgggc cagctccgag aaggcgccag tgaaggacca gggaccaggc cagggtgcgg    4080
gcaggcatca ctgtctctag gggtttggct actgttggcc tgggagctga gagaaggcac   4140
tgagagggac agtaggcgga ggaccaggtg acggcagcat cggggacaca ggtggggcca   4200
ctcactggta ctggcccttt agtgctttgc ctgaaagaga cacagtcaca tggccagatg   4260
agaacttgcg atactagcct gcacccactg gctgggaaga tctcttcctg ctcccacgcc   4320
cctgtctgga tcccctccct tgtgagcccc agggttatca gttgctggct gtgcctgagc   4380
agctctgggt gctctccatg agaatggggc catctgtctt ctctccttgg agaggagcta   4440
ccaggacagg gacacctctt accccacacc ctccagcagc ctggcgtggc cccatcttgg   4500
atgctacttg gtggggcggt ctgggggtg cccatgctct catcgggttt ccctcccca    4560 tcctgccagt gcctctacct tgcccttggc tcgaggggtg gcaccaatgg cggcagcagt   4620
ggcggcgctg gctgtggtgg tggcaatgcg cggagaacgg cgggttccac tgcgagtgtt   4680
gggggaagcc ttggacaggg ccttctttga ggctccccgc cgcagaaggc tgttccctag   4740
cttcttgggt gtgttgagga tgctgaaggc catcgactgg cgccggtcag cctgcaagga   4800
agggctgtca gaccgggaga cccaatgctg ccttcccagg ccagcgtgct gtgccacgct   4860
gtaccagcaa ggtcccgcca gggcgtcgct tcatcccct tcagcccag cctcacctgt    4920 ttagtagaag ctggagctgc tttcttctgg gcctcagtag tgctctgttt gcgcccttca   4980
tgtcggtctc ggggagtcat ggggcgtggg aaacagctgg tggccttctt agactatgga   5040
gaagaggaca gttaggcaga cagtagcaag aggagtcaca tctgaagcca ggtgtcttgt   5100
cctctcagag ctgagtggac cttgtaagtc aacgtgcaac ctgctcccct tcccaactct   5160
gggccagatc cttcccttcc caacagttcc catccatggg tcaggccctt ggagagaggg   5220
aaagagaggg ggaagtgagg gaaggagaga gaaggctccc tttagtcctt ggtgagctgg   5280
gcctgacctg agcacagtgc tggagtaaca cccaggagcc accgcgccta cctcaggagt   5340
tccagggccc tggtggggct ctagggagac ccgtttgcgc tgctgccggg tggtgatgcc   5400
agtgccctcg gctatctgga ttggctgcat gctggctcgg cgcagggtct cttgggggtc   5460
tccagttttc atctcctcat ctgtgatggt gcccaggctc agggaaggct gcatgggtgg   5520
aagaggtggt cagtggacca tagctgtatg gagatggagg aggacctggg gctgttccag   5580
aactctacac tcgcccgaca cttatggtcg ggaccttcc tgcctacgag gtagaaagac    5640
acaagcctcc tttcctgttc tgcttttctac ctaagccctg gcaaatggc acaagcagtg   5700 cagtcctgac cagattcctc tctgagctcc tgcctacccc cagggacttc acccctgagt   5760
```

```
gccctccagc tgtctgttcc acctggaaca tgagaaggtc accccttccc ctcttcggcc      5820
agtcagtgat ccagggccct agtgctcagg ctagatcagc aggtgggatt ccaaggaagg      5880
gcagggatgg gaggccctgc acagtgaccc caggcctcac cctggactcc agggatagca      5940
ggtcttcaga tgtgggggc acactcgatt gcgctgctgc agctctgcaa tgcggttcca       6000
gtcatccagc tgctcaggct catcctggca agtgcccatg tagaagctgt tccttcctgt      6060
ggaaggcagg gaagtgggaa caaatgagcc tggagtcggc aggtcacctc ctggccctgg      6120
catcttgcca gcctttgctg ccacctaccc cataaacttg aagcccggca caccagtctg      6180
attcagtgcc gcaggtgcag gagtacggca cacagactat ttctatccta ggggcttgct      6240
caccaccttc tccctggaga gggcagaaga ggtcacacgc agagactgct actacatctt      6300
attcacctgc caaggcttgg tggccaacac ccagaggaac aaattaagga ccgggaatta      6360
attcccaggg gctccctggt gcccaaagga caagagcttc aagaagagt ctggccagcc       6420 tggcctttcc agcagcccat caccgcctga aagggcatg gaggactccc cacagctaag       6480
tgtcacaatt gtgctgggaa tcccgggccc ttaactctgg ctaagagtgc cccaacaca      6540 gccagcccct agatgggcag gtaaggaagg ccctgaggct gcaggaagga ggggcaggtg      6600
gagctggatg gtagcaagga ggccagcctt ggattttta aaagctttcc tcttttccct       6660
gtgccacgat ccaccttcca gtctaatttt ggggtatagt aagtccctgt agtcccctca     6720
cctggagggg ccccactgga caccccggcc tgggaacgac gagcagaact gcgagtggtg      6780
gggcggtagc caggcaagct gagcagggct gagttgccat aatcgggaga acccaggcga      6840
gctagagact gagtagagga ggtggctcgc aggctagcct gggaagcagg agcagaccgc      6900
gtgctgtaga acgatgagtt ggcgctgtct ggctcttcca catctagctt ctggaagaca      6960
gagtgaatct gttgcagtgt acagtccctg gcactgtaca gaagcttccc attcccttcc      7020
gaagccctca gatcccacgg cacatccatg tattcccaac tgctttgcaa aggtccttaa      7080
agtgtgtgtc tgcaagaaat gggccttgtc gacagaagcc ctcacaaggt ggtgctgatg      7140
ttgtcaagac tcttctacgc atttttttca tggagtctat tcataatgct ttgaggtagg      7200
gaatgcagag tgtttatcgg cccatttggg agatgaagtg caaagaaata aagtgactag      7260
ccccaaatca cactgctagg aagtatcaga gctggggcta ggccccatgt ctcctgacta      7320
gtcaggctca tcccacagcc tctgctgtcc ctcagtccaa acttccaggg cccttaccat      7380
gttccagaac ttccccccaac ttcttggtag caggggcac cctaaacaca caggtccccc      7440
ctgctgtacc aggggccccc tctcccctcc tcccaaacct cccccttcaag atgtggaaac      7500 aaaggcaagg gcctgcagcc tgtcaggcag tccactgggc agcaacaatg cctctcagct      7560
gcatggggca tgctgggagg cacaggatgg gctgcagctt cgccacgttc tctcccttca      7620
ccctgcacag gctcagtgct acgcatggag agaatgctag ccttagtcag gaggcaggga      7680
tctaatccta gccctgcctt tttcttcaga agtgcccta accaagtcac tgcccttttt      7740
aagacctctc agctttccca ctgtaacatg gactggctgc tcatccctcc ctgctcctga      7800
ctgagtgccc ag                                                          7812
```

<210> SEQ ID NO 10
<211> LENGTH: 40
<212> TYPE: PRT
<213> ORGANISM: Homo sapiens
<220> FEATURE:
<221> NAME/KEY: VARIANT
<222> LOCATION: (6)..(8)

```
<223> OTHER INFORMATION: wherein Xaa is any amino acid as defined in the
      specification
<220> FEATURE:
<221> NAME/KEY: VARIANT
<222> LOCATION: (11)
<223> OTHER INFORMATION: wherein Xaa is any amino acid as defined in the
      specification

<400> SEQUENCE: 10

Thr Pro Val Ser Gln Xaa Xaa Xaa Ala Ala Xaa Ala Ser Val Arg Ser
  1               5                  10                  15

Thr Lys Asp Pro Cys Pro Ser Gln Pro Pro Val Phe Pro Ala Ala Lys
             20                  25                  30

Gln Cys Pro Ala Leu Glu Val Thr
         35                  40

<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence: Chemically
      synthesized
<220> FEATURE:
<221> NAME/KEY: VARIANT
<222> LOCATION: (7)..(9)
<223> OTHER INFORMATION: wherein Xaa is any amino acid as defined in the
      specification

<400> SEQUENCE: 11

Thr Pro Val Ser Gln Gln Xaa Xaa Xaa Ala Ala Ala
  1               5                  10

<210> SEQ ID NO 12
<211> LENGTH: 40
<212> TYPE: PRT
<213> ORGANISM: Homo sapiens
<220> FEATURE:
<221> NAME/KEY: VARIANT
<222> LOCATION: (6)..(8)
<223> OTHER INFORMATION: wherein "Xaa" is any amino acid as defined in
      the specification
<220> FEATURE:
<221> NAME/KEY: VARIANT
<222> LOCATION: (11)
<223> OTHER INFORMATION: wherein "Xaa" is any amino acid as defined in
      the specification

<400> SEQUENCE: 12

Thr Pro Val Ser Gln Xaa Xaa Xaa Ala Ala Xaa Ala Ser Val Arg Ser
  1               5                  10                  15

Thr Lys Asp Pro Cys Pro Ser Gln Pro Pro Val Phe Pro Ala Ala Lys
             20                  25                  30

Gln Cys Pro Ala Leu Glu Val Thr
         35                  40

<210> SEQ ID NO 13
<211> LENGTH: 50
<212> TYPE: PRT
<213> ORGANISM: Artificial Sequence
<220> FEATURE:
<223> OTHER INFORMATION: Description of Artificial Sequence: Chemically
      synthesized
<220> FEATURE:
<221> NAME/KEY: VARIANT
<222> LOCATION: (9)
<223> OTHER INFORMATION: wherein Xaa is any amino acid as defined in the
      specification
<220> FEATURE:
```

```
<221> NAME/KEY: VARIANT
<222> LOCATION: (11)
<223> OTHER INFORMATION: wherein Xaa is any amino acid as defined in the
      specification

<400> SEQUENCE: 13

Val Thr Leu Leu Val Arg Ala Thr Xaa Val Xaa Gln Thr Thr Thr Ala
 1               5                  10                  15

Ala Thr Ala Ser Val Arg Ser Thr Lys Asp Pro Cys Pro Ser Gln Pro
            20                  25                  30

Pro Val Phe Pro Ala Ala Lys Gln Cys Pro Ala Leu Glu Val Thr Trp
        35                  40                  45

Pro Glu
    50

<210> SEQ ID NO 14
<211> LENGTH: 13
<212> TYPE: PRT
<213> ORGANISM: Artificial Sequence
<220> FEATURE:
<223> OTHER INFORMATION: Description of Artificial Sequence: Chemically
      Synthesized

<400> SEQUENCE: 14

Glu Phe Gly Ala Gly Leu Val Leu Gly Gly Gln Phe Met
 1               5                  10

<210> SEQ ID NO 15
<211> LENGTH: 12
<212> TYPE: PRT
<213> ORGANISM: Homo sapiens
<220> FEATURE:
<221> NAME/KEY: VARIANT
<222> LOCATION: (1)
<223> OTHER INFORMATION: wherein "Xaa" is any amino acid as defined in
      the specification
<220> FEATURE:
<221> NAME/KEY: VARIANT
<222> LOCATION: (4)
<223> OTHER INFORMATION: wherein "Xaa" is any amino acid as defined in
      the specification
<220> FEATURE:
<221> NAME/KEY: VARIANT
<222> LOCATION: (9)
<223> OTHER INFORMATION: wherein "Xaa" is any amino acid as defined in
      the specification

<400> SEQUENCE: 15

Ala Xaa Tyr Xaa Arg Ile Pro Ala Xaa Ala Ile Ala
 1               5                  10

<210> SEQ ID NO 16
<211> LENGTH: 37
<212> TYPE: DNA
<213> ORGANISM: Artificial Sequence
<220> FEATURE:
<223> OTHER INFORMATION: Description of Artificial Sequence: Chemically
      synthesized

<400> SEQUENCE: 16
tatatctaga gccaccatga gacacaactg gacacca                              37

<210> SEQ ID NO 17
<211> LENGTH: 50
<212> TYPE: DNA
<213> ORGANISM: Artificial Sequence
```

```
-continued

<220> FEATURE:
<223> OTHER INFORMATION: Description of Artificial Sequence: Chemically
      synthesized

<400> SEQUENCE: 17
atatctagat taatgatgat gatgatgatg accctgctgc tgtggactgc                    50
```

METHODS FOR TREATING INTERLEUKIN-18 MEDIATED DISORDERS WITH INTERLEUKIN-18 BINDING PROTEINS

RELATED APPLICATIONS

This application is a divisional application of U.S. Ser. No. 09/790,338, filed Feb. 21, 2001, (now U.S. Pat. No. 7,220, 717), which is a continuation-in-part application of U.S. Ser. No. 09/485,632, filed Oct. 12, 2000 (now U.S. Pat. No. 6,605, 280); which claims priority to and the benefit of EP application 00103590.6, filed Feb. 21, 2000; EP application 00103597.1, filed Feb. 21, 2000; EP application 00125633.8, filed Nov. 23, 2000; PCT application IL98/00379, filed Aug. 13, 1998; Israel application 125463, filed Jul. 22, 1998, Israel application 122134, filed Nov. 6, 1997; Israel application 121860, filed Sep. 29, 1997; Israel application 121639, filed Aug. 27, 1997; and Israel application 121554, filed Aug. 14, 1997. Each of these applications is incorporated by reference in its entirety.

FIELD OF THE INVENTION

The present invention relates to interleukin-18 (IL-18) binding proteins, hereinafter IL-18BP, capable of blocking the activity of IL-18. More particularly, this invention relates to soluble IL-18BPs obtainable from body fluids, to soluble IL-18BPs obtainable by expression of suitable DNA vectors in host cells, to virus-encoded homologues of IL-18BP obtainable by expression of suitable DNA vectors in host cells, to vectors expressing the various IL-18BPs, to vectors useful for expression of IL-18BPs in humans and other mammals, to antibodies against IL-18BPs, to therapeutic use of said IL-18BPs in blocking IL-18 activity, to therapeutic use of said expression vectors in blocking IL-18 activity and to use of the antibodies.

BACKGROUND OF THE INVENTION

In 1989, an endotoxin-induced serum activity that induced interferon-γ (IFN-γ) obtained from mouse spleen cells was described (Micallef et al., 1996). This serum activity functioned not as a direct inducer of IFN-γ but rather as a co-stimulant together with IL-2 or mitogens. An attempt to purify the activity from post-endotoxin mouse serum revealed an apparently homogeneous 50-55 kDa protein. Since other cytokines can act as co-stimulants for IFN-γ production, the failure of neutralizing antibodies to IL-1, IL-4, IL-5, IL-6, or TNF to neutralize the serum activity suggested it was a distinct factor. In 1995, the same scientists demonstrated that the endotoxin-induced co-stimulant for IFN-γ production was present in extracts of livers from mice pre-conditioned with P. acnes (Novick et al., 1992). In this model, the hepatic macrophage population (Kupffer cells) expand and in these mice, a low dose of bacterial lipopolysaccharide (LPS), which in non-preconditioned mice is not lethal, becomes lethal. The factor, named IFN-γ-inducing factor (IGIF) and later designated interleukin-18 (IL-18), was purified to homogeneity from 1,200 grams of P. acnes-treated mouse livers. Degenerate oligonucleotides derived from amino acid sequences of purified IL-18 were used to clone a murine IL-18 cDNA (Novick et al., 1992). IL-18 is an 18-19 kDa protein of 157 amino acids, which has no obvious similarities to any peptide in the databases. Messenger RNAs for IL-18 and interleukin-12 (IL-12) are readily detected in Kupffer cells and activated macrophages. Recombinant IL-18 induces IFN-gamma more potently than does IL-12, apparently through a separate pathway (Novick et al., 1992). Similar to the endotoxin-induced serum activity, IL-18 does not induce IFN-γ by itself, but functions primarily as a co-stimulant with mitogens or IL-2. IL-18 enhances T cell proliferation, apparently through an IL-2-dependent pathway, and enhances Th1 cytokine production in vitro and exhibits synergism when combined with IL-12 in terms of enhanced IFN-γ production (Maliszewski et al., 1990).

Neutralizing antibodies to mouse IL-18 were shown to prevent the lethality of low-dose LPS in P. acnes pre-conditioned mice. Others had reported the importance of IFN-γ as a mediator of LPS lethality in pre-conditioned mice. For example, neutralizing anti-IFN-γ antibodies protected mice against Shwartzman-like shock (Fantuzzi et al., 1998), and galactosamine-treated mice deficient in the IFN-γ receptor were resistant to LPS-induced death (Byrn, 1990). Hence, it was not unexpected that neutralizing antibodies to murine IL-18 protected P. acnes-preconditioned mice against lethal LPS (Novick et al., 1992). Anti-murine IL-18 treatment also protected surviving mice against severe hepatic cytotoxicity.

After the murine form was cloned, the human cDNA sequence for IL-18 was reported in 1996 (Okamura et al., 1995). Recombinant human IL-18 exhibits natural IL-18 activity (Okamura et al., 1995). Human recombinant IL-18 is without direct IFN-γ-inducing activity on human T-cells, but acts as a co-stimulant for production of IFN-y and other T-helper cell-1 (Th1) cytokines (Okamura et al., 1995). To date, IL-18 is thought of primarily as a co-stimulant for Th1 cytokine production (IFN-γ, IL-2 and granulocyte-macrophage colony stimulating factor) (Izaki, 1978) and also as a co-stimulant for FAS ligand-mediated cytotoxicity of murine natural killer cell clones (Novick et al., 1989).

By cloning IL-18 from affected tissues and studying IL-18 gene expression, a close association of this cytokine with an autoimmune disease was found. The non-obese diabetic (NOD) mouse spontaneously develops autoimmune insulitis and diabetes, which can be accelerated and synchronized by a single injection of cyclophosphamide. IL-18 mRNA was demonstrated by reverse transcriptase PCR in NOD mouse pancreas during early stages of insulitis. Levels of IL-18 mRNA increased rapidly after cyclophosphamide treatment and preceded a rise in IFN-γ mRNA, and subsequently diabetes. Interestingly, these kinetics mimic that of IL-12-p40 mRNA, resulting in a close correlation of individual mRNA levels. Cloning of the IL-18 cDNA from pancreas RNA followed by sequencing revealed identity with the IL-18 sequence cloned from Kupffer cells and in vivo pre-activated macrophages. Also NOD mouse macrophages responded to cyclophosphamide with IL-18 gene expression while macrophages from Balb/c mice treated in parallel did not. Therefore, IL-18 expression is abnormally regulated in autoimmune NOD mice and closely associated with diabetes development (Novick et al., 1992).

IL-18 plays a potential role in immunoregulation or in inflammation by augmenting the functional activity of Fas ligand on Th1 cells (Conti et al., 1997). IL-18 is also expressed in the adrenal cortex and therefore might be a secreted neuro-immunomodulator, playing an important role in orchestrating the immune system following a stressful experience (Chater, 1986).

In vivo, IL-18 is formed by cleavage of pro-IL-18, and its endogenous activity appears to account for IFN-γ production in P. acnes and LPS-mediated lethality. Because of its activity, blocking the biological activity of IL-18 in human disease is a therapeutic strategy in many diseases. This can be accomplished using soluble receptors or blocking antibodies to the cell-bound IL-18 receptor.

Cytokine binding proteins (soluble cytokine receptors) correspond to the extracellular ligand binding domains of their respective cell surface cytokine receptors. They are derived either by alternative splicing of a pre-mRNA, common to the cell surface receptor, or by proteolytic cleavage of the cell surface receptor. Such soluble receptors have been described in the past, including among others, the soluble receptors of IL-6 and IFN-γ (Nakamura et al., 1989), TNF (Dao et al., 1996; Engelmann et al., 1989), IL-1 and IL-4 (John, 1986), IFN-α/β (Mizushima and Nagata, 1990) and others. One cytokine-binding protein, named osteoprotegerin (OPG, also known as osteoclast inhibitory factor—OCIF), a member of the TNFR/Fas family, appears to be the first example of a soluble receptor that exists only as a secreted protein (Anderson, 1997; Bollon, 1980). The present invention deals with soluble IL-18 binding proteins.

Recently, it has been suggested that the interleukin IL-18 is involved in the progression of pathogenicity in chronic inflammatory diseases, including endotoxin shock, hepatitis, and autoimmune-diabetes (Kahiwamura and Okamura, 1998). A further indication of a possible role of IL-18 in the development of liver injury resulted from experiments published by Tsuij et al. (Tsuij et al., 1999), showing an elevated level of IL-18 in lipopolysaccharide-induced acute liver injury in a mouse model. However, the mechanism of the multi-functional factor IL-18 in the development of liver injury has not been elucidated so far.

Liver damage or injury may have diverse causes. It may be due to viral or bacterial infections, alcohol abuse, immunological disorders, or cancer, for example.

Viral hepatitis, due to Hepatitis B virus and Hepatitis C virus, for example, are poorly managed diseases that afflict large number of people worldwide. The number of known hepatitis viruses known is constantly increasing. Apart from Hepatitis B and C virus, at least four other viruses causing virus-associated hepatitis have been discovered so far, called Hepatitis A, D, E and G-Virus.

Alcoholic liver disease is another widespread disease associated with chronic consumption of alcohol. Immune hepatitis is a rare autoimmune disease that is poorly managed. Liver injury also includes damages of the bile ducts. Primary biliary cirrhosis (PBC) is an autoimmune liver disease characterized by destruction of the intrahepatic bile ducts.

Several studies have demonstrated that damage to the liver in diseases such as alcoholic hepatitis, liver cirrhosis, viral hepatitis and primary biliary cirrhosis is associated with T-helper cell-1 (Th1) responses. In one study, a novel liver injury model was established in mice by targeting of ovalbumin-containing liposomes into the liver, followed by adoptive transfer of ovalbumin-specific Th1 cells. Combined treatment of mice with ovalbumin-containing liposomes and Th1 cell transfer caused an increase in serum transaminase activity that was paralleled with an elevation of serum IFN-γ levels. In sharp contrast, ovalbumin-specific Th2 cell transfer resulted in an increase of serum IL-4 levels but did not induce liver injury. The liver injury was blocked by anti-IFN-γ antibodies and anti-tumor necrosis factor (TNF)-α antibodies. These findings indicate that Th1 cells are the major effector cells in acute liver injury (Nishimura and Ohta, 1999) In another set of studies it was shown that mice over-expressing IFN-γ exhibit spontaneous hepatitis without any pathogen or any other stimulant (Okamoto et al., 1998).

Another study implicated Th1 responses in primary biliary cirrhosis (PBC). PBC is an autoimmune liver disease characterized by destruction of the intrahepatic bile ducts. It is generally believed that cellular immune mechanisms, particularly involving T cells, result in this bile duct damage. The relative strength of Th1 and Th2 responses has recently been proposed to be an important factor in the pathophysiology of various autoimmune diseases. In this study, the The subset balance in PBC was evaluated by detection of cytokines specific to the two T-cell subsets, i.e., IFN-γ for Th1 cells and IL-4 for Th2 cells. IFN-γ and IL-4 messenger RNA (mRNA) positive cells were counted in liver sections from 18 patients with PBC and 35 disease controls including chronic active hepatitis C, extrahepatic biliary obstruction, and normal liver, using nonisotopic in situ hybridization and immunohistochemistry. Mononuclear cells expressing IFN-γ and IL-4 mRNA were aggregated in inflamed portal tracts in PBC livers, but were rarely present in extrahepatic biliary obstruction, alcoholic fibrosis, or normal liver sections. The IFN-γ and IL-4 mRNA positive cells in PBC livers were detected in significantly higher numbers than in control livers (P<0.01). Moreover, IFN-γ mRNA expression was more commonly detected than IL-4 expression in PBC livers, and the levels of IFN-γ mRNA expression were highly correlated with the degree of portal inflammatory activity. IFN-γ mRNA-positive cells were detected primarily around damaged bile ducts that were surrounded by lymphoid aggregates. The data indicate that Th1 cells are the more prominent T-cell subset in the lymphoid infiltrates in PBC (Harada et al., 1997).

The cytokine pattern on viral antigen recognition is also believed to exert a profound influence on the resolution of viral infections and viral clearance. One study investigated whether a cytokine imbalance oriented toward Th2 type response plays a role in chronic hepatitis B. Cytokine profiles of peripheral blood mononuclear cells associated with chronic hepatitis B were analyzed by RT-PCR. Upon hepatitis B surface antigen (HbsAg) stimulation, expression of IFN-γ, IL-2, IL-4, and IL-10 was detected in 41%, 8%, 41%, and 50% of the patients, respectively. Among these cytokines, the expression of the Th1 cytokine IFN-γ was associated with high levels of serum AST/ALT (Aspartate aminotransferase/ Alanine aminotransferase), representing typical markers of liver damage. Th2 type cytokines were not shown to exert a protective effect on hepatocytes. In conclusion, production of a Th1 cytokine, IFN-γ, by HBsAg-reactive cells was associated with hepatocyte damage in chronic hepatitis B (Lee et al., 1999). High levels of the FAS ligand and its receptor (CD95) were reported in liver of hepatitis B patients (Luo et al., 1997). FAS ligand is considered to be one of the major cytotoxic agents leading to hepatocyte apoptosis.

Another study identified factors associated with the progression of liver injury in 30 hepatitis C virus/RNA (HCV/RNA)-positive untreated patients with chronic hepatitis. Necroinflammatory and architectural damage were evaluated using Ishak's score. Activated hepatic stellate cells (HSC) were visualized by immunohistochemistry for α-smooth muscle actin (αSMA) and quantitated by morphometry. Plasma HCV/RNA was evaluated using a competitive RT-PCR method. To study the type of immune response involved in the progression of liver injury, IFN-γ-positive cells (as expression of a Th1-like response) were evaluated by immunohistochemistry and quantitated by morphometry. It was found that HSC were mostly detected close to areas of lobular necroinflammation or lining fibrotic septa. The αSMA- and Sirius Red-positive parenchyma correlated significantly with necroinflammatory and architectural scores. IFNγ-positive cells were detected in periportal areas associated with the inflammatory infiltrates and significantly correlated with architectural damage. It was therefore concluded that HSC activation and progression of liver injury are associated with a Th1-like response (Baroni et al, 1999). Similarly to the case of Hepatitis B, FAS ligand and its receptor were found in liver and sera of hepatitis C patients (Hiramatsu et al, 1994; Okazaki et al, 1996; Lio et al., 1998)

Th1 cytokines and other Th1 markers were found to be associated with alcoholic hepatitis and liver cirrhosis. Inflammatory stimuli and lipid peroxidation activate nuclear factor κ B (NF-κB) and upregulate proinflammatory cytokines and chemokines. In one study, the relationship between pathological liver injury, endotoxemia, lipid peroxidation, and NF-κB activation and imbalance between pro- and anti-inflammatory cytokines was evaluated. Rats (5 per group) were fed ethanol and a diet containing saturated fat, palm oil, corn oil, or fish oil by intragastric infusion. Dextrose isocalorically replaced ethanol in control rats. Pathological analysis was performed and measurements of endotoxin were taken, lipid peroxidation, NF-κB, and messenger RNA (mRNA) levels of proinflammatory cytokines (TNFα, IL-1beta, IFN-γ, and IL-12), C-C chemokines (regulated upon activation, normal T cell expressed and secreted [RANTES], monocyte chemotactic protein [MCP]-1, macrophage inflammatory protein [MIP]-1-α), C—X—C chemokines (cytokine induced neutrophil chemoattractant [CINC], MIP-2, IP-10, and epithelial neutrophil activating protein [ENA]-78), and anti-inflammatory cytokines (IL-10, IL-4, and IL-13). Activation of NF-κB and increased expression of proinflammatory cytokines C—C and C—X—C chemokines was seen in the rats exhibiting necroinflammatory injury (fish oil-ethanol and corn oil-ethanol). These groups also had the highest levels of endotoxin and lipid peroxidation. Levels of IL-10 and IL-4 mRNA were lower in the group exhibiting inflammatory liver injury. Thus, activation of NF-κB occurs in the presence of proinflammatory stimuli and results in increased expression of Th1 proinflammatory cytokines and chemokines (Naji et al., 1999). FAS ligand and its receptor are also elevated in alcoholic liver diseases, suggesting once again that Th1 cytokines are involved in the autoimmune processes induced in alcoholic hepatitis (Galle et al., 1995; Taieb et al, 1998; Fiore et al., 1999).

TNF-α has also emerged as a common pathway in the pathogenesis of alcohol-related hepatic necro-inflammation. Increased levels of hepatic and serum TNF have been documented in animal models of alcoholic liver disease and in human alcoholic liver disease. This dysregulated TNF metabolism has been postulated to play a role in many of the metabolic complications and the liver injury of alcoholic liver disease (Grove et al., 1997; McClain and Cohen, 1989). For instance it was found in one study that patients with alcoholic hepatitis had higher TNF-α levels (mean, 26.3 ng/L; 95% Cl, 21.7 to 30.9) than normal subjects (6.4 ng/L; Cl, 5.4 to 7.4). Patients who subsequently died had a higher TNF-α level (34.7 ng/L; Cl, 27.8 to 41.6) than survivors (16.6 ng/L; Cl, 14.0 to 19.2). In patients with alcoholic hepatitis, TNF-α levels correlated positively with serum bilirubin (r =0.74; P =0.0009) and serum creatinine (r=0.81; P=0.0003). Patients with alcoholic hepatitis had higher TNF-α levels than patients with inactive alcoholic cirrhosis (11.1 ng/L; Cl, 8.9 to 13.3) and severely alcoholic persons without liver disease (6.4 ng/L; Cl, 5.0 to 7.8). Patients with abnormal renal function had lower TNF-α levels (14.1 ng/L; Cl, 5.4 to 22.8) than patients with alcoholic hepatitis. It was therefore concluded that elevations in TNF-α in alcoholic hepatitis are most marked in severe cases, suggesting that TNF-α plays a role in the pathogenesis (Bird et al., 1990)

TNF mediates many of the biologic actions of endotoxin. Recent studies have shown that TNF administration may cause liver injury and that TNF may mediate the lethality of the hepatotoxin galactosamine. One of the most potent TNF inducers is endotoxin. Because patients with alcoholic liver disease frequently have endotoxemia and because many of the clinical manifestations of alcoholic hepatitis are known biologic actions of TNF, its activity was evaluated in patients with alcoholic hepatitis. Basal and lipopolysaccharide-stimulated TNF release from peripheral blood monocytes, a major source of TNF production, was determined in 16 patients with alcoholic hepatitis and 16 healthy volunteers. Eight of 16 alcoholic hepatitis patients and only two of 16 healthy volunteers had detectable spontaneous TNF activity (p less than 0.05). After lipopolysaccharide stimulation, mean monocyte TNF release from alcoholic hepatitis patients was significantly increased to over twice that of healthy controls (25.3+/−3.7 vs. 10.9+/−2.4 units per ml, p less than 0.005). It was therefore concluded that monocytes from alcoholic hepatitis patients have significantly increased spontaneous and lipopolysaccharide-stimulated TNF release compared to monocytes from healthy volunteers (McClain and Cohen, 1989.

Lipopolysaccharide (LPS)-binding protein (LBP) and CD14 play key intermediary roles in the activation of cells by endotoxin. Gut-derived LPS has been postulated to participate in promoting pathological liver injury in alcoholic liver disease. It was demonstrated that rats fed intragastrically with ethanol in oil for 4 weeks had elevated levels of CD14 and LBP in their Kupffer cells and hepatocytes, respectively. Expression of CD14 mRNA was also elevated in nonmyeloid cells. Enhanced LBP and CD14 expression rapidly increases the LPS-induced expression of various pro-inflammatory cytokines and correlates with the presence of pathological liver injury in alcoholic liver injury (Su et al., 1998; Lukkari et al., 1999).

IL-6 is a 26 kd cytokine that plays a major role in the acute phase response, especially the hepatic aspects of the acute phase response. Patients with alcoholic hepatitis manifest many aspects of the acute phase response. Serial plasma IL-6 levels in 30 consecutive patients with moderate to severe alcoholic hepatitis was measured during 6 month. Mean admission plasma IL-6 activity was markedly increased (49.8+/−8.5 U/ml, normal less than 5 U/ml) in patients with alcoholic hepatitis, and levels decreased with clinical improvement to 15.6+/−6.1 U/ml at 6 months. Admission IL-6 activity correlated significantly (r=0.82) with the severity of liver disease as assessed by the discriminant function of Maddrey. IL-6 activity fell over time in a pattern similar to that of bilirubin and C-reactive protein. This and additional studies suggest that plasma IL-6 is probably a marker of inflammation and severity of disease in alcoholic hepatitis (Sheron et al., 1991; Hill et al., 1992).

IL-8, a cytokine produced by a number of cells, including monocytes, macrophages, Kupffer cells and hepatocytes, can activate neutrophils. Peripheral neutrophilia and liver neutrophil infiltration are frequently noted in patients with alcoholic liver disease. It was found that serum IL-8 levels were markedly elevated in patients with alcoholic hepatitis (437+/−51 pg/ml) when compared to all other groups (p<0.05). Levels of IL-8 in patients with alcoholic fatty liver, alcoholic cirrhosis and viral hepatitis were higher than those in controls and in patients with non-alcoholic fatty liver. In addition, IL-8 levels were higher in patients who died (p=0.007), and correlated with biochemical and histological parameters, and severity of liver injury: serum aspartate aminotransferase, alanine aminotransferase, total bilirubin, prothrombin time, indocyanine green retention ratio, TNF-α and peripheral neutrophil count in patients with alcoholic hepatitis. After a 2-year follow up, patients with IL-8 above 479 pg/ml had a higher mortality rate in the alcoholic hepatitis group (p=0.033). These findings suggest that IL-8 as well as some other chemokines are activated in alcoholic liver disease, especially in alcoholic hepatitis, and is closely correlated with liver injury (Martinez et al., 1992; Hill et al., 1992).

Induction of adhesion molecules such as ICAM-1 is associated with the activation and attraction of a special population of inflammatory cells characteristic for alcoholic hepatitis. Frozen liver samples from patients who died with signs of acute alcoholic hepatitis show elevated ICAM-1 expression in the membranes of hepatocytes, as well as the occurrence of CD1 1b positive polymorphonuclear leukocytes (neutrophils) suggesting a possible major role of the beta 2-integrin Mac-1 as a ligand for ICAM-1. It was concluded that in alcoholic hepatitis cytokines may be responsible for the induction of the adhesion molecule ICAM-1 on hepatocytic membranes and activate a defined population of inflammatory cells, thus contributing to the characteristic histological picture of acute alcoholic hepatitis with its concentration of neutrophils especially in areas with ballooned Mallory body-containing hepatocytes (Afford et al., 1998).

A significant increase in both NK cells (CD3−/CD56+) and the cytotoxic T cells coexpressing the CD3 and the CD56 molecules together with an increased NK cytotoxic activity were observed in patients having alcoholic hepatitis. Interestingly these abnormalities persisted during the withdrawal period (Ohlinger et al., 1993).

Arthritis is a disease involving joint inflammation. The joints show swelling, stiffness, tenderness, redness or warmth. The symptoms may be accompanied by weight loss, fever or weakness. When these symptoms last for more than two weeks, inflammatory arthritis e.g. rheumatoid arthritis may be the cause. Joint inflammation may also be caused by infection, which can lead to septic arthritis. A very common type of arthritis is degenerative joint disease (osteoarthritis). Joint inflammation is not a prominent feature of osteoarthritis.

The medicaments commonly prescribed for arthritis and related conditions are non-steroidal anti-inflammatory drugs (NSAIDs). NSAIDs include aspirin and aspirin-like drugs. They reduce inflammation, which is the cause for joint pain, stiffness and swelling of the joints. However, NSAIDs are unspecific drugs having a number of side effects, involving bleeding of the stomach (Homepage of the Department of Orthopaedics of the University of Washington on Arthritis, Frederick Matsen (Chairman). In addition to NSAIDs, Celebrex™, a cyclooxygenase (COX-2) inhibitor, is used to relieve the signs and symptoms of osteoarthritis and rheumatoid arthritis in adults. It is also indicated for the treatment of patients with familial adenomatous polyposis.

Further, TNF antagonists are used for the treatment of arthritis. TNF antagonists are described, for example, in WO 9103553.

Recent studies indicate that the interleukin IL-18 plays a proinflammatory role in joint metabolism. Olee et al. (1999) showed that IL-18 is produced by articular chondrocytes and induces proinflammatory and catabolic responses. The IL-18 mRNA was induced by IL-1β in chondrocytes. Chondrocytes produced the IL-18 precursor and in response to IL-1 stimulation secreted the mature form of IL-18. Studies on IL-18 effects on chondrocytes further showed that it inhibits TGF-β-induced proliferation and enhances nitric oxide production. IL-18 stimulated the expression of several genes in normal human articular chondrocytes including inducible nitric oxide synthase, inducible cyclooxygenase, IL-6, and stromelysin. Gene expression was associated with the synthesis of the corresponding proteins. Treatment of normal human articular cartilage with IL-18 increased the release of glycosaminoglycans. These finding identified IL-18 as a cytokine that regulates chondrocyte responses and contributes to cartilage degradation.

The localisation of Interleukin-1β-converting enzyme (ICE)/caspase-1 in human osteoarthritic tissues and its role in the maturation of interleukin-1beta and interleukin-18 have been shown by Saha et al. (1999). Saha et al. studied the expression and production of caspase-1 in human normal and osteoarthritic (OA) cartilage and synovium, quantitated the level of ICE in OA chondrocytes, and examined the relationship between the topographic distribution of ICE, interleukin-1β (IL-1β), and IL-18, as well as apoptosis of chondrocytes. The experiments performed in this study indicated that ICE was expressed and synthesised in both human synovial membrane and cartilage, with a significantly greater number of cells staining positive in OA tissue than in normal tissue. ICE production was preferentially located in the superficial and upper intermediate layers of articular cartilage. The production of mature IL-1beta in OA cartilage explants and chondrocytes was completely blocked by treatment with a specific ICE inhibitor, which also markedly diminished the number of IL-18-positive cells. The relationship between active IL-1beta and ICE suggests that ICE may promote OA progression by activating this proinflammatory cytokine, and that IL-18 may play a role in cartilage pathology.

Gracie et al. (1999) suggested a proinflammatory role for IL-18 in rheumatoid arthritis. Gracie et al. detected the IL-18 mRNA and protein within rheumatoid arthritis synovial tissues in significantly higher levels than in osteoarthritis controls. It was also shown that a combination of IL-12 or IL-15 with IL-18 induced the IFN-γ production by synovial tissues in vitro. Furthermore, IL-18 administration of collagen/inclomplete Freund's adjuvant-immunized mice facilitated the development of an erosive, inflammatory arthritis, suggesting that IL-18 may be proinflammatory in vivo.

However, so far, apart from chemical compounds, only the blockade of TNFα and IL-1β by using soluble receptors or monoclonal antibodies have been shown to decrease murine collagen-induced arthritis (CIA, which is a mouse model for rheumatoid arthritis) (Williams et al., 1994), and were therefore suggested as a therapeutic for rheumatoid arthritis.

Dayer (1999) summarized the different and partially contradicting functions of IL-18. IL-18 is a pleiotropic interleukin having both inflammatory enhancing and attenuating functions. On the one hand, it enhances production of the proinflammatory cytokines like TNFα, therefore promoting inflammation. On the other hand, it induces the production of NO, an inhibitor of caspase-1, thus blocking the maturation of IL-1β and IL-18, and possibly attenuating inflammation. This ambiguous role of IL-18 seriously questioned the efficacy of IL-18 inhibitors in inflammatory diseases. Furthermore, because of the interaction of a huge variety of different cytokines and chemokines in the regulation of inflammation, it could not have been expected to obtain a beneficial effect by blocking only one of the players in such a complicated scenario.

SUMMARY OF THE INVENTION

The present invention provides IL-18 binding proteins (IL-18BPs) and virally encoded IL-18BP homologues (hereinafter, viral IL-18BPs), and fused proteins, muteins, functional derivatives and active fragments thereof, capable of binding to IL-18. The invention also provides a process for obtaining IL-18BPs by isolating them from human fluids to obtain IL-18BP, or by recombinant means, which also allows for attainment of the various IL-18BPs. The invention also provides expression vectors of IL-18BPs, suitable for expression of IL-18BP in humans and other mammals. The IL-18BPs and the expression vectors of the present invention are useful for blocking the biological activities of IL-18.

Replicable expression vehicles containing DNAs suitable for expression of the various IL-18BPs in host cells, host cells transformed herewith and proteins and polypeptides produced by expression of such hosts are also provided.

The invention further provides antibodies to the IL-18BPs and the viral IL-18BPs, suitable for affinity purification and immunoassays of same.

The invention further provides pharmaceutical compositions consisting of suitable vehicles and IL-18BPs, or viral IL-18BPs, or vectors for expressing same in humans and other mammals, for the treatment of diseases or conditions which require modulation of IL-18 activity.

These diseases or conditions include autoimmune diseases, type I diabetes, rheumatoid arthritis, graft rejections, inflammatory bowel disease, sepsis, multiple sclerosis, ischemic heart diseases (including heart attacks), ischemic brain injury, chronic hepatitis, psoriasis, chronic pancreatitis, acute pancreatitis and the like.

It is a specific object of the present invention to provide for a novel means for treating and/or preventing liver injury. It has been found that an IL-18 inhibitor is effective in the prevention and treatment of liver damages. The invention therefore also relates to the use of an IL-18 inhibitor for the manufacture of a medicament for treatment and/or prevention of liver injury. More specifically, the invention relates to the treatment and/or prevention of liver injuries caused by alcoholic hepatitis, viral hepatitis, immune hepatitis, fulminant hepatitis, liver cirrhosis, and primary biliary cirrhosis.

It has also been found in accordance with the present invention that an inhibitor of IL-18 is effective in the therapy of arthritis. The therapeutic effect includes decreasing the severity of the disease, as well as preventing the spreading of the disease. The invention therefore relates to the use of an inhibitor of IL-18 for treatment and/or prevention of arthritis. This finding is unexpected, since from the state of the art outlined above, it could not have been concluded that a blockade of one specific factor involved in arthritis, namely interleukin IL-18, would lead to the alleviation of arthritis or even the curing of a diseased arthritic joint.

It has also been found that the administration of an IL-18 inhibitor significantly diminishes cartilage erosion in a murine model of arthritis. The present invention thus also relates to the use of an inhibitor of IL-18 in the manufacture of a medicament for treatment and/or prevention of cartilage destruction.

In order to apply a gene therapeutical approach to deliver the IL-18 inhibitor to the diseased tissue or cell, it is a further object of the invention to use an expression vector comprising the coding sequence of an IL-18 inhibitor for the treatment and/or prevention of arthritis.

SF=Sigma-Frankel: 1 SF Unit of AST/ALT will form 4.82× $10^{-4}$ μmol glutamate/minute at pH 7.5 at 25° C.

Figure 7:
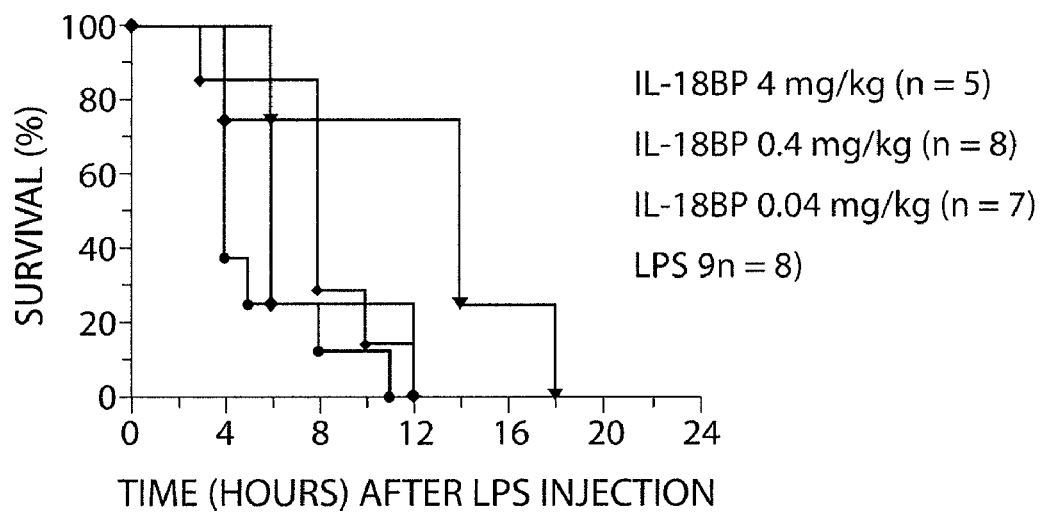

FIG. 7 shows the survival time of the mice after LPS injection. Mice were injected with different doses of recombinant human IL18BP (0; 0.04; 0.004; 4 mg/kg) 20 min before injection of LPS into P. acnes sensitized mice. Triangles: 4 mg/kg; small diamond: 0.4; big diamond: 0.04; circles: no IL18BP (only LPS).

Figure 8:
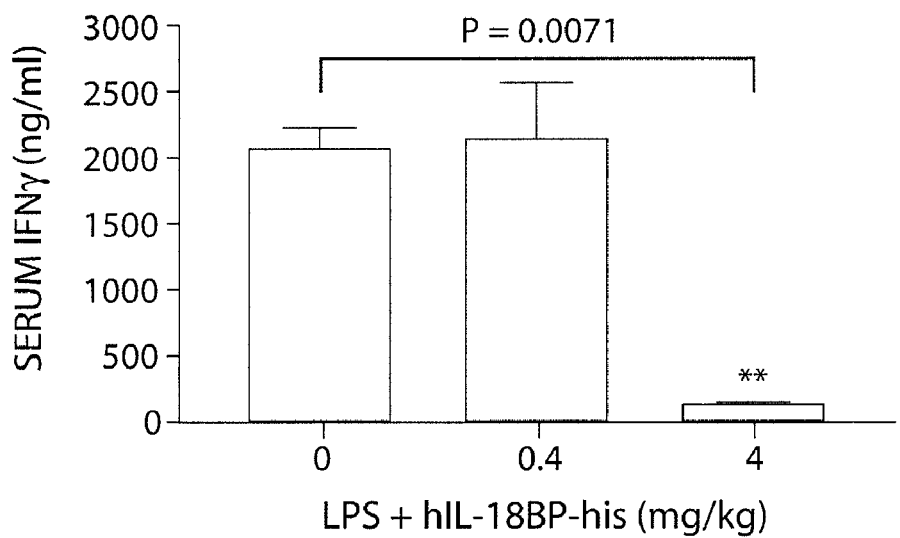

FIG. 8 shows a histogram depicting serum levels of IFN-γ, measured 5 h after injection of different amounts of IL18BP (0; 0.4; 4 mg/kg), which was administered 20 min before LPS injection into P. acnes sensitized mice.

Figure 9A:
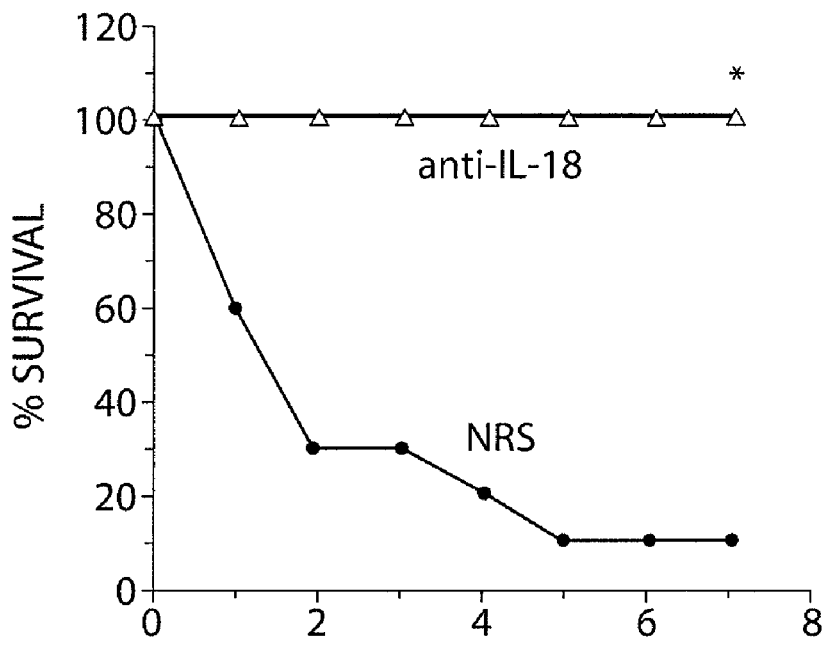
Figure 9B:
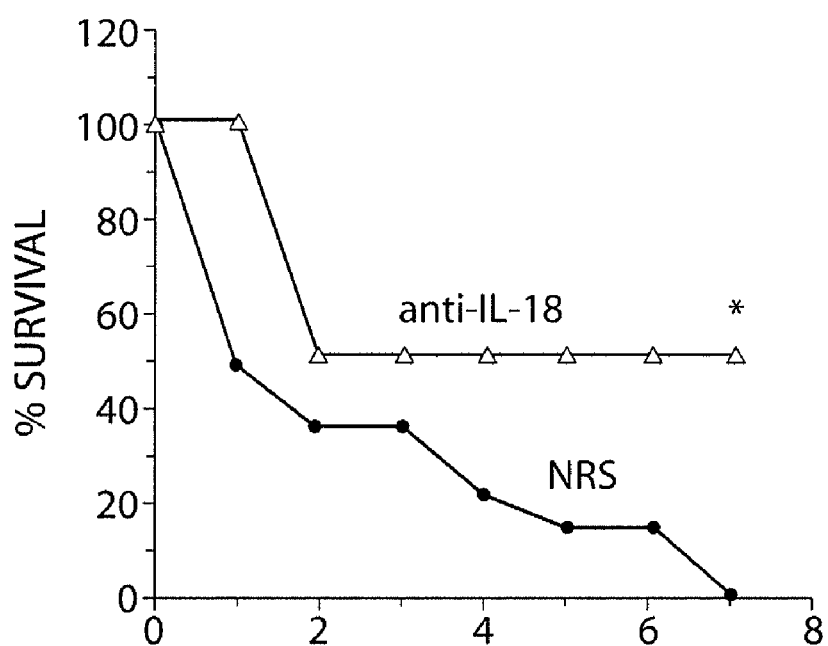

FIG. 9 shows the survival of mice injected either with polyclonal IL-18 antiserum or normal rabbit serum (NDS=control) 30 min before injection with 40 mg/ml (lethal dosis) of LPS derived from E. coli (FIG. 9A) or S. thyphimurium (FIG. 9B). Triangles: mice were injected with IL-18 antiserum; circles: mice were injected with NDS. On the x-axis, the days after LPS challenge are depicted. * p<0,05.

Figure 10A:
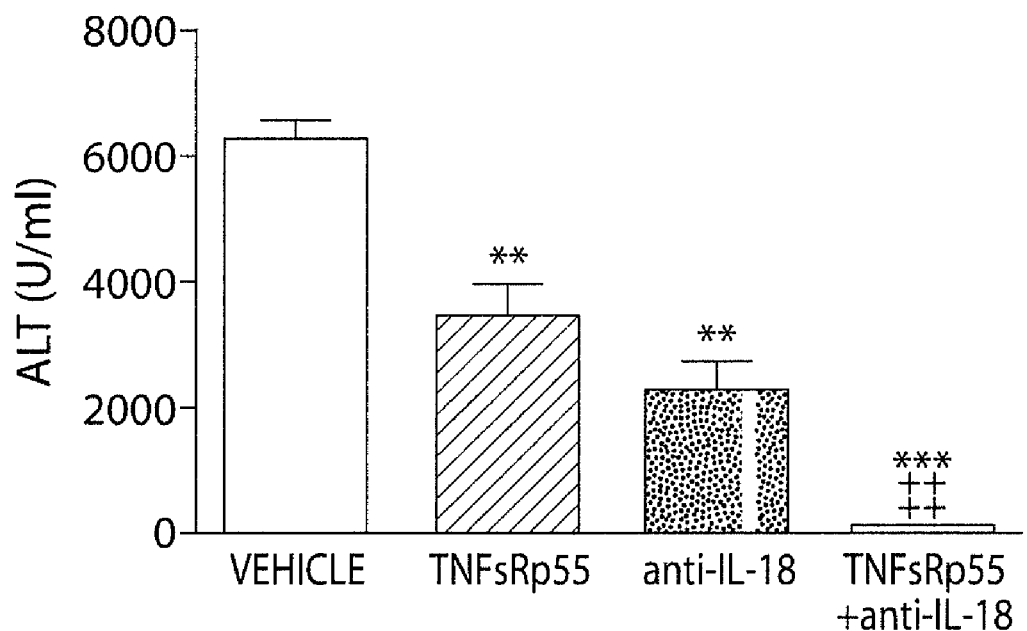
Figure 10B:
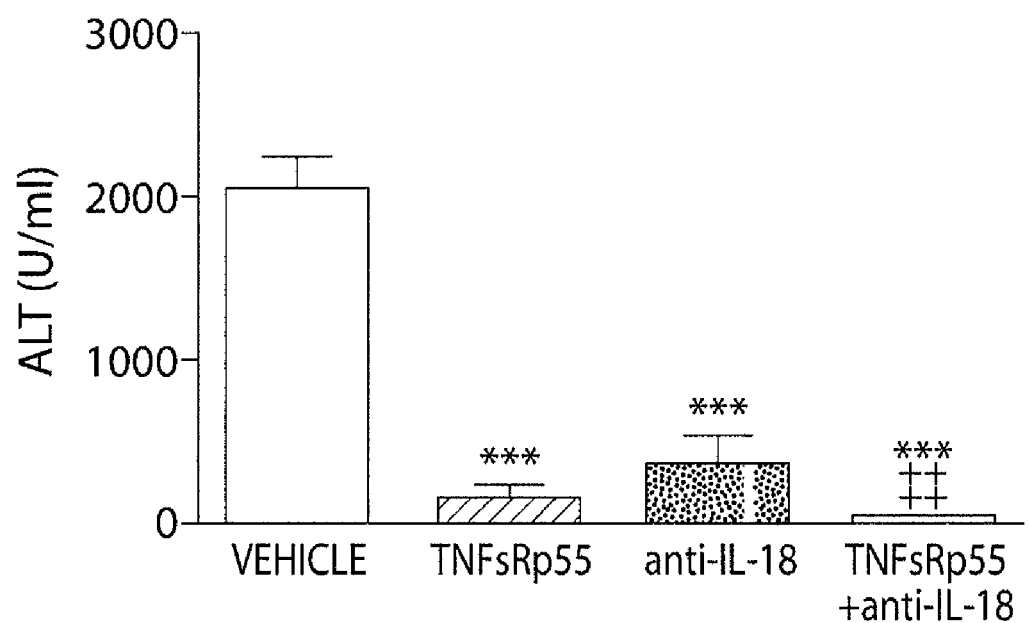

FIG. 10 shows a histogram, in which the mean+SEM of five mice per group treated in the following way are depicted. Mice were injected intraperitoneally (i.p.) either anti-IL-18 antiserum, soluble TNF-α receptors (TNFsRp55) or vehicle (saline), immediately followed by the intravenous (i.v.) administration of Concanavalin A (Con A; FIG. 10A) or PEA (Pseudomonas aeruginosa, FIG. 10B). p<0.01; *p<0.001 vs ConA or PEA alone; # p<0.01 vs either TNF-sRp55 or anti-IL-18 factorial ANOVA.

Figure 11A:
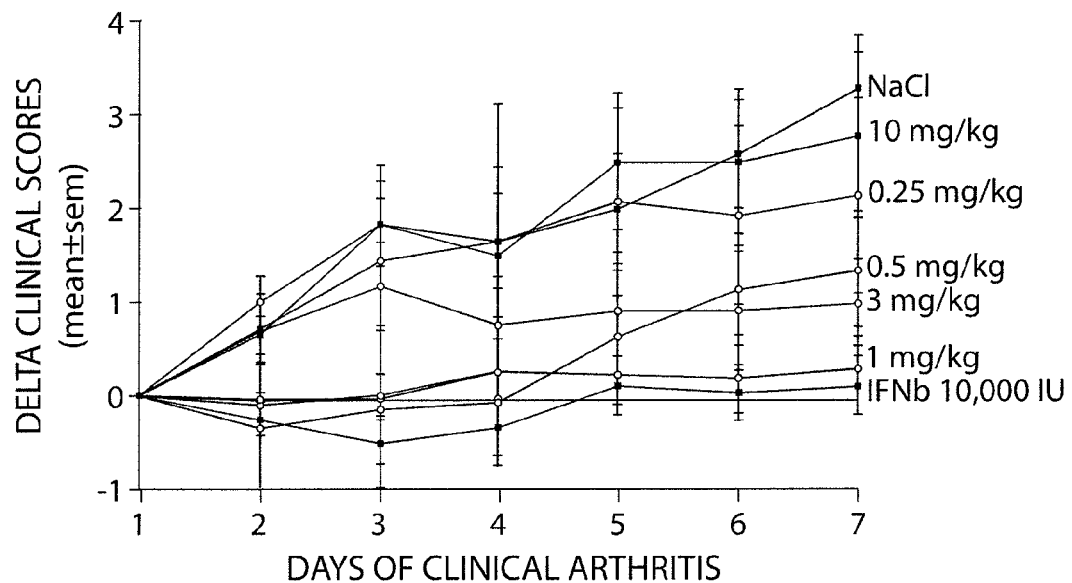
Figure 11B:
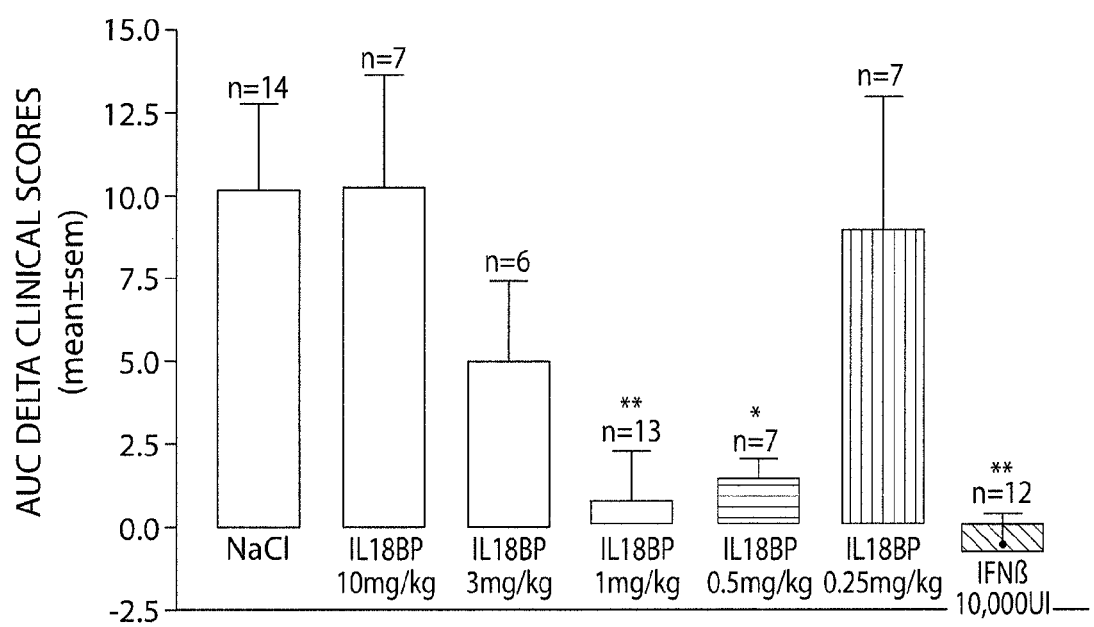

FIG. 11 shows the effect of of IL-18BP on clinical scores in a murine model of arthritis
 (A) shows a diagram depicting the clinical scores measured after daily administration of different amounts of IL-18BP or IFN-P or vehicle (NaCl) i.p. (intraperitoneally) to mice. Symbols: Filled triangles: 10 000 IU IFN-β; open triangles: 10 mg/kg IL-18BP, reversed triangles: 3 mg/kg IL-18BP, diamonds: 1 mg/kg IL-18BP; circles: 0.5 mg/kg IL-18BP; open squares: 0.25 mg/kg IL-18BP, and filled squares: NaCl. The days of treatment are depicted on the x-axis, the clinical scores (mean values) are depicted on the y-axis. Statistics were calculated by the Mann Whitney test.
 (B) shows a histogram depicting the AUC (area under the curve) derived from the graph of FIG. 11. n=number of animals.

FIG. 12 shows the effect of IL-18BP on paw swelling
 (A) shows a diagram depicting the results obtained by measuring the paw thickness (swelling) of diseased hind paws of individual animals treated with different amounts of IL-18BP. The y-axis shows the change of paw thickness in millimeters from the beginning of treatment. The symbols are as in FIG. 11.
 (B) shows a histogram depicting the AUC derived from FIG. 11A. n=number of animals.

Figure 13:
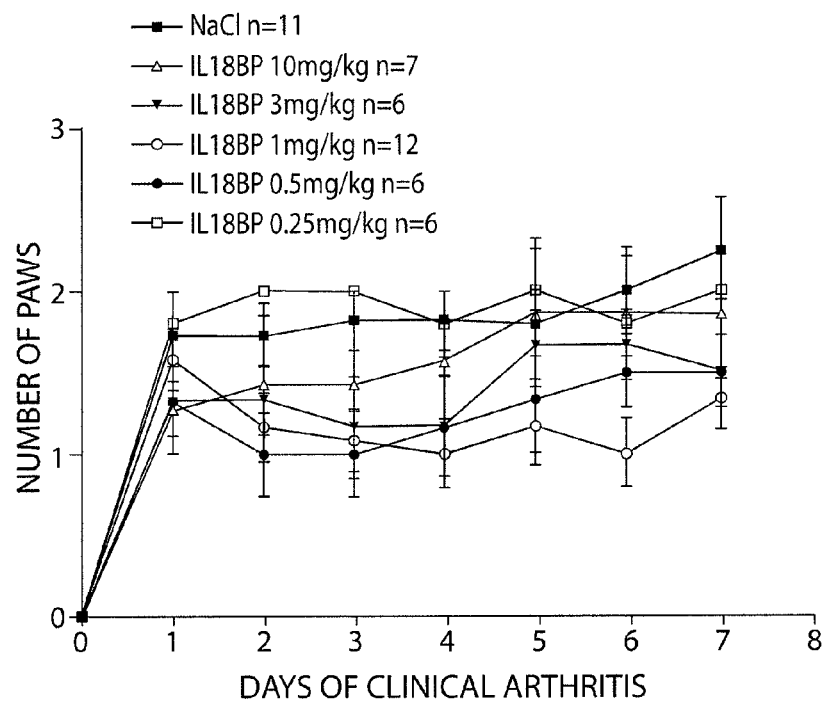

FIG. 13 shows the analysis of the number of diseased hind paws at the time of acute arthritis, i.e. spreading of the disease to additional joints. Symbols: Filled squares: NaCl (control), triangles: 10 mg/kg IL-18BP, reversed triangles: 3 mg/kg IL-18BP, diamonds: 1 mg/kg IL-18BP, circles: 0.5 mg/kg IL-18BP and open squares: 0.25 mg/kg IL-18BP.

Figure 14:
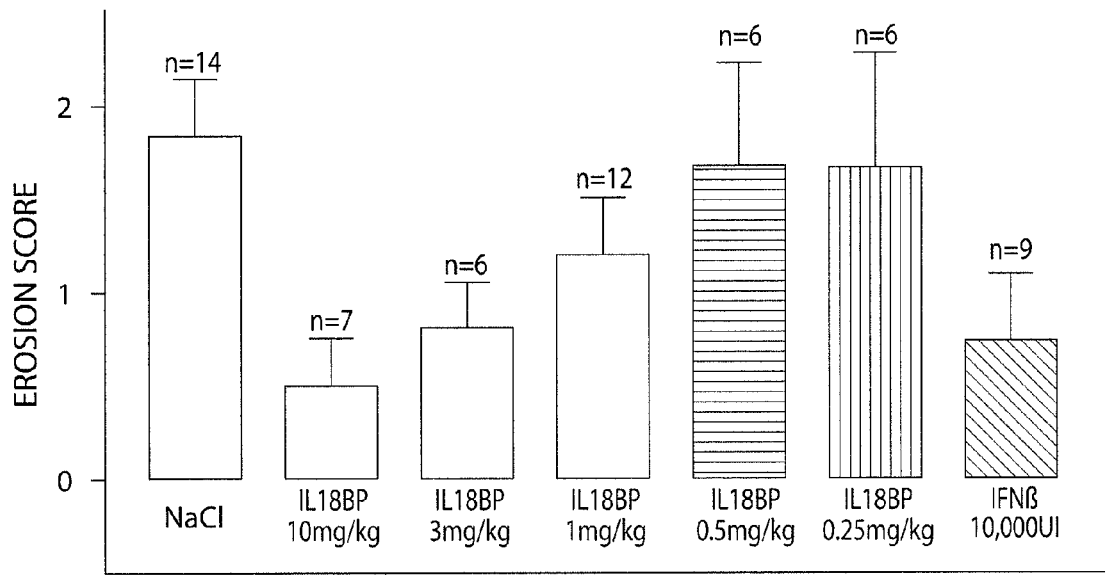

FIG. 14 shows a histogram depicting the erosion scores of the cartilage of diseased joints.

Figure 15A:
Figure 15B:
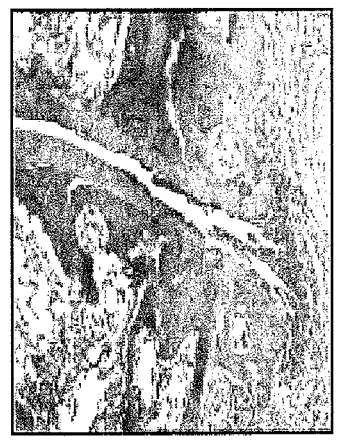
Figure 15C:

FIG. 15 shows the histopathology of mouse joints. At the end of the experiment, the paw that first developed arthritis was dissected away, fixed and processed as described in Example 2 below. A) normal mouse joint; B) joint from an arthritic mouse; C) joint from a mouse treated with rhIL-18BP.

Figure 16:
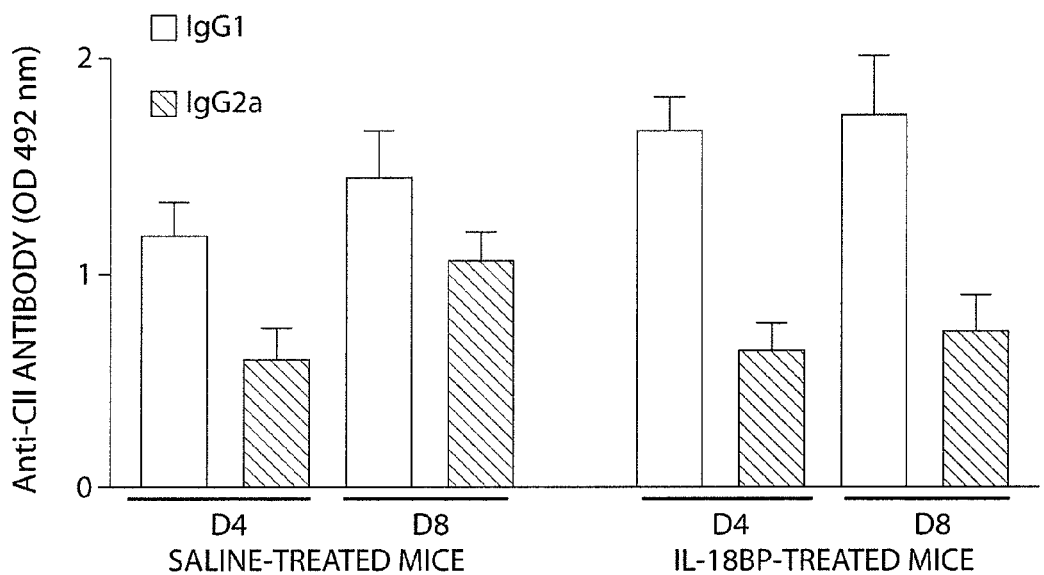

FIG. 16 shows a histogram depicting the levels of anti-collagen type II antibodies of the isotype IgG1 (open columns) or IgG2a (hatched columns) of mice treated with 3 mg/kg of IL-18BP or saline (vehicle), respectively. Measurements were taken on day 4 (D4) or day 8 (D8) of the disease.

Figure 17:
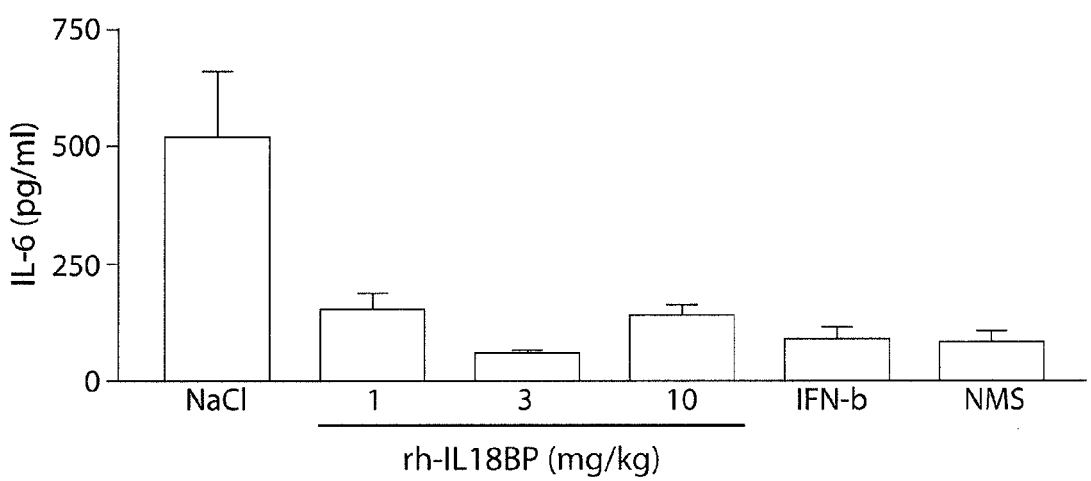

FIG. 17 shows a histogram depicting IL-6 levels in pg/ml of animals treated with 1, 3 or 10 mg/kg of IL-18BP, 10 000 IU of Interferon β (IFN-b), normal mouse serum (NMS) or saline (NaCl), respectively.

DETAILED DESCRIPTION OF THE INVENTION

The present invention relates to various IL-18BPs and viral IL-18BPs which bind to IL-18 and thus, are capable of blocking the biological activities of IL-18. The term, "IL-18BPs and viral IL-18BPs," includes muteins of IL-18BPs and viral IL-18BPs, derivatives of IL-18BPs and viral IL-18BPs and truncated forms of IL-18BPs and viral IL-18BPs and salts thereof. The invention further relates to replicable expression vehicles, suitable for expression of various IL-18BPs or viral IL-18BPs in host cells and host bacteria. The invention further relates to expression vectors, suitable for expression of various IL-18BPs or viral IL-18BPs in humans and in other mammals.

The replicable expression vehicles containing DNAs suitable for expression of various IL-18BPs and viral IL-18BPs in host cells, according to the invention, may be PCR products, cDNA, synthetic DNA and combinations thereof. DNA molecules hybridizing to the above DNAs under stringent conditions and encoding proteins or polypeptides having the same activity as IL-18BP are also included in the present invention.

The expression vectors, suitable for expression of various IL-18BPs or viral IL-18BPs in humans and in other mammals, according to the present invention, may be viral vectors or other types of vectors to which an IL-18BP gene or an IL-18BP cDNA or a DNA encoding a viral IL-18BP was inserted in a way that enables efficient expression of an IL-18BP or a viral IL-18BP in humans and other mammals. DNA molecules hybridizing to the above DNAs under stringent conditions and encoding proteins or polypeptides having the same activity as IL-18BP, are also included in the present invention.

Isolation of IL-18BP may be accomplished in accordance with the invention, e.g. by passing a human fluid, such as urine or serum, through a chromatographic column to which IL-18 is coupled, and thereafter, eluting the bound IL-18BP.

The various IL-18BPs and viral IL-18BPs can also be prepared by recombinant means, i.e. by expressing IL-18BP in a suitable host, after adding promoters, expression enhancers, etc., suitable for the particular host employed.

The various IL-18BPs and viral IL-18BPs and vectors for expressing IL-18Bp in humans and other mammals may be employed in the treatment and alleviation of conditions in which IL-18 is involved or caused by an excess of exogenously administered or endogenously produced IL-18. Such conditions are, e.g., autoimmune diseases, type I diabetes, rheumatoid arthritis, graft rejections, inflammatory bowel disease, sepsis, multiple sclerosis, ischemic heart diseases (including heart attacks), ischemic brain injury, chronic hepatitis, psoriasis, chronic pancreatitis, acute pancreatitis and the like.

Figure 1:
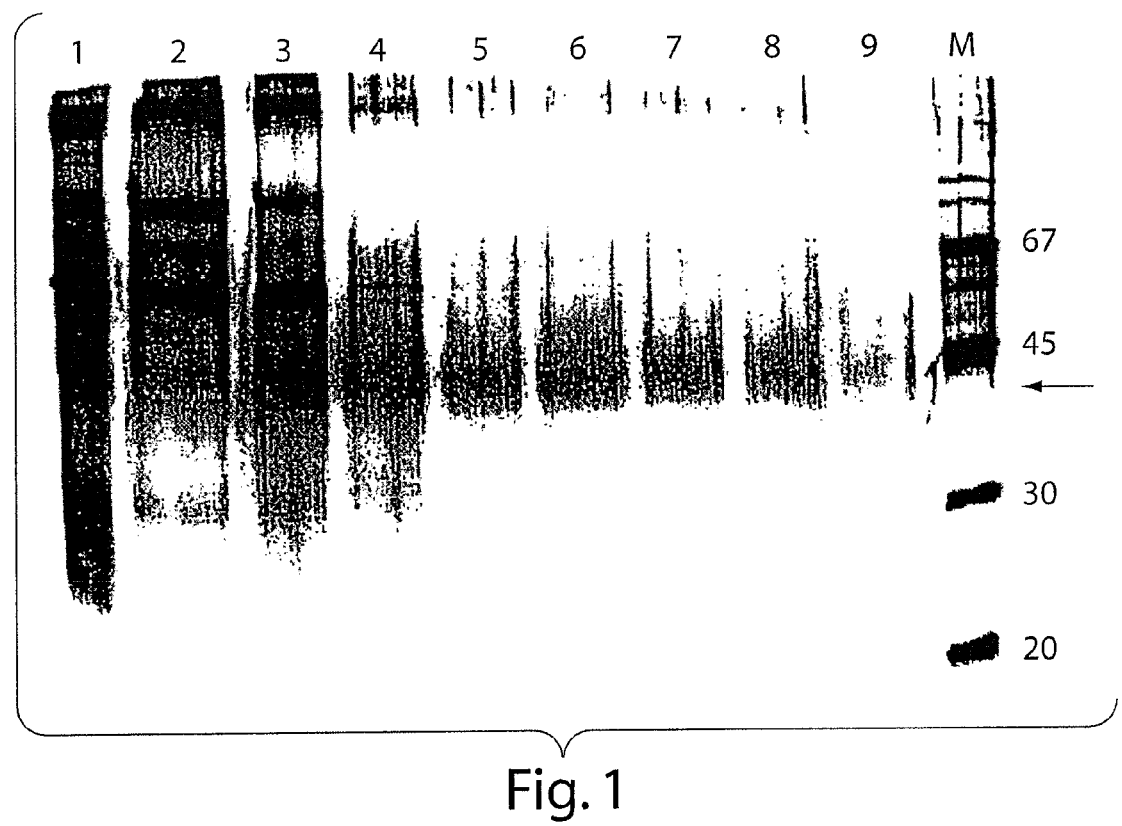
FIG. 1 shows SDS-PAGE (sodium dodecyl sulfate polyacrylamide gel electrophoresis) of ligand affinity purified IL-18 binding protein. Crude urinary proteins (concentrated by ultrafiltration of 500 L normal human urine) were loaded on an IL-18-agarose column. The column was washed and bound proteins eluted at pH 2.2. Eluted fractions were neutralized and aliquots were analyzed by SDS-PAGE (10% acrylamide) under non-reducing conditions and silver staining. The lanes are: 1: crude urinary proteins (1.5 μg, loaded on the gel); 2-9: elutions 1-8, respectively, from the IL-18-agarose column; 10: molecular weight markers, in kD, as indicated on the right side. An arrow indicates the band corresponding to IL-18BP.

According to the present invention, IL-18BP was isolated from normal human urine by one chromatographic step. A preparation of crude human urinary proteins was loaded on a column consisting of human IL-18 bound to agarose. The column was washed and bound proteins were eluted at low pH. Eluted fractions were neutralized and aliquots were analyzed by SDS-PAGE (10% acrylamide) under non-reducing conditions and silver staining. A protein band of ~40 kD was specifically obtained in the eluted fractions (FIG. 1).

Figure 2:
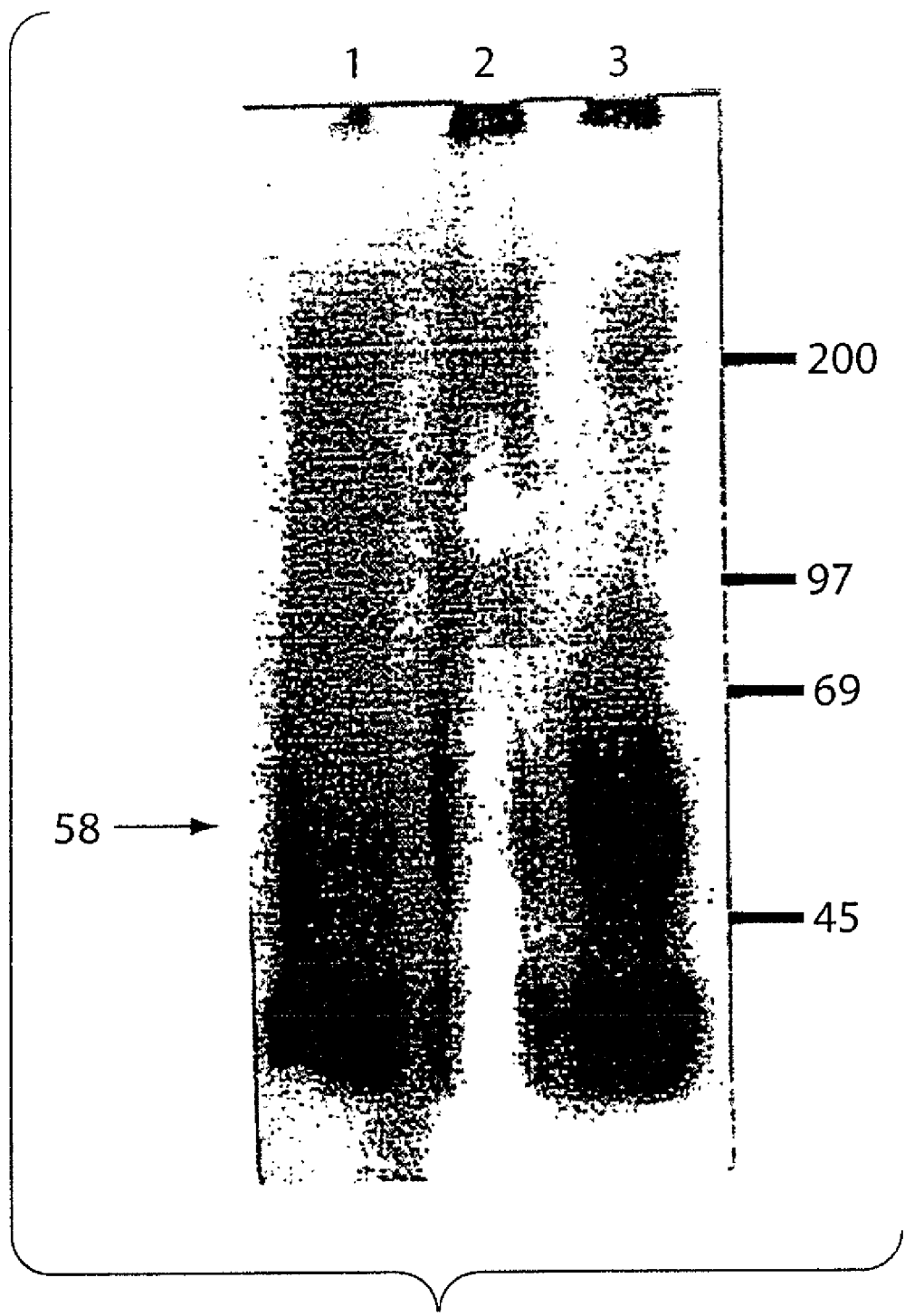
FIG. 2 shows an autoradiogram of SDS-PAGE (7.5% acrylamide) of complexes consisting of $^{125}$I-IL-18 (apparent molecular weight 19 kD), cross-linked to the following preparations of soluble IL-18 binding protein: Lane 1: Wash of the IL-18 affinity column. Lane 2: Elution 2 of the IL-18 affinity column. Lane 3: Elution 3 of the IL-18 affinity column. Molecular weight markers are indicated on the right side (in kD). An arrow indicates the cross-linked product (58 kD).

The ~40 kD protein obtained in the first step was identified as an IL-18 binding protein by its ability to specifically cross-link with $^{125}$I-IL-18 (FIG. 2). The ~40 kD protein was further characterized by N-terminal protein sequence analysis. Aliquots from the eluted protein were subjected to SDS-PAGE, electroblotted to a PVDF membrane and subjected to protein microsequence analysis. Similarly, aliquots from the eluted protein were subjected to direct protein microsequence analysis. In both cases, two polypeptide sequences were obtained. A major sequence and a minor sequence, the latter corresponding to a fragment of human defensin (accession number p11398), starting at amino acid 65. Subtraction of the known defensin sequence provided the following new sequence:

```
T-P-V-S-Q-Q-x-x-x-A-A-A-   (SEQ ID NO:11)
1 . . . 5 . . . . 10. .
``` wherein x represents a yet undetermined amino acid.

In order to obtain a longer and more accurate sequence and in order to identify potential cysteine residues, an aliquot of the eluted fraction was reduced with DTT under denaturing conditions, reacted with 4-vinyl pyridine, desalted by a micro-ultrafiltration device (Ultrafree, cutoff 10,000 Da, Millipore) and subjected to protein microsequence analysis. After sequencing cycle No. 1 the residual protein was reacted with o-phtalaldehyde to block all N-terminal polypeptides other than Pro and sequencing was then resumed. In this way the following single protein sequence was obtained:

```
                                          (SEQ ID NO:10)
TPVSQXXXAA XASVRSTKDP CPSQPPVFPA AKQCPALEVT
1          10         20         30         40
```

(T=Thr; P=Pro; V=Val; S=Ser; Q=Gln; X=Unknown; A=Ala; R=Arg; K=Lys; D=Asp; C=Cys; F=Phe; L=Leu; E=Glu)

The resulting sequence is significantly different from that of any other known protein, as determined by searching protein databases. However, searching the database of The Institute of Genomic Research (TIGR) by the tblastn search program provided a cDNA file, denoted THC123801, whose open reading frame (218 codons) contains a sequence highly homologous to that of the N-terminal sequence of IL-18BP. The homology is hereby shown:

```
1   .......TPVSQXXXAAXASVRSTKDPCPSQPPVFPAAKQCPALEVT..   40  (SEQ ID NO: 12)
           | | |   |||||||||||||||||||||||||||||||
51  VTLLVRATXVXQTTTAATASVRSTKDPCPSQPPVFPAAKQCPALEVTWPE  100  (SEQ ID NO: 13)
```

(The upper sequence (1-40) (SEQ ID NO: 12) is that of the isolated IL-18BP; the lower sequence (51-100) (SEQ ID NO: 13) is derived by translation of TIGR file THC123801).

The affinity-purified urinary IL-18BP retained the ability to bind its labeled ligand ($^{125}$I-IL-18), and following covalent cross-linking, a complex of molecular weight 58 kD was formed. The molecular weight of this complex corresponded to a 1:1 ratio of the ~40 kD IL-18BP and the 19 kD IL-18 (FIG. 2).

The affinity-purified urinary IL-18BP blocked the biological activity of human as well as mouse IL-18. Thus when IL-18BP was added to either human or mouse IL-18 it blocked the ability of IL-18 to induce the production of interferon-y when added together with lipopolysaccharide to cultures of mouse spleen cells (FIG. 3).

Using the partial sequence of the IL-18BP cDNA as provided by the TIGR database, a DNA probe was prepared by reverse-transcription PCR with specific sense and antisense primers and RNA from the human Jurkat T cells. The resulting PCR product was confirmed by DNA sequence analysis. This PCR product was labeled with $^{32}$[p] and used as a probe for screening of four human cDNA libraries, derived from peripheral blood monocytes, from the Jurkat T-cell line, from PBMC and from human spleen. The various independent cDNA clones corresponded to four IL-18BP splice variants. All splice variants coded for putative soluble secreted proteins. The most abundant one (IL-18BPa) had an open reading frame of 192 codons, coding for a signal peptide of 28 amino acid residues followed by a mature putative IL-18BPa, whose first 40 residues matched perfectly with the N-terminal protein sequence of the urinary IL-18BP (SEQ ID NO:1 and SEQ ID NO:2). The position of the cysteine residues suggested that this polypeptide belongs to the immunoglobulin (Ig) super-family. Interestingly, each of the four Gln residues within mature IL-18BPa was a potential N-glycosylation site. The three other variants of IL-18BP were less abundant than IL-18BPa. They included a shorter 1 kb IL-18BPb cDNA, coding for a signal peptide of 28 amino acid residues followed by a mature protein of 85 amino acid residues (SEQ ID NO:3 and SEQ ID NO:4). A third variant, IL-18BPc was represented by a 2.3 kb cDNA, coding for a signal peptide of 28 amino acid residues followed by a mature IL-18BP of 169 amino acid residues (SEQ ID NO:5 and SEQ ID NO:6). The fourth variant, IL-18BPd, coded for a signal peptide of 28 amino acid residues followed by a mature IL-18BP of 133 amino acid residues (SEQ ID NO:7 and SEQ ID NO:8).

To further study the possible existence of additional IL-18BP splice variants, a human genomic library was screened with a probe corresponding to full length IL-18BP cDNA. Five genomic clones, differing in length, were identified in this library. These clones were subjected to DNA sequence analysis with external and internal primers. Altogether, a 7.1 kb contig was assembled from these clones (SEQ ID NO:9). No exon coding for a trans-membrane (TM) receptor was identified within the 7.1 kb contig. All variants shared a common translation start site, coded for the same signal peptide of 28 amino acid residues and soluble mature proteins of varying sizes and C-terminal sequences. The IL-18BP locus contains an additional gene, coding for the nuclear mitotic apparatus protein 1 (NUMA1), positioned at the minus strand. This finding localizes the IL-18BP gene to human chromosome 11q13 (Broach et al., 1981).

An homology search was done with the complete protein sequence of IL-18BPa and the GenPept database, using the Smith Watermann algorithm. It was found that homologues of IL-18BP are expressed in several Poxviruses as secreted proteins of a previously unknown function. It was previously reported that viruses code for various cytokine receptors and that such virally encoded molecules serve as decoy receptors that inhibit immune responses by neutralizing their corresponding cytokine (reviewed by Spriggs, M K, 1994, Curr. Opin. Immunol., 6, 526-529). Therefore the invention further relates to virally encoded homologues of IL-18BP that may also serve as blockers of the biological activity of IL-18. Examples of virus-encoded homologues of IL-18BP are provided in Table 1.

TABLE 1

Virus-encoded proteins, showing high homology to human IL-18BP

| GenPept sequence | Virus type |
| --- | --- |
| MCU60315_54 | U60315 Molluscum contagiosum virus subtype 1 |
| MCU60315_53 | U60315 Molluscum contagiosum virus subtype 1 |
| SWPHLSB_12 | L22013 Swinepox virus |
| CV41KBPL_14 | Cowpox virus |
| VVCGAA_5 | Variola virus |
| U01161_3 174 | Ectromelia virus (mouse Poxvirus) |
| VVU18340_6 | Variola virus |
| VVU18338_7 | Variola virus |
| VVU18337_7 | Variola virus |
| VARCG_7 173 | Variola major virus |
| MCU60315_51 | Molluscum contagiosum virus |
| HNABV_1 | New Hepatitis non-A, non-B associated virus |

IL-18BPa was expressed in monkey COS7 cells. For this purpose, the cDNA of IL-18BPa was inserted into the mammalian expression vector pEF-BOS. A cassette coding for an (His)6 sequence was added to the 3'-end of the IL-18BP ORFs in frame, in order to facilitate purification of the recombinant protein. COS7 cells were transiently transfected with the expression vector and serum-free medium of these cells (150 ml) was concentrated and purified by metal chelate chromatography. IL-18BPa ran as a single band upon SDS-PAGE with silver staining under reducing and non-reducing conditions and had the same apparent molecular mass as that of the urinary IL-18BP. Protein sequence analysis of this preparation revealed the same N-terminal sequence as that of the urinary IL-18BP. Immunoblot analysis of IL-18BPa with antibodies raised against the urinary IL-18BP revealed the same molecular mass band as that of the urinary protein. Furthermore, using immunoprecipitation followed by SDS-PAGE and autoradiography, IL-18BPa was able to displace urinary $^{125}$I-IL-18BP from binding to the antibody. Therefore, IL-18BPa corresponds structurally to the IL-18BP isolated from urine.

Crude and purified IL-18BPa were tested for their ability to inhibit the biological activity of IL-18. IL-18BPa inhibited the activity of human and mouse IL-18 in murine splenocytes, PBMC and the human KG-1 cell line (FIG. 4). In contrast, IL-18BPb did not significantly inhibit the activity of IL-18. These results confirm the identity of IL-18BPa cDNA as the one coding for a biologically active IL-18BP.

The invention further relates to active muteins and fragments of IL-18BPs and viral IL-18BPs and to fused proteins consisting of wild type IL-18BPs and viral IL-18BPs or their active muteins or their active fragments, fused to another polypeptide or protein and exhibiting a similar ability to block the biological activities of IL-18 or its homologues.

As used herein the term "muteins" refers to analogs of an IL-18BP, or analogs of a viral IL-18BP, in which one or more of the amino acid residues of a natural IL-18BP or viral IL-18BP are replaced by different amino acid residues, or are deleted, or one or more amino acid residues are added to the natural sequence of an IL-18BP, or a viral IL-18BP, without changing considerably the activity of the resulting products as compared with the wild type IL-18BP or viral IL-18BP. These muteins are prepared by known synthesis and/or by site-directed mutagenesis techniques, or any other known technique suitable therefor.

Any such mutein preferably has a sequence of amino acids sufficiently duplicative of that of an IL-18BP, or sufficiently duplicative of a viral IL-18BP, such as to have substantially similar activity to IL-18BP. One activity of IL-18BP is its capability of binding IL-18. As long as the mutein has substantial binding activity to IL-18, it can be used in the purification of IL-18, such as by means of affinity chromatography, and thus can be considered to have substantially similar activity to IL-18BP. Thus, it can be determined whether any given mutein has substantially the same activity as IL-18BP by means of routine experimentation comprising subjecting such a mutein, e.g., to a simple sandwich competition assay to determine whether or not it binds to an appropriately labeled IL-18, such as radioimmunoassay or ELISA assay.

In a preferred embodiment, any such mutein has at least 40% identity or homology with the sequence of either an IL-18BP or a virally-encoded IL-18BP homologue. More preferably, it has at least 50%, at least 60%, at least 70%, at least 80% or, most preferably, at least 90% identity or homology thereto.

Muteins of IL-18BP polypeptides or muteins of viral IL-18BPs, which can be used in accordance with the present invention, or nucleic acid coding therefor, include a finite set of substantially corresponding sequences as substitution peptides or polynucleotides which can be routinely obtained by one of ordinary skill in the art, without undue experimentation, based on the teachings and guidance presented herein. For a detailed description of protein chemistry and structure, see Schulz, G. E. et al., Principles of Protein Structure, Springer-Verlag, New York, 1978; and Creighton, T. E., Proteins: Structure and Molecular Properties, W.H. Freeman & Co., San Francisco, 1983, which are hereby incorporated by reference. For a presentation of nucleotide sequence substitutions, such as codon preferences, see Ausubel et al, supra, at §§ A.1.1-A.1.24, and Sambrook et al, supra, at Appendices C and D.

Preferred changes for muteins in accordance with the present invention are what are known as "conservative" substitutions. Conservative amino acid substitutions of IL-18BP polypeptides or proteins or viral IL-18BPs, may include synonymous amino acids within a group which have sufficiently similar physicochemical properties that substitution between members of the group will preserve the biological function of the molecule, Grantham, Science, Vol. 185, pp. 862-864 (1974). It is clear that insertions and deletions of amino acids may also be made in the above-defined sequences without altering their function, particularly if the insertions or deletions only involve a few amino acids, e.g., under thirty, and preferably under ten, and do not remove or displace amino acids which are critical to a functional conformation, e.g., cysteine residues, Anfinsen, "Principles That Govern The Folding of Protein Chains", Science, Vol. 181, pp. 223-230 (1973). Proteins and muteins produced by such deletions and/or insertions come within the purview of the present invention.

Preferably, the synonymous amino acid groups are those defined in Table I. More preferably, the synonymous amino acid groups are those defined in Table II; and most preferably the synonymous amino acid groups are those defined in Table III.

TABLE I

Preferred Groups of Synonymous Amino Acids

| Amino Acid | Synonymous Group |
| --- | --- |
| Ser | Ser, Thr, Gly, Asn |
| Arg | Arg, Gln, Lys, Glu, His |
| Leu | Ile, Phe, Tyr, Met, Val, Leu |
| Pro | Gly, Ala, Thr, Pro |
| Thr | Pro, Ser, Ala, Gly, His, Gln, Thr |
| Ala | Gly, Thr, Pro, Ala |
| Val | Met, Tyr, Phe, Ile, Leu, Val |
| Gly | Ala, Thr, Pro, Ser, Gly |
| Ile | Met, Tyr, Phe, Val, Leu, Ile |
| Phe | Trp, Met, Tyr, Ile, Val, Leu, Phe |
| Tyr | Trp, Met, Phe, Ile, Val, Leu, Tyr |
| Cys | Ser, Thr, Cys |
| His | Glu, Lys, Gln, Thr, Arg, His |
| Gln | Glu, Lys, Asn, His, Thr, Arg, Gln |
| Asn | Gln, Asp, Ser, Asn |
| Lys | Glu, Gln, His, Arg, Lys |
| Asp | Glu, Asn, Asp |
| Glu | Asp, Lys, Asn, Gln, His, Arg, Glu |
| Met | Phe, Ile, Val, Leu, Met |
| Trp | Trp |

TABLE II

More Preferred Groups of Synonymous Amino Acids

| Amino Acid | Synonymous Group |
| --- | --- |
| Ser | Ser |
| Arg | His, Lys, Arg |
| Leu | Leu, Ile, Phe, Met |
| Pro | Ala, Pro |
| Thr | Thr |
| Ala | Pro, Ala |
| Val | Val, Met, Ile |
| Gly | Gly |
| Ile | Ile, Met, Phe, Val, Leu |
| Phe | Met, Tyr, Ile, Leu, Phe |
| Tyr | Phe, Tyr |
| Cys | Cys, Ser |
| His | His, Gln, Arg |
| Gln | Glu, Gln, His |
| Asn | Asp, Asn |
| Lys | Lys, Arg |
| Asp | Asp, Asn |
| Glu | Glu, Gln |
| Met | Met, Phe, Ile, Val, Leu |
| Trp | Trp |

TABLE III

Most Preferred Groups of Synonymous Amino Acids

| Amino Acid | Synonymous Group |
| --- | --- |
| Ser | Ser |
| Arg | Arg |
| Leu | Leu, Ile, Met |
| Pro | Pro |
| Thr | Thr |
| Ala | Ala |
| Val | Val |
| Gly | Gly |
| Ile | Ile, Met, Leu |
| Phe | Phe |
| Tyr | Tyr |
| Cys | Cys, Ser |
| His | His |
| Gln | Gln |
| Asn | Asn |
| Lys | Lys |
| Asp | Asp |
| Glu | Glu |
| Met | Met, Ile, Leu |
| Trp | Met |

Examples of production of amino acid substitutions in proteins which can be used for obtaining muteins of IL-18BP polypeptides or proteins, or muteins of viral IL-18BPs, for use in the present invention include any known method steps, such as presented in U.S. Pat. Nos. Re. 33,653, 4,959,314, 4,588,585 and 4,737,462, to Mark et al; U.S. Pat. No. 5,116,943 to Koths et al., U.S. Pat. No. 4,965,195 to Namen et al; U.S. Pat. No. 4,879,111 to Chong et al; and U.S. Pat. No. 5,017,691 to Lee et al; and lysine substituted proteins presented in U.S. Pat. No. 4,904,584 (Shaw et al).

In another preferred embodiment of the present invention, any mutein of an IL-18BP or a viral IL-18BP, has an amino acid sequence essentially corresponding to that of an IL-18BP, or to a viral IL-18BP. The term "essentially corresponding to" is intended to comprehend proteins with minor changes to the sequence of the natural protein which do not affect the basic characteristics of the natural proteins, particularly insofar as their ability to bind IL-18 and to thereby inhibit its biological activity. The type of changes which are generally considered to fall within the "essentially corresponding to" language are those which would result from conventional mutagenesis techniques of the DNA encoding these proteins, resulting in a few minor modifications, and screening for the desired activity in the manner discussed above.

Muteins in accordance with the present invention include proteins encoded by a nucleic acid, such as DNA or RNA, which hybridizes to DNA or RNA, which encodes an IL-18BP or encodes a viral IL-18BP, in accordance with the present invention, under stringent conditions. The invention also includes such nucleic acid, which is also useful as a probe in identification and purification of the desired nucleic acid. Furthermore, such nucleic acid would be a prime candidate to determine whether it encodes a polypeptide, which retains the functional activity of an IL-18BP of the present invention. The term "stringent conditions" refers to hybridization and subsequent washing conditions, which those of ordinary skill in the art conventionally refer to as "stringent". See Ausubel et al., Current Protocols in Molecular Biology, supra, Interscience, N.Y., §§6.3 and 6.4 (1987, 1992), and Sambrook et al., supra. For example high stringent conditions include washing conditions 12-20° C. below the calculated Tm of the hybrid under study in, e.g., 2×SSC and 0.5% SDS for 5 minutes, 2×SSC and 0.1% SDS for 15 minutes; 0.1×SSC and 0.5% SDS at 37° C. for 30-60 minutes and then, a 0.1×SSC and 0.5% SDS at 68° C. for 30-60 minutes. Those of ordinary skill in this art understand that stringency conditions also depend on the length of the DNA sequences, oligonucleotide probes (such as 10-40 bases) or mixed oligonucleotide probes. If mixed probes are used, it is preferable to use tetramethyl ammonium chloride (TMAC) instead of SSC. See Ausubel, supra.

The term "fused protein" refers to a polypeptide comprising an IL-18BP, or a viral IL-18BP, or a mutein thereof, fused with another protein, which, e.g., has an extended residence time in body fluids. An IL-18BP or a viral IL-18BP, may thus be fused to another protein, polypeptide or the like, e.g., an immunoglobulin or a fragment thereof.

The term "salts" herein refers to both salts of carboxyl groups and to acid addition salts of amino groups of an IL-18BP, a viral IL-18BP, muteins, or fused proteins thereof. Salts of a carboxyl group may be formed by means known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid addition salts include, for example, salts with mineral acids such as, for example, hydrochloric acid or sulfuric acid, and salts with organic acids such as, for example, acetic acid or oxalic acid. Of course, any such salts must have substantially similar activity to IL-18BP.

"Functional derivatives" as used herein cover derivatives of IL-18BPs or a viral IL-18BP, and their muteins and fused proteins, which may be prepared from the functional groups which occur as side chains on the residues or the N- or C-terminal groups, by means known in the art, and are included in the invention as long as they remain pharmaceutically acceptable, i.e. they do not destroy the activity of the protein which is substantially similar to the activity of IL-18BP, or viral IL-18BPs, and do not confer toxic properties on compositions containing it. These derivatives may, for example, include polyethylene glycol side-chains, which may mask antigenic sites and extend the residence of an IL-18BP or a viral IL-18BP in body fluids. Other derivatives include aliphatic esters of the carboxyl groups, amides of the carboxyl groups by reaction with ammonia or with primary or secondary amines, N-acyl derivatives of free amino groups of the amino acid residues formed with acyl moieties (e.g. alkanoyl or carbocyclic aroyl groups) or O-acyl derivatives of free hydroxyl groups (for example that of seryl or threonyl residues) formed with acyl moieties.

As "active fractions" of an IL-18BP, or a viral IL-18BP, muteins and fused proteins, the present invention covers any fragment or precursors of the polypeptide chain of the protein molecule alone or together with associated molecules or residues linked thereto, e.g., sugar or phosphate residues, or aggregates of the protein molecule or the sugar residues by themselves, provided said fraction has substantially similar activity to IL-18BP.

Various recombinant cells such as prokaryotic cells, e.g., E. coli, or other eukaryotic cells, such as yeast or insect cells can produce IL-18BPs or viral IL-18BPs. Methods for constructing appropriate vectors, carrying DNA that codes for an IL-18BP and suitable for transforming (e.g., E. coli, mammalian cells and yeast cells), or infecting insect cells in order to produce a recombinant IL-18BP or a viral IL-18BP are well known in the art. See, for example, Ausubel et al., eds. "Current Protocols in Molecular Biology" Current Protocols, 1993; and Sambrook et al., eds. "Molecular Cloning: A Laboratory Manual", 2nd ed., Cold Spring Harbor Press, 1989.

Cells that produce IL-18 BPs or viral IL-18BPs are made according to known procedures in the art, including for example, by gene activation (See PCT publication WO90/11354, U.S. Pat. Nos. 5,272,071, and 5,641,670, which are incorporated herein by reference in their entirety), and transduction.

For the purposes of expression of IL-18BP proteins, or viral IL-18BPs, DNA encoding an IL-18BP or a viral IL-18BP, their fragments, muteins or fused proteins, and the operably linked transcriptional and translational regulatory signals, are inserted into eukaryotic vectors which are capable of integrating the desired gene sequences into the host cell chromosome. In order to be able to select the cells which have stably integrated the introduced DNA into their chromosomes, one or more markers which allow for selection of host cells which contain the expression vector is used. The marker may provide for prototrophy to an auxotropic host, biocide resistance, e.g., antibiotics, or resistance to heavy metals, such as copper, or the like. The selectable marker gene can either be directly linked to the DNA gene sequences to be expressed, or introduced into the same cell by cotransfection. Additional elements may also be needed for optimal synthesis of single chain binding protein mRNA. These elements may include splice signals, as well as transcription promoters, enhancers, and termination signals.

Said DNA molecule to be introduced into the cells of choice will preferably be incorporated into a plasmid or viral vector capable of autonomous replication in the recipient host. Preferred prokaryotic plasmids are derivatives of pBr322. Preferred eukaryotic vectors include BPV, vaccinia, SV40, 2-micron circle, etc., or their derivatives. Such plasmids and vectors are well known in the art (Anderson, 1997; Bollon, 1980; Botstein, 1982 Broach, 1981; Kendall et al., 1987). Once the vector or DNA sequence containing the construct(s) has been prepared for expression, the expression vector may be introduced into an appropriate host cell by any of a variety of suitable means, such as transformation, transfection, lipofection, conjugation, protoplast fusion, electroporation, calcium phosphate precipitation, direct microinjection, etc.

Host cells to be used in this invention may be either prokaryotic or eukaryotic. Preferred prokaryotic hosts include bacteria such as E. coli, Bacillus, Streptomyces, Pseudomonas, Salmonella, Serratia, etc. The most preferred prokaryotic host is E. coli. Bacterial hosts of particular interest include E. coli K12 strain 294 (ATCC 31446), E. coli X1776 (ATCC 31537), E. coli W3110 (F-, lambda-, phototropic (ATCC 27325). Under such conditions, the protein will not be glycosylated. The prokaryotic host must be compatible with the replicon and control sequences in the expression plasmid.

However, since IL-18BPs are glycosylated proteins, eukaryotic hosts are preferred over prokaryotic hosts. Preferred eukaryotic hosts are mammalian cells, e.g., human, monkey, mouse and Chinese hamster ovary (CHO) cells, because they provide post-translational modifications to protein molecules including correct folding, correct disulfide bond formation, as well as glycosylation at correct sites. Also yeast cells and insect cells can carry out post-translational peptide modifications including high mannose glycosylation.

A number of recombinant DNA strategies exist which utilize strong promoter sequences and high copy number of plasmids, which can be utilized for production of the desired proteins in yeast and in insect cells. Yeast and insect cells recognize leader sequences on cloned mammalian gene products and secrete mature IL-18BP. After the introduction of the vector, the host cells are grown in a selective medium, which selects for the growth of vector-containing cells. Expression of the cloned gene sequence(s) results in the production of an IL-18BP, a viral IL-18BP, fusion proteins, or muteins or fragments thereof. The above-mentioned cloning, clone isolation, identification, characterization and sequencing procedures are described in more detail hereinafter in the Examples.

The expressed proteins are then isolated and purified by any conventional procedure involving extraction, precipitation, chromatography, electrophoresis, or the like, or by affinity chromatography, using, e.g., an anti-IL-18BP monoclonal antibodies immobilized on a gel matrix contained within a column. Crude preparations containing said recombinant IL-18BP are passed through the column whereby IL-18BP will be bound to the column by the specific antibody, while the impurities will pass through. After washing, the protein is eluted from the gel under conditions usually employed for this purpose, i.e. at a high or a low pH, e.g. pH 11 or pH 2.

The invention further relates to vectors useful for expression of an IL-18BP or a viral IL-18BP or their derivatives in mammals and more specifically in humans. Vectors for short and long-term expression of genes in mammals are well known in the literature. Studies have shown that gene delivery to e.g., skeletal muscle, vascular smooth muscle and liver result in systemic levels of therapeutic proteins. Skeletal muscle is a useful target because of its large mass, vascularity and accessibility. However, other targets and particularly bone marrow precursors of immune cells have been used successfully. Currently available vectors for expression of proteins in e.g., muscle include plasmid DNA, liposomes, protein-DNA conjugates and vectors based on adenovirus, adeno-associated virus and herpes virus. Of these, vectors based on adeno-associated virus (AAV) have been most successful with respect to duration and levels of gene expression and with respect to safety considerations (Kessler, P. D. 1996, Proc. Natl. Acad. Sci. USA 93,14082-14087).

Procedures for construction of an AAV-based vector have been described in detail (Snyder et al, 1996, Current Protocols in Human Genetics, Chapters 12.1.1-12.1.17, John Wiley & Sons) and are incorporated into this patent. Briefly plasmid psub201, containing the wild-type AAV genome is cut with the restriction enzyme Xba I and ligated with a construct consisting of an efficient eukaryotic promoter, e.g., the cytomegalovirus promoter, a Kozak consensus sequence, a DNA sequence coding for an IL-18BP or a viral IL-18BP, or their muteins or fusion proteins or fragments thereof, a suitable 3' untranslated region and a polyadenylation signal, e.g., the polyadenylation signal of simian virus 40. The resulting recombinant plasmid is cotransfected with an helper AAV plasmid e.g., pAAV/Ad into mammalian cells e.g., human T293 cells. The cultures are then infected with adenovirus as a helper virus and culture supernatants are collected after 48-60 hours. The supernatants are fractionated by ammonium sulfate precipitation, purified on a CsCl density gradient, dialyzed and then heated at 56° C. to destroy any adenovirus, whereas the resulting recombinant AAV, capable of expressing IL-18BP or a viral IL-18BP, or their muteins or fusion proteins remains stable at this step.

So far, the physiological role of the soluble cytokine receptors has not been established. The soluble receptors bind their specific ligands and in most cases inhibit their biological activity, as was shown, e.g., in the TNF system (Dao et al., 1996; Engelmann et al., 1989). In very few cases, e.g., IL-6, the soluble receptor enhances the biological activity. The recombinant soluble TNF receptor, also known as TBP (TNF binding protein) was found to prevent septic shock in animal models, while soluble forms of IL-1 receptor were found to have profound inhibitory effects on the development of in vivo alloreactivity in mouse allograft recipients.

Similarly, the IL-18BPs and viral IL-18BPs of the present invention may find use as modulators of IL-18 activity, e.g. in type I diabetes, in sepsis, in autoimmune diseases, in graft rejections, rheumatoid arthritis, inflammatory bowel disease, sepsis, multiple sclerosis, ischemic heart disease including acute heart attacks, ischemic brain injury, chronic hepatitis, psoriasis, chronic hepatitis and acute hepatitis. It may thus be used, e.g. in any disease in which endogenous production or exogenous administration of IL-18 induces the disease or aggravates the situation of the patient.

The present invention further relates to pharmaceutical compositions comprising a pharmaceutically acceptable carrier and an IL-18BP or a viral IL-18BP of the invention or their active muteins, fused proteins and their salts, functional derivatives or active fractions thereof.

The present invention further relates to pharmaceutical compositions comprising a pharmaceutically acceptable carrier and e.g., a viral vector such as any one of said AAV-based viral vectors or another vector expressing an IL-18BP or viral IL-18BP or their muteins, fragments or fusion proteins thereof and suitable for administration to humans and other mammals for the purpose of attaining expression in vivo of IL-18BP or a viral IL-18BP or their muteins or fragments or fusion protein of the invention.

The pharmaceutical compositions of the invention are prepared for administration by mixing an IL-18BP or a viral IL-18BP, or their derivatives, or vectors for expressing same with physiologically acceptable carriers, and/or stabilizers and/or excipients, and prepared in dosage form, e.g., by lyophilization in dosage vials. The method of administration can be via any of the accepted modes of administration for similar agents and will depend on the condition to be treated, e.g., intravenously, intramuscularly, subcutaneously, by local injection or topical application, or continuously by infusion, etc. The amount of active compound to be administered will depend on the route of administration, the disease to be treated and the condition of the patient. Local injection, for instance, will require a lower amount of the protein on a body weight basis than will intravenous infusion.

Accordingly, IL-18BPs, or viral IL-18BPs, or vectors expressing same in vivo are indicated for the treatment of autoimmune diseases, Type I diabetes, rheumatoid arthritis, graft rejections, inflammatory bowel disease, sepsis, multiple sclerosis, ischemic heart disease including acute heart attacks, ischemic brain injury, chronic hepatitis, psoriasis, chronic pancreatitis and acute pancreatitis and similar diseases, in which there is an aberrant expression of IL-18, leading to an excess of IL-18 or in cases of complications due to exogenously administered IL-18.

The invention also includes antibodies against an IL-18BP or a viral IL-18BP, as well as against their muteins, fused proteins, salts, functional derivatives and active fractions. The term "antibody" is meant to include polyclonal antibodies, monoclonal antibodies (MAbs), chimeric antibodies, anti-idiotypic (anti-Id) antibodies to antibodies that can be labeled in soluble or bound form, as well as fragments thereof provided by any known technique, such as, but not limited to enzymatic cleavage, peptide synthesis or recombinant techniques.

Polyclonal antibodies are heterogeneous populations of antibody molecules derived from the sera of animals immunized with an antigen. A monoclonal antibody contains a substantially homogeneous population of antibodies specific to antigens, which population contains substantially similar epitope binding sites. MAbs may be obtained by methods known to those skilled in the art. See, for example Kohler and Milstein, Nature 256:495-497 (1975); U.S. Pat. No. 4,376, 110; Ausubel et al, eds., supra, Harlow and Lane, ANTIBODIES: A LABORATORY MANUAL, Cold Spring Harbor Laboratory (1988); and Colligan et al., eds., Current Protocols in Immunology, Greene Publishing Assoc. and Wiley Interscience, N.Y., (1992, 1993), the contents of which references are incorporated entirely herein by reference. Such antibodies may be of any immunoglobulin class including IgG, IgM, IgE, IgA, GILD and any subclass thereof. A hybridoma producing a MAb of the present invention may be cultivated in vitro, in situ or in vivo. Production of high titers of MAbs in vivo or in situ makes this the presently preferred method of production.

Chimeric antibodies are molecules, different portions of which are derived from different animal species, such as those having the variable region derived from a murine MAb and a human immunoglobulin constant region. Chimeric antibodies are primarily used to reduce immunogenicity in application and to increase yields in production, for example, where murine MAbs have higher yields from hybridomas but higher immunogenicity in humans, such that human/murine chimeric MAbs are used. Chimeric antibodies and methods for their production are known in the art (Cabilly et al, Proc. Natl. Acad. Sci. USA 81:3273-3277 (1984); Morrison et al., Proc. Natl. Acad. Sci. USA 81:6851-6855 (1984); Boulianne et al., Nature 312:643-646 (1984); Cabilly et al., European Patent Application 125023 (published Nov. 14, 1984); Neuberger et al., Nature 314:268-270 (1985); Taniguchi et al., European Patent Application 171496 (published Feb. 19, 1985); Morrison et al., European Patent Application 173494 (published Mar. 5, 1986); Neuberger et al., PCT Application WO 8601533, (published Mar. 13, 1986); Kudo et al., European Patent Application 184187 (published Jun. 11, 1986); Morrison et al., European Patent Application 173494 (published Mar. 5, 1986); Sahagan et al., J. Immunol. 137:1066-1074 (1986); Robinson et al., International Patent Publication, WO 9702671 (published 7 May 1987); Liu et al., Proc. Natl. Acad. Sci. USA 84:3439-3443 (1987); Sun et al., Proc. Natl. Acad. Sci. USA 84:214-218 (1987); Better et al., Science 240:1041-1043 (1988); and Harlow and Lane, ANTIBODIES: A LABORATORY MANUAL, supra. These references are entirely incorporated herein by reference.

An anti-idiotypic (anti-Id) antibody is an antibody, which recognizes unique determinants generally, associated with the antigen-binding site of an antibody. An Id antibody can be prepared by immunizing an animal of the same species and genetic type (e.g., mouse strain) as the source of the MAb with the MAb to which an anti-Id is being prepared. The immunized animal will recognize and respond to the idiotypic determinants of the immunizing antibody by producing an antibody to these idiotypic determinants (the anti-Id antibody). See, for example, U.S. Pat. No. 4,699,880, which is herein entirely incorporated by reference.

The anti-Id antibody may also be used as an "immunogen" to induce an immune response in yet another animal, producing a so-called anti-anti-ld antibody. The anti-anti-Id may be epitopically identical to the original MAb, which induced the anti-Id. Thus, by using antibodies to the idiotypic determinants of a MAb, it is possible to identify other clones expressing antibodies of identical specificity.

Accordingly, MAbs generated against IL-18BP and related proteins of the present invention may be used to induce anti-Id antibodies in suitable animals, such as BALB/c mice. Spleen cells from such immunized mice are used to produce anti-Id hybridomas secreting anti-Id Mabs. Further, the anti-Id Mabs can be coupled to a carrier such as keyhole limpet hemocyanin (KLH) and used to immunize additional BALB/c mice. Sera from these mice will contain anti-anti-ld antibodies that have the binding properties of the original MAb specific for an IL-18BP epitope or epitopes of a viral IL-18BP.

The anti-Id MAbs thus have their own idiotypic epitopes, or "idiotopes" structurally similar to the epitope being evaluated, such as an IL-18BP or a viral IL-18BP.

The term "antibody" is also meant to include both intact molecules as well as fragments thereof, such as, for example, Fab and F(ab')$_2$, which are capable of binding antigen. Fab and F(ab')$_2$ fragments lack the Fc fragment of intact antibody, clear more rapidly from the circulation, and may have less non-specific tissue binding than an intact antibody (Wahl et al., J. Nucl. Med. 24:316-325 (1983)). It will be appreciated that Fab and F(ab')$_2$ and other fragments of the antibodies useful in the present invention may be used for the detection and quantitation of an IL-18BP or a viral IL-18BP, according to the methods disclosed herein for intact antibody molecules. Such fragments are typically produced by proteolytic cleavage, using enzymes such as papain (to produce Fab fragments) or pepsin (to produce F(ab')$_2$ fragments).

An antibody is said to be "capable of binding" a molecule if it is capable of specifically reacting with the molecule to thereby bind the molecule to the antibody. The term "epitope" is meant to refer to that portion of any molecule capable of being bound by an antibody which can also be recognized by that antibody. Epitopes or "antigenic determinants" usually consist of chemically active surface groupings of molecules such as amino acids or sugar side chains and have specific three dimensional structural characteristics as well as specific charge characteristics.

An "antigen" is a molecule or a portion of a molecule capable of being bound by an antibody which is additionally capable of inducing an animal to produce antibody capable of binding to an epitope of that antigen. An antigen may have one or more than one epitope. The specific reaction referred to above is meant to indicate that the antigen will react, in a highly selective manner, with its corresponding antibody and not with the multitude of other antibodies which may be evoked by other antigens.

The antibodies, including fragments of antibodies, useful in the present invention may be used to detect quantitatively or qualitatively an IL-18BP or a viral IL-18BP, or related proteins in a sample or to detect presence of cells, which express such proteins of the present invention. This can be accomplished by immunofluorescence techniques employing a fluorescently labeled antibody (see below) coupled with light microscopic, flow cytometric, or fluorometric detection.

The antibodies (or fragments thereof) useful in the present invention may be employed histologically, as in immunofluorescence or immunoelectron microscopy, for in situ detection of an IL-18BP or a viral IL-18BP, and related proteins of the present invention. In situ detection may be accomplished by removing a histological specimen from a patient, and providing the a labeled antibody of the present invention to such a specimen. The antibody (or fragment) is preferably provided by applying or by overlaying the labeled antibody (or fragment) to a biological sample. Through the use of such a procedure, it is possible to determine not only the presence of an IL-18BP or a viral IL-18BP, or related proteins but also its distribution on the examined tissue. Using the present invention, those of ordinary skill will readily perceive that any of wide variety of histological methods (such as staining procedures) can be modified in order to achieve such in situ detection.

Such assays for an IL-18BP or a viral IL-18BP, or related proteins of the present invention typically comprises incubating a biological sample, such as a biological fluid, a tissue extract, freshly harvested cells such as lymphocytes or leukocytes, or cells which have been incubated in tissue culture, in the presence of a detectably labeled antibody capable of identifying IL-18BP or related proteins, and detecting the antibody by any of a number of techniques well-known in the art.

The biological sample may be treated with a solid phase support or carrier such as nitrocellulose, or other solid support or carrier which is capable of immobilizing cells, cell particles or soluble proteins. The support or carrier may then be washed with suitable buffers followed by treatment with a detectably labeled antibody in accordance with the present invention. The solid phase support or carrier may then be washed with the buffer a second time to remove unbound antibody. The amount of bound label on said solid support or carrier may then be detected by conventional means.

By "solid phase support", "solid phase carrier", "solid support", "solid carrier", "support" or "carrier" is intended any support or carrier capable of binding antigen or antibodies. Well-known supports or carriers, include glass, polystyrene, polypropylene, polyethylene, dextran, nylon amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support or carrier configuration may be spherical, as in a bead, or cylindrical, as in the inside surface of a test tube, or the external surface of a rod. Alternatively, the surface may be flat such as a sheet, test strip, etc. Preferred supports or carriers include polystyrene beads. Those skilled in the art will know many other suitable carriers for binding antibody or antigen, or will be able to ascertain the same by use of routine experimentation.

The binding activity of a given lot of antibody in accordance with the present invention may be determined according to well known methods. Those skilled in the art will be able to determine operative and optimal assay conditions for each determination by employing routine experimentation.

Other such steps as washing, stirring, shaking, filtering and the like may be added to the assays as is customary or necessary for the particular situation.

One of the ways in which an antibody in accordance with the present invention can be detectably labeled is by linking the same to an enzyme and use in an enzyme immunoassay (EIA). This enzyme, in turn, when later exposed to an appropriate substrate, will react with the substrate in such a manner as to produce a chemical moiety which can be detected, for example, by spectrophotometric, fluorometric or by visual means. Enzymes which can be used detectably label the antibody include, but are not limited to, malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods, which employ a chromogenic substrate for the enzyme. Detection may also be accomplished by visual comparison of the extent of enzymatic reaction of a substrate in comparison with similarly prepared standards.

Detection may be accomplished using any of a variety of other immunoassays. For example, by radioactivity labeling the antibodies or antibody fragments, it is possible to detect an IL-18BP or a viral IL-18BP, through the use of a radioimmunoassay (RIA). A good description of RIA maybe found in Laboratory Techniques and Biochemistry in Molecular Biology, by Work, T. S. et al., North Holland Publishing Company, NY (1978) with particular reference to the chapter entitled "An Introduction to Radioimmuno Assay and Related Techniques" by Chard, T., incorporated by reference herein. The radioactive isotope can be detected by such means as the use of a gamma counter or a scintillation counter or by autoradiography.

It is also possible to label an antibody in accordance with the present invention with a fluorescent compound. When the fluorescently labeled antibody is exposed to light of the proper wavelength, its presence can be then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriamine pentaacetic acid (ETPA).

The antibody can also be detectably labeled by coupling it to biotin. Biotinylated antibody can then be detected by avidin or streptavidin coupled to a fluorescent compound or to an enzyme such as peroxidase or to a radioactive isotope and the like.

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

An antibody molecule of the present invention may be adapted for utilization in a immunometric assay, also known as a "two-site" or "sandwich" assay. In a typical immunometric assay, a quantity of unlabeled antibody (or fragment of antibody) is bound to a solid support or carrier and a quantity of detectably labeled soluble antibody is added to permit detection and/or quantitation of the ternary complex formed between solid-phase antibody, antigen, and labeled antibody.

Typical, and preferred, immunometric assays include "forward" assays in which the antibody bound to the solid phase is first contacted with the sample being tested to extract the antigen form the sample by formation of a binary solid phase antibody-antigen complex. After a suitable incubation period, the solid support or carrier is washed to remove the residue of the fluid sample, including unreacted antigen, if any, and then contacted with the solution containing an unknown quantity of labeled antibody (which functions as a "reporter molecule"). After a second incubation period to permit the labeled antibody to complex with the antigen bound to the solid support or carrier through the unlabeled antibody, the solid support or carrier is washed a second time to remove the unreacted labeled antibody.

In another type of "sandwich" assay, which may also be useful with the antigens of the present invention, the so-called "simultaneous" and "reverse" assays are used. A "simultaneous" assay involves a single incubation step as the antibody bound to the solid support or carrier and labeled antibody are both added to the sample being tested at the same time. After the incubation is completed, the solid support or carrier is washed to remove the residue of fluid sample and uncomplexed labeled antibody. The presence of labeled antibody associated with the solid support or carrier is then determined as it would be in a conventional "forward" sandwich assay.

In the "reverse" assay, stepwise addition first of a solution of labeled antibody to the fluid sample followed by the addition of unlabeled antibody bound to a solid support or carrier after a suitable incubation period is utilized. After a second incubation, the solid phase is washed in conventional fashion to free it of the residue of the sample being tested and the solution of unreacted labeled antibody. The determination of labeled antibody associated with a solid support or carrier is then determined as in the "simultaneous" and "forward" assays.

The present invention also provides DNA molecules encoding any of the proteins of the present invention as defined above, replicable expression vehicles comprising any such DNA molecules, host cells transformed with any such expression vehicles including prokaryotic and eukaryotic and host cells, preferably CHO cells. The invention also includes a process for the production of expression vectors coding for any of the proteins of the present invention for the purpose of their expression in humans and other mammals.

The invention also includes a process for the production of any of the proteins of the present invention by culturing a transformed cell in accordance with the present invention and recovering the protein encoded by the DNA molecule and the expression vehicle within such transformed host cell.

In addition to the use of an IL-18BP or a viral IL-18BP, in modulating the activity of IL-18, they can, of course, also be employed for the purification of IL-18 itself. For this purpose, IL-18BP or a viral IL-18BP is coupled to an affinity column and crude IL-18 is passed through. The IL-18 can then be recovered from the column by, e.g., elution at low pH.

The present invention further relates to the treatment and/or prevention of liver injury using inhibitors of IL-18. An inhibitor according to the invention can be an inhibitor of IL-18 production and/or action.

The term "inhibitor of IL-18" within the context of this invention refers to any molecule modulating IL-18 production and/or action in such a way that IL-18 production and/or action is attenuated, reduced, or partially, substantially or completely prevented or blocked.

An inhibitor of production can be any molecule negatively affecting the synthesis, processing or maturation of IL-18 on the level of the gene, the mRNA or the protein. The inhibitors considered according to the invention can be, for example, suppressors of gene expression of the interleukin IL-18, antisense mRNAs reducing or preventing the transcription of the IL-18 mRNA or leading to degradation of the mRNA, proteins impairing correct folding, or partially or substantively preventing secretion of IL-18, proteases degrading the IL-18, once it has been synthesized, and the like.

An inhibitor of IL-18 action can be an IL-18 antagonist, for example. Antagonists can either bind to or sequester the IL-18 molecule itself with sufficient affinity and specificity to partially or substantially neutralize the IL-18 or IL-18 binding site(s) responsible for IL-18 binding to its ligands (like, e.g. to its receptors). An antagonist may also inhibit the IL-18 signaling pathway, activated within the cells upon IL-18/receptor binding.

Inhibitors of IL-18 action may be also soluble IL-18 receptors or molecules mimicking the receptors, or agents blocking the IL-18 receptors, IL-18 antibodies, like monoclonal antibodies, for example, or any other agent or molecule preventing the binding of IL-18 to its targets, thus diminishing or preventing triggering of the intra- or extracellular reactions mediated by IL-18.

The invention particularly relates to for the treatment or prevention of both acute and chronic liver diseases, such as alcoholic hepatitis, viral hepatitis, immune hepatitis, fulminant hepatitis, liver cirrhosis, and primary biliary cirrhosis, for example.

The IL-18 inhibitors contemplated herein can further be used for the treatment of acute hepatic poisoning caused by an high amount of paracetamol. Such an acute hepatic poisoning may be due to an overdose, be it accidental or on purpose.

As shown in the examples below, it has been surprisingly found that IL-18 inhibitors are particularly effective in the prevention and treatment of fulminant hepatitis (acute hepatitis). Therefore, the invention preferably relates to the prevention and/or or treatment of fulminant hepatitis.

It has been surprisingly found that a combination of an inhibitor of IL-18 with an inhibitor of tumor necrosis factor (TNF) leads to a complete blockade of liver injury in a murine model of disease. The invention therefore further relates to the use of an IL-18 inhibitor in combination with a TNF-inhibitor for the treatment and/or prevention of liver injury.

An inhibitor of TNF can be a TNF antagonist, for example. TNF antagonists exert their activity in several ways. First, antagonists can bind to or sequester the TNF molecule itself with sufficient affinity and specificity to partially or substantially neutralize the TNF epitope or epitopes responsible for TNF receptor binding (hereinafter termed "sequestering antagonists"). A sequestering antagonist may be, for example, an antibody directed against TNF.

Alternatively, TNF antagonists can inhibit the TNF signaling pathway activated by the cell surface receptor after TNF binding (hereinafter termed "signaling antagonists"). Both groups of antagonists are useful, either alone or together, in combination with an IL-18 inhibitor, in the prevention of therapy of liver injury.

TNF antagonists are easily identified and rated by routine screening of candidates for their effect on the activity of native TNF on susceptible cell lines in vitro, for example human B cells, in which TNF causes proliferation and immunoglobulin secretion. The assay contains TNF formulation at varying dilutions of candidate antagonist, e.g. from 0.1 to 100 times the molar amount of TNF used in the assay, and controls with no TNF or only antagonist (Tucci et al., 1992).

Sequestering antagonists are the preferred TNF antagonists to be used according to the present invention. Amongst sequestering antagonists, those polypeptides that bind TNF with high affinity and possess low immunogenicity are preferred. Soluble TNF receptor molecules and neutralizing antibodies to TNF are particularly preferred. For example, soluble TNF receptors TNF-RI and TNF-RII are useful in the present invention.

Truncated forms of these receptors, comprising the extracellular domains of the receptors or functional portions thereof, are highly preferred TNF inhibitors, according to the present invention. Truncated soluble TNF type-I and type-II receptors are described in EP914431, for example.

The IL-18 inhibitor can be used simultaneously, sequentially or separately with the TNF inhibitor.

Preferably, a combination of an IL-18 antibody or antiserum and a soluble receptor of TNF, having TNF inhibiting activity, is used.

The present invention is further based on the finding of a beneficial effect of an IL-18 inhibitor in arthritis. The invention therefore further relates to the use of an IL-18 inhibitor for the manufacture of a medicament for the treatment and/or prevention of arthritis.

According to the present invention, the term "arthritis" includes all different types of arthritis and arthritic conditions, both acute and chronic arthritis, as defined for example in the Homepage of the Department of Orthopaedics of the University of Washington on Arthritis. Examples for arthritic conditions are ankylosing spondylitis, back pain, carpal deposition syndrome, Ehlers-Danlos-Syndrome, gout, juvenile arthritis, lupus erythematosus, myositis, osteogenesis imperfecta, osteoporosis, polyartheritis, polymyositis, psoriatic arthritis, Reiter's syndrome, scleroderma, arthritis with bowel disease, Behcets's disease, children's arthritis, degenerative joint disease, fibromyalgia, infectious arthritis, Lyme disease, Marfan syndrome, osteoarthritis, osteonecrosis, Pagets Disease, Polymyalgia rheumatica, pseudogout, reflex sympathetic dystrophy, rheumatoid arthritis, rheumatism, Sjogren's syndrome, familial adenomatous polyposis and the like.

Preferably, according to the invention, inhibitors of IL-18 are provided for treatment and/or prevention of inflammatory arthritis. Inflammatory arthritis is classified as a chronic arthritis, according to the persistent, continuous or recurring course of the disease.

In a preferred embodiment of the invention, the inflammatory arthritis is rheumatoid arthritis (RA). RA causes inflammation in the lining of the joints (the synovial membrane, a one cell layer epithelium) and/or internal organs. The disease tends to persist for many years, typically affects many different joints throughout the body and ultimately can cause damage to cartilage, bone, tendons, and ligaments. The joints that may be affected by RA are the joints located in the neck, shoulders, elbows, hips, wrists, hands, knees, ankles and feet, for example. In many cases, the joints are inflamed in a symmetrical pattern in RA.

RA is prevalent in about 1% of the population in the United States, being distributed within all ethnic groups and ages. It occurs all over the world, and women outnumber men by 3 to 1 among those having RA.

As shown in the examples below, an inhibitor of IL-18 has been proven to exhibit a highly efficacious beneficial effect on cartilage erosion. The invention therefore further relates to the use of an inhibitor of IL-18 in the manufacture of a medicament for treatment and/or prevention of cartilage destruction, i.e. to the use of an IL-18 inhibitor as a chondroprotective agent. The IL-18 inhibitor may be used in any condition in which cartilage destruction or erosion occurs. Cartilage destruction is the progressive decline in the structural integrity of joint articular cartilage. It occurs for example in conditions affecting articular cartilage such as rheumatoid arthritis, juvenile rheumatoid arthritis, or osteoarthritis, but also in infectious synovitis, for instance.

In a preferred embodiment, the inhibitor of IL-18 is selected from inhibitors of caspase-1 (ICE), antibodies directed against IL-18, antibodies directed against any of the IL-18 receptor subunits, inhibitors of the IL-18 signalling pathway, antagonists of IL-18 which compete with IL-18 and block the IL-18 receptor, and IL-18 binding proteins, isoforms, muteins, fused proteins, functional derivatives, active fractions or circularly permutated derivatives thereof having the same activity.

The term "IL-18 binding proteins" is used herein synonymously with "IL18BP". It comprises IL-18 binding proteins as defined in detail above, including splice variants and/or isoforms of IL-18 binding proteins. In particular, human isoforms a and c of IL-18BP are useful in accordance with the presence invention. The proteins useful according to the present invention may be glycosylated or non-glycosylated, they may be derived from natural sources, like urine, or produced recombinantly. Recombinant expression may be carried out in prokaryotic expression systems like E. coli, or in eukaryotic, preferably in mammalian, expression systems.

The terms "muteins", "functional derivatives", "active fractions" and "circularly permutated derivatives" have been defined above.

Functional derivatives of IL-18BP may be conjugated to polymers in order to improve the properties of the protein, such as the stability, half-life, bioavailability, tolerance by the human body, or immunogenicity. To achieve this goal, IL18-BP may be linked e.g. to Polyethlyenglycol (PEG). PEGylation may be carried out by known methods, described in WO 92/13095, for example.

The term "fused protein" refers to a polypeptide comprising an IL-18BP, or a viral IL-18BP, or a mutein thereof, fused with another protein, which, e.g., has an extended residence time in body fluids. An IL-18BP or a viral IL-18BP, may thus be fused to another protein, polypeptide or the like, e.g., an immunoglobulin or a fragment thereof. The fusion may be direct, or via a short linker peptide which can be as short as 1 to 3 amino acid residues in length or longer, for example, 13 amino acid residues in length. Said linker may be a tripeptide of the sequence E-F-M (Glu-Phe-Met), for example, or a 13-amino acid linker sequence comprising Glu-Phe-Gly-Ala-Gly-Leu-Val-Leu-Gly-Gly-Gln-Phe-Met (SEQ ID NO: 14) introduced between the IL-18BP sequence and the immunoglobulin sequence. Fusion proteins comprising IL-18BP fused to all or part of an immunoglobulin are highly preferred. For example, IL-18BP may be fused to the constant regions of Ig molecules, preferably to heavy chain regions, like the CH2 and CH3 domains of human IgG1, for example. The generation of specific fusion proteins comprising IL-18BP and a portion of an immunoglobulin are described in example 11 of WP99/09063. Other isoforms of Ig molecules are also suitable for the generation of fusion proteins according to the present invention, such as isoforms $IgG_2$ or $IgG_4$ or other Ig classes, like IgM or IgA, for example. Fusion proteins may be monomeric or multimeric, hetero- or homomultimeric.

In a further preferred embodiment of the invention, the inhibitor of IL-18 is an IL-18 antibody. Anti-IL-18 antibodies may be polyclonal or monoclonal, chimeric, fully humanised, or even fully human. Recombinant antibodies and fragments thereof are characterised by high affinity binding to IL-18 in vivo and low toxicity. The antibodies which can be used in the invention are characterised by their ability to treat patients for a period sufficient to have good to excellent regression or alleviation of the pathogenic condition or any symptom or group of symptoms related to a pathogenic condition, and a low toxicity.

Neutralising antibodies are readily raised in animals such as rabbits, goat or mice by immunisation with IL-18. Immunised mice are particularly useful for providing sources of B cells for the manufacture of hybridomas, which in turn are cultured to produce large quantities of anti-IL-18 monoclonal antibodies.

Chimeric antibodies are immunoglobulin molecules characterised by two or more segments or portions derived from different animal species. Generally, the variable region of the chimeric antibody is derived from a non-human mammalian antibody, such as murine monoclonal antibody, and the immunoglobulin constant region is derived from a human immunoglobulin molecule. Preferably, both regions and the combination have low immunogenicity as routinely determined (Elliott, M. J., Maini, R. N., Feldmann, M., Long-Fox, A., Charles, P., Bijl, H., and Woody, J. N., 1994). Humanised antibodies are immunoglobulin molecules created by genetic engineering techniques in which the murine constant regions are replaced with human counterparts while retaining the murine antigen binding regions. The resulting mouse-human chimeric antibody preferably have reduced immunogenicity and improved pharmacokinetics in humans (Knight, D. M., Trinh, H., Le, J., Siegel, S., Shealy, D., McDonough, M., Scallon, B., Moore, M. A., Vilcek, J., and Daddona, P., 1993).

Thus, in a further preferred embodiment, IL-18 antibody is a humanised IL-18 antibody. Preferred examples of humanized anti-IL-18 antibodies are described in the European Patent Application EP 0 974 600, for example.

In yet a further preferred embodiment, the IL-18 antibody is fully human. The technology for producing human antibodies is described in detail e.g. in WO00/76310, W099/53049, U.S. Pat. No. 6,162,963 or AU5336100. Fully human antibodies are preferably recombinant antibodies, produced in transgenic animals, e.g. xenomice, comprising all or parts of functional human Ig loci.

In a highly preferred embodiment of the present invention, the inhibitor of IL-18 is a IL-18BP, or an isoform, a mutein, fused protein, functional derivative, active fraction or circularly permutated derivative thereof essentially having at least an activity similar to IL-18BP. Preferred active fractions have an activity which is better than the activity of IL-18BP or have further advantages, like a better stability or a lower toxicity or immunogenicity, or they are easier to produce in large quantities.

Interferons are predominantly known for inhibitory effects on viral replication and cellular proliferation. Interferon γ, for example, plays an important role in promoting immune and inflammatory responses. Interferon β (IFN-β, an interferon type I), is said to play an anti-inflammatory role. Studies published by Triantaphyllopoulos et al. (1999) indicated that IFN-β has a beneficial effect in the therapy of rheumatoid arthritis, as shown in a mouse model of the disease, the collagen-induced arthritis (CIA) model. This beneficial effect of IFN-β was confirmed in the examples below.

The invention also relates to the use of a combination of an inhibitor of IL-18 production and/or action and an interferon in the manufacture of a medicament for the treatment of arthritis, in particular rheumatoid arthritis.

Interferons may be conjugated to polymers in order to improve the stability of the proteins. A conjugate between Interferon β and the polyol Polyethlyenglycol (PEG) has been described in W099/55377, for instance.

The inhibitor of IL-18 production and/or action is preferably used simultaneously, sequentially, or separately with the interferon.

In another preferred embodiment of the invention, the interferon is Interferon-β (IFN-β), more preferable IFN-β 1a.

The invention further relates to the use of a combination of IL-18 inhibitors, interferons and TNF antagonists. The combination is suitable for the for the treatment and/or prevention of arthritis, in particular rheumatoid arthritis, and for the treatment and/or prevention of liver injury. The active components may be used simultaneously, sequentially, or separately.

The invention further relates to the use of an expression vector comprising a coding sequence of an inhibitor of IL-18 in the preparation of a medicament for the prevention and/or treatment of arthritic conditions or arthritis, in particular rheumatoid arthritis, or for the treatment of liver injury. A gene therapeutical approach is thus used for treating and/or preventing the disease. Advantageously, the expression of the IL-18 inhibitor will then be in situ, thus efficiently blocking IL-18 directly in the tissue(s) or cells affected by the disease.

In order to treat and/or prevent arthritis, the gene therapy vector comprising the sequence of an inhibitor of IL-18 production and/or action may be injected directly into the diseased joint, for example, thus avoiding problems usually involved in systemic administration of gene therapy vectors, like dilution of the vectors, reaching of the target cells and side effects.

The use of a vector for inducing and/or enhancing the endogenous production of an inhibitor of IL-18 in a cell normally silent for expression of an IL-18 inhibitor, or which expresses amounts of the inhibitor which are not sufficient are also contemplated according to the invention. The vector may comprise regulatory sequences functional in the cells desired to express the inhibitor or IL-18. Such regulatory sequences may be promoters or enhancers, for example. The regulatory sequence may then be introduced into the right locus of the genome by homologous recombination, thus operably linking the regulatory sequence with the gene, the expression of which is required to be induced or enhanced. The technology is usually referred to as endogenous gene activation (EGA), and it is described e.g. in WO 91/09955. It will be understood by the person skilled in the art that it is also possible to shut down IL-18 expression using this technique, by introducing a negative regulation element, like e.g. a silencing element, into the gene locus of IL-18, thus leading to down-regulation or prevention of IL-18 expression. The person skilled in the art will understand that such down-regulation or silencing of IL-18 expression has the same effect as using an IL-18 inhibitor in order to prevent and/or treat disease.

The invention further relates to pharmaceutical compositions for prevention and/or treatment of inflammatory arthritis or liver injury, comprising an inhibitor of IL-18. The composition may comprise antibodies against IL-18, antibodies against any of the IL-18 receptor subunits, inhibitors of the IL-18 signalling pathway, antagonists of IL-18 which compete with IL-18 and block the IL-18 receptor, and IL-18 binding proteins, isoforms, muteins, fused proteins, functional derivatives, active fractions or circularly permutated derivatives thereof having the same activity.

IL-18BP and its isoforms, muteins, fused proteins, functional derivatives, active fractions or circularly permutated derivatives as described above are the preferred active ingredients of the pharmaceutical compositions.

In a further preferred embodiment, the pharmaceutical composition further comprises an interferon, preferably IFN-β.

In yet another preferred embodiment, the pharmaceutical composition comprises a TNF antagonist. Advantageously, anti-TNF antibodies neutralising TNF action are used. Highly preferred are TBPI and TPBII as TNF antagonists.

The active ingredients of the pharmaceutical composition according to the invention, i.e. the IL-18 inhibitor and/or interferon and/or TNF antagonist can be administered to an individual in a variety of ways. The routes of administration include intradermal, transdermal (e.g. in slow release formulations), intramuscular, intraperitoneal, intravenous, subcutaneous, oral, epidural, topical, and intranasal routes. Any other therapeutically efficacious route of administration can be used, for example absorption through epithelial or endothelial tissues or by gene therapy wherein a DNA molecule encoding the active agent is administered to the patient (e.g. via a vector) which causes the active agent to be expressed and secreted in vivo. In addition, the protein(s) according to the invention can be administered together with other components of biologically active agents such as pharmaceutically acceptable surfactants, excipients, carriers, diluents and vehicles.

The definition of "pharmaceutically acceptable" is meant to encompass any carrier, which does not interfere with effectiveness of the biological activity of the active ingredient and that is not toxic to the host to which it is administered. For example, for parenteral administration, the active protein(s) may be formulated in a unit dosage form for injection in vehicles such as saline, dextrose solution, serum albumin and Ringer's solution.

For parenteral (e.g. intravenous, subcutaneous, intramuscular) administration, the active protein(s) can be formulated as a solution, suspension, emulsion or lyophilised powder in association with a pharmaceutically acceptable parenteral vehicle (e.g. water, saline, dextrose solution) and additives that maintain isotonicity (e.g. mannitol) or chemical stability (e.g. preservatives and buffers). The formulation is sterilized by commonly used techniques.

The bioavailability of the active protein(s) according to the invention can also be ameliorated by using conjugation procedures which increase the half-life of the molecule in the human body, for example linking the molecule to polyethylenglycol, as described in the PCT Patent Application WO 92/13095.

The therapeutically effective amounts of the active protein(s) will be a function of many variables, including the type of antagonist, the affinity of the antagonist for IL-18, any residual cytotoxic activity exhibited by the antagonists, the route of administration, the clinical condition of the patient (including the desirability of maintaining a non-toxic level of endogenous IL-18 activity.

A "therapeutically effective amount" is such that when administered, the IL-18 inhibitor results in inhibition of the biological activity of IL-18. The dosage administered, as single or multiple doses, to an individual will vary depending upon a variety of factors, including IL-18 inhibitor pharmacokinetic properties, the route of administration, patient conditions and characteristics (sex, age, body weight, health, size), extent of symptoms, concurrent treatments, frequency of treatment and the effect desired. Adjustment and manipulation of established dosage ranges are well within the ability of those skilled in the art, as well as in vitro and in vivo methods of determining the inhibition of IL-18 in an individual.

According to the invention, the inhibitor of IL-18 is used in an amount ranging between about 0.1 to 5000 µg/kg of body weight or about 1 to 1000 µg/kg of body weight. Amounts of about 10 to 500 µg/kg of body weight are preferred, and amounts of about 50 to 250 µg/kg of body weight are further preferred.

Inhibitors of IL-18 may also be used used in an amount of about 1 to 50 µg/kg of body weight.

The route of administration which is preferred according to the invention is administration by subcutaneous route. Intramuscular administration is further preferred according to the invention.

In further preferred embodiments, the inhibitor of IL-18 is administered daily or every other day.

The daily doses are usually given in divided doses or in sustained release form effective to obtain the desired results. Second or subsequent administrations can be performed at a dosage which is the same, less than or greater than the initial or previous dose administered to the individual. A second or subsequent administration can be administered during or prior to onset of the disease.

According to the invention, the IL-18 inhibitor can be administered prophylactically or therapeutically to an individual prior to, simultaneously or sequentially with other therapeutic regimens or agents (e.g. multiple drug regimens), in a therapeutically effective amount, in particular with an interferon and/or a TNF antagonist. Active agents that are administered simultaneously with other therapeutic agents can be administered in the same or different compositions. Other agents which may be used in combination with IL-18 inhibitors, in particular with IL-18BP, are COX-2 inhibitors. COX-2 inhibitors are know in the art. Specific COX-2 inhibitors are disclosed in WO 01/00229, for example.

The invention further relates to a method for the preparation of a pharmaceutical composition comprising admixing an effective amount of an IL-18 inhibitor with a pharmaceutically acceptable carrier.

Having now described the invention, it will be more readily understood by reference to the following examples that are provided by way of illustration and are not intended to be limiting of the present invention.

EXAMPLES

PART I: Examples 1 to 17: Isolation, Production and Biological Activities of IL-18BP Example 1

Isolation of an IL-18 Binding Protein

*E. coli* IL-18 (2.5 mg, Peprotech, NJ) was coupled to Affi-gel-10 (0.5 ml, BioRad), according to the manufacturer's instructions and packed into a column. Crude urinary proteins (1000-fold concentrated, 500 ml) were loaded onto the column at a flow rate of 0.25 ml/min. The column was washed with 250 ml 0.5M NaCl in phosphate buffered saline (PBS). Bound proteins were then eluted with 25 mM citric acid, pH 2.2 and benzamidine (1 mM), immediately neutralized by 1M $Na_2CO_3$. Fractions of 1 ml were collected. The fractions were analyzed by SDS-PAGE and silver staining. The IL-18 binding protein eluted in fractions 2-8 as a ~40,000 Dalton protein (FIG. 1). The ~40 kD band, corresponding to the IL-18BP exhibited a distinct yellow color upon silver staining. The various fractions were analyzed by cross-linking with $^{125}I$-IL-18, SDS-PAGE and autoradiography as described in Example 2. An IL-18 binding protein was found in fractions 2-8, eluted from the IL-18-agarose column (FIG. 2).

Example 2

Cross-linking of Affinity-Purified IL-18BP to Labeled IL-18

Samples (40 µl) of IL-18BP from the affinity purification step were incubated (70 min. at 4° C.) with $^{125}I$-IL-18 (5,000,000 cpm). Disuccinimidyl suberate (DSS), dissolved in dimethyl sulfoxide ($Me_2SO$, 20 mM), was then added to a final concentration of 2 mM and the mixture was left for 20 min. at 4° C. The reaction was stopped by the addition of 1M Tris-HCl pH 7.5, and 1M NaCl to a final concentration of 100 mM. A sample buffer containing Dithiothreitol (DTT, 25 mM final) was added and the mixtures were analyzed by SDS-PAGE (7.5% acrylamide) followed by autoradiography (FIG. 2).

A specific band of molecular weight 58 kD, probably consisting of a ~40 kD protein cross-linked to the ~20 kD $^{125}I$-IL-18, was observed in fractions eluted from the IL-18 affinity column (lanes 2 and 3) but not in the column wash (lane 1), containing all other crude urinary proteins.

Example 3

Protein Sequence Analysis

Eluted fractions from the affinity column of Example 1 were resolved by SDS-PAGE (10% acrylamide) under non-reducing conditions, electroblotted on a PVDF membrane (Pro-Blot, Applied Biosystems, USA). The membrane was stained with coomassie blue, the ~40 kD band was excised and subjected to protein sequence analysis by a Procise microsequencer (Applied Biosystems, USA). The following major sequence was obtained:

```
T-P-V-S-Q-Q-x-x-x-A-A-A  (SEQ ID NO:11)
1 . . . 5 . . . .10 . .
``` wherein x represents a yet undetermined amino acid.
In addition, a minor sequence was obtained:

```
A-x-Y-x-R-I-P-A-x-A-I-A  (SEQ ID NO:15)
1 . . . 5 . . . .10 . .
```

Because of this double sequence it was not possible to obtain a longer sequence data. The minor sequence was identified as a fragment of human defensin, (accession No. p11398) starting at amino acid 65 of defensin. The major sequence could not be associated with any other known protein, as determined by searching all available databases in NCBI and TIGR by the blastp and tblastn search programs.

In order to obtain a longer and more accurate sequence and in order to identify potential cysteine residues, another aliquot of the fraction eluted from the IL-18-agarose column was reduced with DTT in 6 M guanidine HCI, reacted with 4-vinyl pyridine, desalted by a micro-ultrafiltration device (Ultrafree, cutoff 10,000 Daltons, Millipore) and subjected to protein microsequence analysis. After cycle No. 1 of sequencing, the filter was reacted with o-phtalaldehyde to block all N-terminal polypeptides other than Pro. In this way only the major sequence was obtained as follows:

```
                                    (SEQ ID NO:10)
TPVSQXXXAA XASVRSTKDP CPSQPPVFPA AKQCPALEVT
1          10         20         30         40
```

(T=Thr; P=Pro; V=Val; S=Ser; Q=Gln; X=Unknown; A=Ala; R=Arg; K=Lys; D=Asp; C=Cys; F=Phe; L=Leu; E=Glu)

In cycles 6, 7, 8 and 11 a low level of a Thr signal was obtained. Because of this low level we considered it more prudent not to assign a specific amino acid residue at said cycles.

The resulting sequence is significantly different from that of any other known protein, as determined by searching protein databases. However, searching the TIGR database by the tblastn search program provided a cDNA file, denoted THC123801, whose open reading frame (218 codons), when translated contains a sequence highly homologous to that of the N-terminal sequence of IL-18BP. The homology is hereby shown:

```
1  .......TPVSQXXXAAXASVRSTKDPCPSQPPVFPAAKQCPALEVT.      40  (SEQ ID NO: 12)
          | | |   | |  | | | | | | | | | | | | | | | | | | | | | | | | | | | | | | |
51 VTLLVRATXVXQTTTAATASVRSTKDPCPSQPPVFPAAKQCPALEVTWPE   100  (SEQ ID NO: 13)
```

(The upper sequence (1-40) (SEQ ID NO: 12) is that of the IL-18BP isolated according to the invention; the lower sequence (51-100) (SEQ ID NO: 13) is deduced by translation of the cDNA of TIGR file THC123801).

The putative protein sequence, obtained by translating file THC123801, was ambiguous at residues 2 and 4 of the IL-18BP. It confirms the identity of amino acid residues 6, 7 and 8 of IL-18BP as Thr and seems to do so also for residue 11.

Example 4

The IL-18BP is a Glycoprotein

Aliquot (0.3 ml) of eluted fractions of Example 1 were further purified by size exclusion chromatography on a Superose 12 column (1×30 cm, Pharmacia, Sweden). The column was pre-equilibrated and eluted with phosphate buffered saline and sodium azide (0.02%) at a flow rate of 0.5 ml/min. and fractions of 1 min. were collected. The IL-18 binding protein eluted in fractions 20-25 as a ~40,000 Dalton protein, as determined by SDS-PAGE and silver staining. A sample containing the ~40,000 Dalton protein (fraction 23, 50 µl, ~50 ng protein) was reacted with N-glycosidase F (PNGase F, Biolab) according to the manufacturers instructions. Briefly, the aliquot was denatured by boiling in the presence of 5% SDS for 10 min., 10×G7 buffer (2.5 ?l), 10% NP-40 (2.5 µl) and PNGase F (1 µl), 1 h at 37° C. The sample was analyzed by SDS-PAGE (10% acrylamide) under non-reducing conditions and compared with undigested IL-18BP from the same Superose 12 fraction. It was found that the ~40 kD band of IL-18BP disappeared in the PNGase-treated fraction. New bands, corresponding to 30 kD (just above the PNGase band) and 20 kD were obtained. The elimination of the ~40 kD band indicates that this band is an N-glycosylated protein.

Example 5

Blocking of the Biological Activity of IL-18 by IL-18BP

Figure 3A:
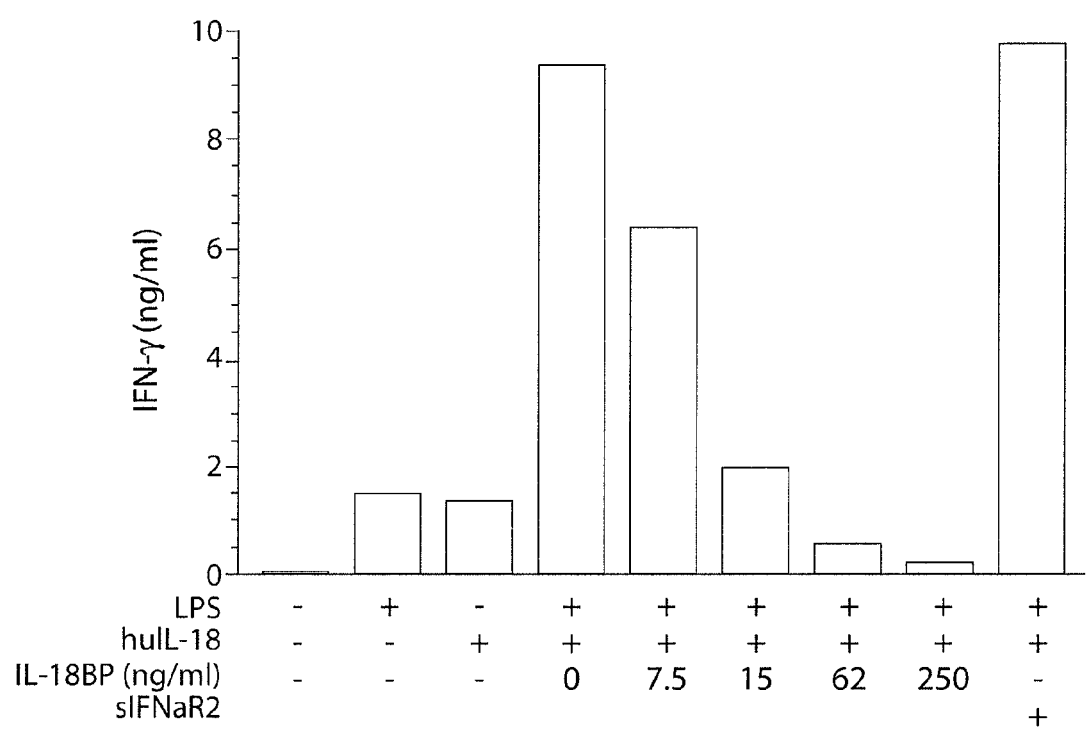
FIG. 3 shows inhibition of IL-18-induced production of IFN-γ by IL-18BP
  (A) Mouse splenocytes were stimulated (24 hr, 37° C.) with the indicated combinations of LPS (1 μg/ml) and human IL-18 (5 ng/ml), added either directly, or after pre-mixing (1 h, 37° C.) with urinary IL-18BP. The level of muIFN-γ in the culture was determined after 24 hr.
  (B) Mouse splenocytes were incubated (24 h) with LPS (1 μg/ml) together with murine IL-18 (10 ng/ml) pre-mixed (1 h, 37° C.) with increasing concentrations of human IL-18BP.
  (C) Mouse splenocytes were incubated (24 h) with LPS (10 μg/ml) together with increasing concentrations of human IL-18BP.
  (D) Mouse splenocytes were incubated (24 h) with Con A (1 μg/ml), together with increasing concentrations of human IL-18BP.
  (E) Human peripheral blood mononuclear cells (PBMC) of three donors were stimulated with IL-12 (10 ng/ml) and huIL-18 (25 ng/ml), added either alone, or after pre-mixing (1 h, 37° C.) with urinary IL-18BP. Human KG-1 cells were stimulated with TNF-α (20 ng/ml) and huIL-18 (25 ng/ml), added either alone, or after pre-mixing (1 h, 37° C.) with urinary IL-18BP.
Figure 3B:
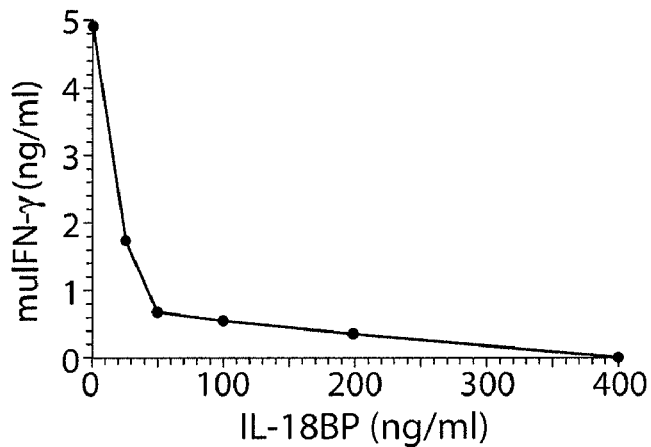
Figure 3C:
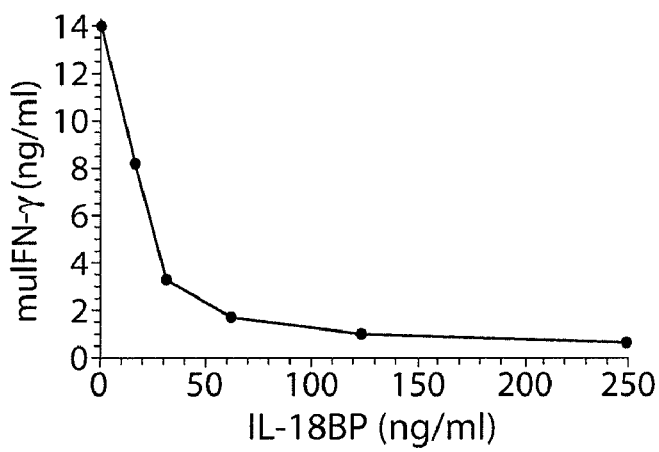
Figure 3D:
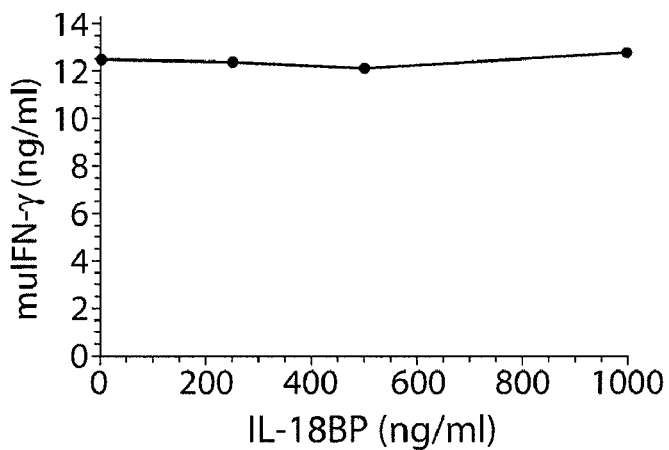
Figure 3E:
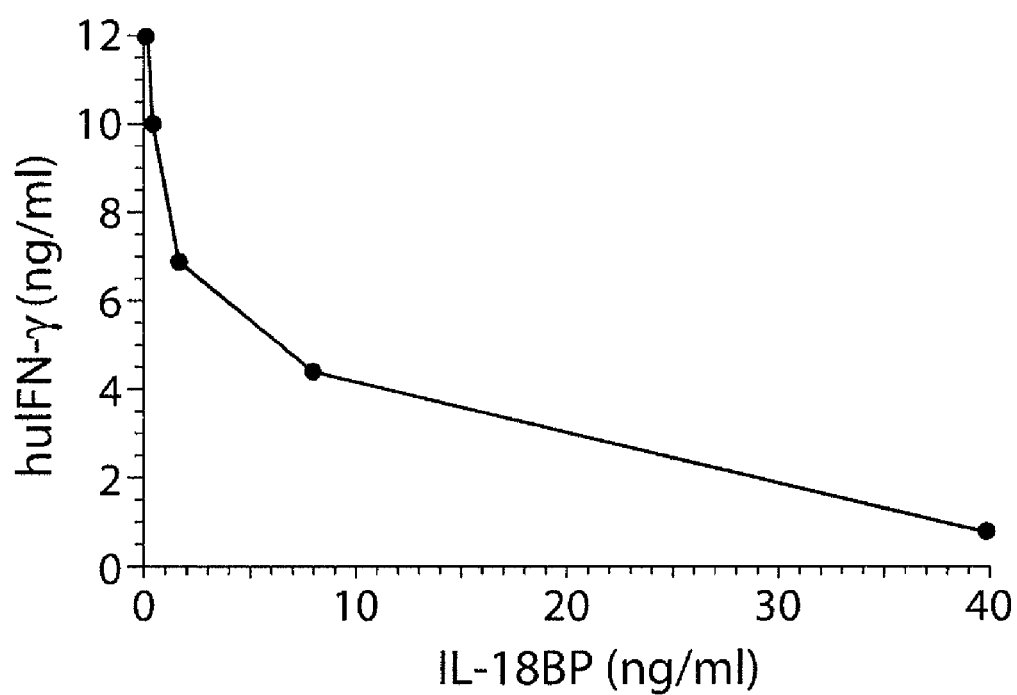
Figure 4A:
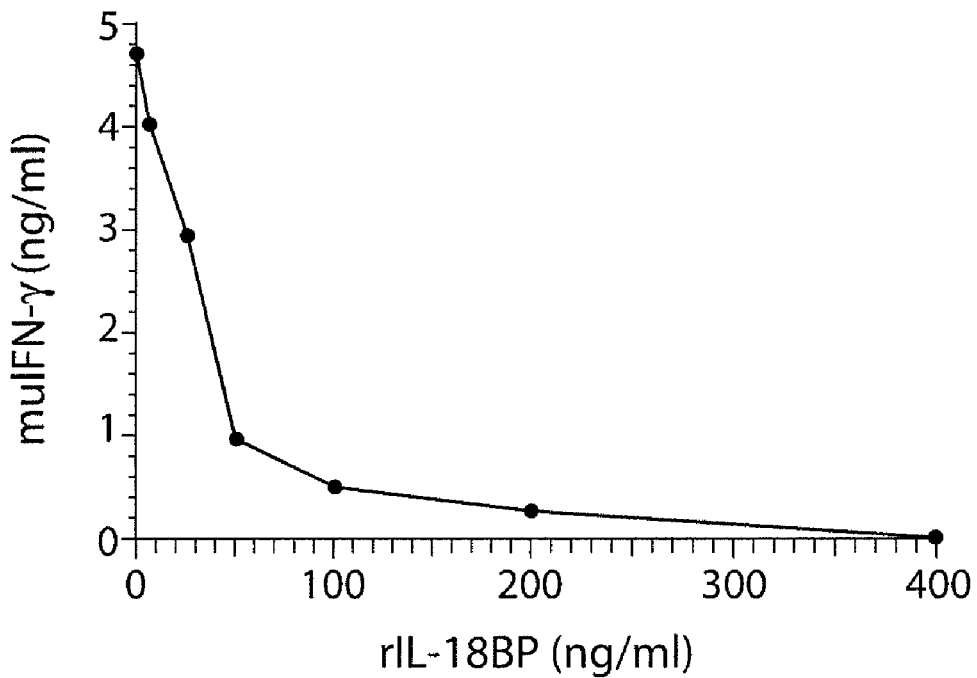
FIG. 4 shows the effect of recombinant IL-18BP on human and mouse IL-18 activity. His$_6$-tagged IL-18BPa was transiently expressed in COS7 cells and purified.
  (A) Human IL-18 (5 ng/ml) was pre-mixed with either His$_6$-tagged-IL-18BPa or RPMI and added to mouse spleen cells together with LPS (1 μg/ml). IFN-γ production was measured after 24 h.
  (B) Mouse IL-18 (10 ng/ml) was pre-mixed with either His$_6$-tagged-IL-18BPa or RPMI and added to mouse spleen cells together with LPS (1 μg/ml). IFN-γ production was measured after 24 h.
  (C) Human IL-18 (25 ng/ml) was pre-mixed with either COS7-IL-18BPa or RPMI and added to Human PBMC in the presence of IL-12 (10 ng/ml).
  (D) Human IL-18 (25 ng/ml) was pre-mixed with either COS7-IL-18BPa or RPMI and added to Human KG-1 cells in the presence of TNF-α (20 ng/ml).
Figure 4B:
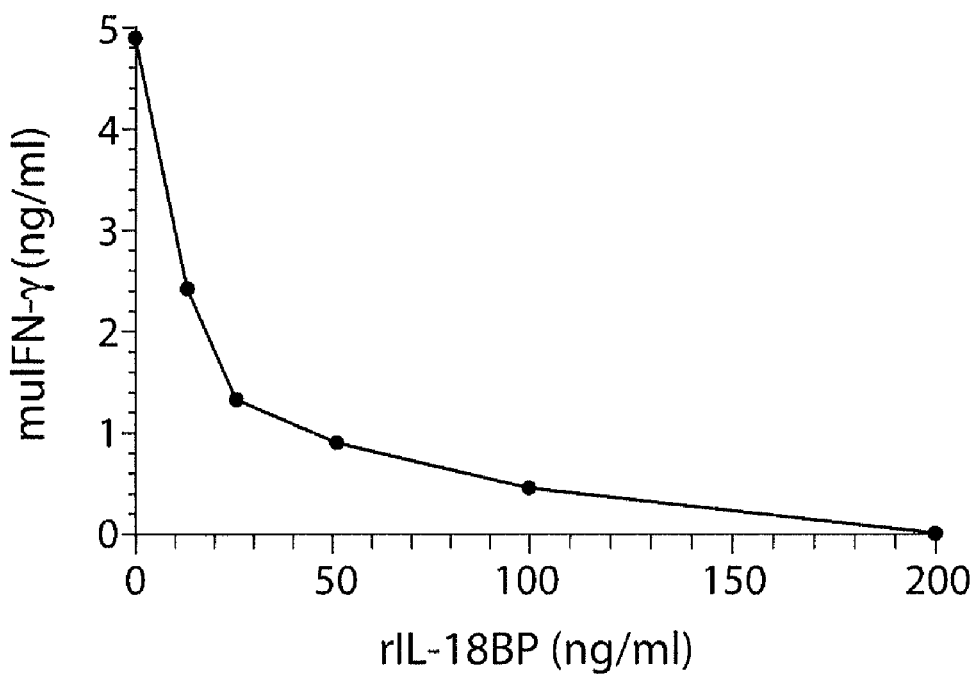
Figure 4C:
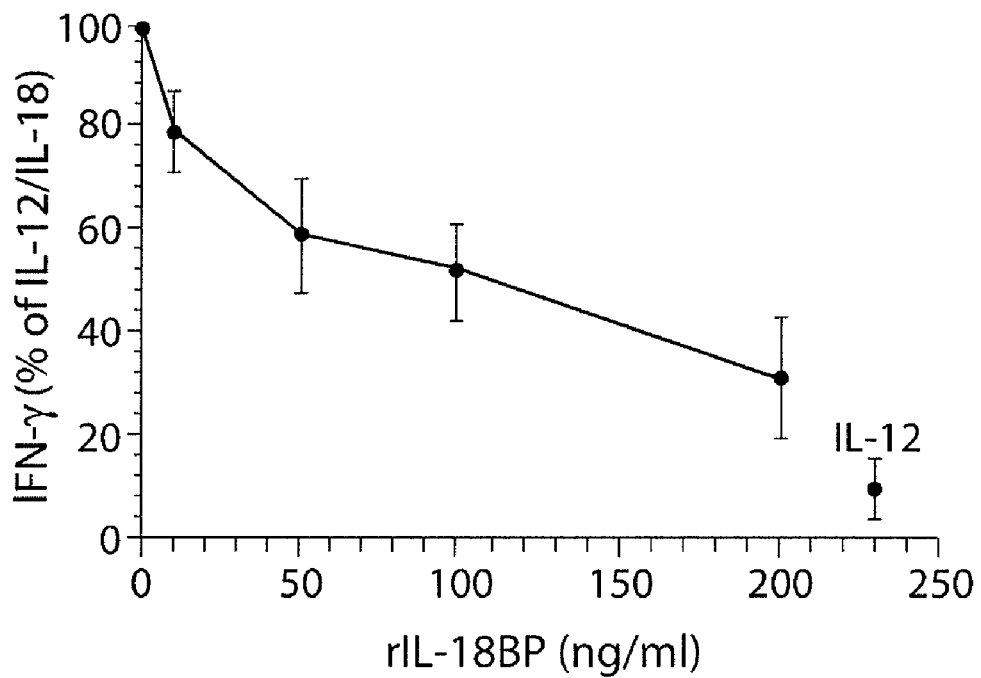
Figure 4D:
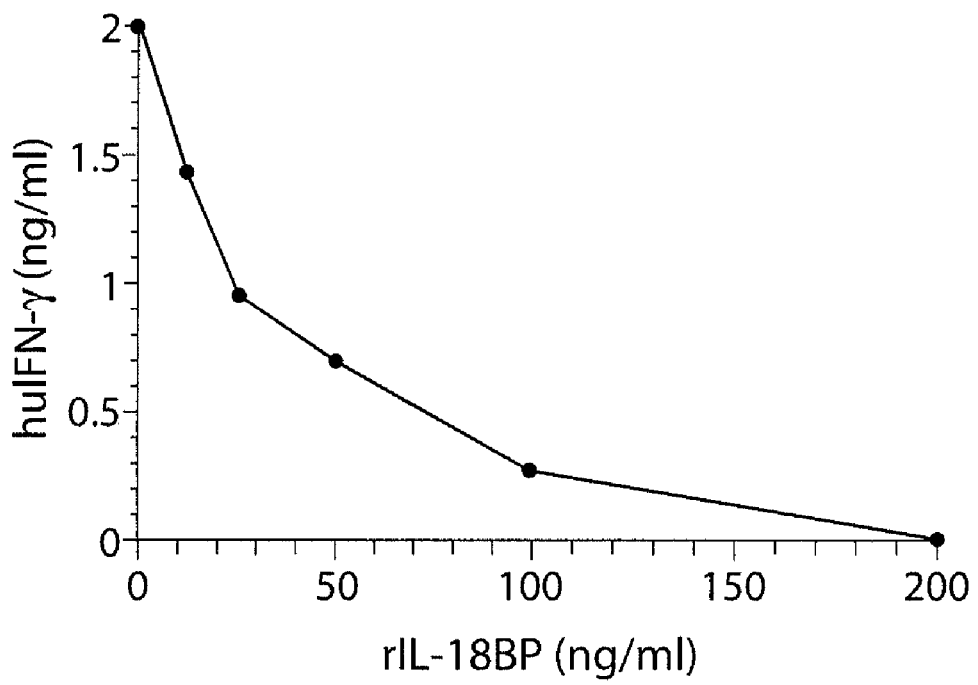

The ability of the IL-18BP isolated from urine to block IL-18 activity was determined by measuring the IL-18-induced production of IFN-γ in mononuclear cells. IL-18 induces IFN-γ when added together with either low concentration of LPS, IL-12, IL-2, or other stimulants. The activity of IL-18 was tested in murine splenocytes, in human peripheral blood mononuclear cells (PBMC) and in the human KG-1 cell line. Spleen cells were prepared from a healthy mouse, washed and suspended in RPMI 1640 medium supplemented with 10% fetal bovine serum at $5×10^6$ cells/ml. 1.0 ml cultures were stimulated with LPS (either 0.5 or 1 µg/ml) together with recombinant human or murine IL-18 (either 0.5 or 5 ng/ml). Human IL-18 binding protein (0, 5 or 50 ng/ml) was added to the recombinant IL-18 before adding to spleen cells. After culturing for 24 h, the spleen cells were subjected to three freeze (−70° C.) and thaw (room temperature) cycles, the cellular debris was removed by centrifugation and the supernatants were assayed for IFN-γ using the ELISA kits for mouse IFN-γ (Endogen). As shown in FIG. 3A, IL-18BP blocked the activity of huIL-18 in murine splenocytes in a dose-dependent manner. In contrast, as a control, soluble interferon-α/β receptor had no effect. The activity of recombinant murine IL-18 was similarly inhibited by the human IL-18BP, suggesting that human IL-18BP recognizes murine IL-18 (FIG. 3B). Endogenous IL-18 is induced in murine splenocytes by high concentrations of LPS, leading to production of IFN-γ. Indeed, IFN-γ induction by LPS (10 µg/ml) was also inhibited by the urinary IL-18BP (FIG. 3C). Concanavalin A (con A) activates T-cells to produce IFN-γ in the absence of IL-18 (Fantuzzi et al., 1998). Indeed, induction of IFN-γ by Con A was not inhibited by IL-18BP even at high concentrations (FIG. 3D). This observation demonstrated that IL-18BP was a specific inhibitor of IL-18 bioactivity rather than a non-specific inhibitor of IFN-γ production. IL-18BP also inhibited the activity of human IL-18 in human KG-1 cells induced by a combination of IL-18 and TNF-α (FIG. 3E).

The above data demonstrate that urinary IL-18BP inhibits human as well as murine IL-18 activity as measured by co-induction of IFN-γ in human and murine mononuclear cells. The concentration of IL-18BP which reduced IL-18 activity by >90% was comparable to that of IL-18 itself, suggesting a high affinity interaction between these two proteins.

Example 6

Isolation of cDNA Clones Coding for IL-18BP.

Total RNA from Jurkat T-cells (CRL 8163, American Type Culture Collection) was reverse-transcribed with SuperScript RNase H-reverse transcriptase (Gibco-BRL) and random primers (Promega, Madison Wis.). The resulting cDNA fragments were then amplified by PCR, using Taq DNA polymerase (Sigma) and primers corresponding to TIGR clone THC123801 nucleotides 24-44 (sense) and 500-481 (reverse). The amplification was done in 30 cycles of annealing (55° C., 2 min) and extension (70° C., 1 min). The resulting PCR products were resolved by agarose (1%) gel electrophoresis, eluted and cloned into pGEM-Teasy TA cloning vector (Promega). DNA from individual clones was sequenced with T7 and SP6 primers.

The resulting 477 bp fragment was $^{32}$P-labeled by random priming. This probe was used for screening various human cDNA and genomic libraries. Duplicate nitrocellulose filters were lifted and hybridized with the probe at 60° C. in a buffer consisting of 6×SSC, 10× Denhardt's solution, 0.1% SDS and 100 µg/ml Salmon sperm DNA. The filters were washed and exposed overnight at −80° C. to Kodak XAR film. Double positive clones were plaque-purified. Plasmids were excised from the λpCEV9 clones and self-ligated. cDNA clones from other libraries were isolated according to the manufacturer's instructions. Automated DNA sequence analysis of the isolated clones was performed with Models 373A and 377 sequencers (Applied Biosystems) using sense and antisense primers. Standard protocols were used for these cloning procedures (Sambrook et al., 1989).

The following libraries were screened: a human monocyte cDNA library, constructed in λpCEV9 cloning vector (Gutkind, 1991), kindly provided by T. Miki; a human Jurkat leukemic T-cell cDNA library, a human peripheral blood leukocyte cDNA library and a human spleen cDNA library, all from Clontech (Palo Alto, Calif.). A human placenta genomic library in lambda FIX II vector was from Stratagene (La Jolla, Calif.).

All cDNA clones corresponded to four different IL-18BP splice variants were obtained and characterized. All splice variants coded for putative soluble secreted proteins. The most abundant one (IL-18BPa) had an open reading frame of 192 codons, coding for a signal peptide of 28 amino acid residues followed by a mature putative IL-18BPa, whose first 40 residues (SEQ ID NO:10) matched perfectly with the N-terminal protein sequence of the urinary IL-18BP (SEQ ID NO:2). The position of the cysteine residues suggested that this polypeptide belongs to the immunoglobulin (Ig) superfamily. Each of the four Gln residues within mature IL-18BPa was a potential N-glycosylation site. The other three splice variants of IL-18BP were significantly less abundant.

Another 1 kb IL-18BPb cDNA coded for a mature protein of 85 amino acid residues (SEQ ID NO:4). A third variant, IL-18BPc, was represented by a 2.3 kb cDNA, coding for a mature IL-18BP of 169 amino acid residues (SEQ ID NO:6). The fourth variant, IL-18BPd coded for a mature IL-18BP of 133 amino acid residues (SEQ ID NO:8). In-exon splicing occurred at two sites along the pro-mRNA. These events and an additional 5' exon in IL-18BPd gave rise to 3 different 5' UTRs in the various cDNA clones. It is therefore quite possible that different IL-18BP variants may be generated in response to distinct transcription regulation signals.

No cDNA coding for a receptor with a transmembrane domain was found so far.

Example 7

Construction of a Mammalian Expression Vector, Production of Recombinant IL-18BP, and Evaluation of the Biological Activities of Recombinant IL-18BP.

The coding region of the IL-18BPa cDNA was amplified by PCR with the sense primer 5 ' TATATCTAGAGCCAC-CATGAGACACAACTGGACACCA (SEQ ID NO: 16) and the reverse primer:

5 ' ATATCTAGATTAATGATGATGATGAT-GATGACCCTGCTGCTGTGGACTGC (SEQ ID NO:17 )

The PCR products were cut with Xba I and cloned into the Xba I site of the pEF-BOS expression vector (25), to yield pEF-BOS-IL-18BPa. The constructs were confirmed by DNA sequencing.

Batches of 6×10$^7$ COS7 cells in 1.4 ml TD buffer, containing pEF-BOS-IL-18BPa plasmid DNA (10 µg) and DEAE-dextran (120 µg) were incubated for 30 min at room temperature, as described (Sampayrat and Dana, 1981). The cells were then washed with DMEM-10% FBS, plated for 4 hr in DMEM-10, washed and incubated for 3-5 days in serum-free DMEM. Culture medium was collected, concentrated 6-fold by ultrafiltration (10 kD cutoff) and the IL-18BP-His$_6$ was isolated on a Talon column (Clontech) with imidazole as eluant according to the manufacturer's instructions.

Immunological cross-reactivity of the urinary and the COS7-expressed IL-18BP was assessed as follows: Urinary IL-18BP (5 µg) was labeled with $^{125}$I by the chloramine T procedure. Supernatants of COS7 cells (250 µl) were mixed (1 h, room temperature final volume 500 µl) with the antibody to urinary IL-18BP, diluted 1:1000 in phosphate-buffered saline (PBS), 0.05% Tween 20 and 0.5% bovine serum albumin (Wash Buffer). $^{125}$I-labeled urinary IL-18BP (10$^6$ cpm) was then added and after 1 h protein G-sepharose (20 µl) was added. The mixture was suspended (1.5 h, 4° C.), the beads were then isolated and washed wash 3× Wash Buffer and once in PBS. The beads were then eluted with a Sample buffer, resolved by SDS-PAGE (10% acrylamide under reducing conditions followed by Autoradiography.

IL-18BPa ran as a single band upon SDS-PAGE with silver staining under reducing and non-reducing conditions and had the same apparent molecular mass as that of the urinary IL-18BP (data not shown). Protein sequence analysis of this preparation revealed the same N-terminal sequence as that of the urinary IL-18BP, indicating that the latter was not degraded at its N-terminus.

Immunoblot analysis of IL-18BPa with antibodies raised against the urinary IL-18BP revealed the same molecular mass band as that of the urinary protein. Furthermore, using immunoprecipitation followed by SDS-PAGE and autoradiography, IL-18BPa was able to displace urinary $^{125}$I-IL-18BP from binding to the antibody. Therefore, IL-18BPa corresponds structurally to the urinary IL-18BP.

Crude and purified IL-18BPa was tested for its ability to inhibit the biological activity of IL-18. IL-18BPa inhibited in a dose dependent manner the IFN-γ inducing activity of human and mouse IL-18 in murine splenocytes, PBMC and the human KG-1 cell line (FIG. 4).

The results of the various bioassays as well as the mobility shift assay (Example 8) demonstrated that inhibition of IL-18 activity is an intrinsic property of the cloned IL-18BP and not that of any accompanying impurities in urinary IL-18BP, such as the co-eluting fragment of defensin.

Example 8

Electrophoretic Mobility Shift Assays

The effect of the urinary and the recombinant IL-18BP on IL-18-induced activation of NF-κB in human KG-1 cells was also studied. Human KG-1 cells ($4\times10^6$ in 1 ml RMPI) were stimulated with either huIL-18 (10 ng/ml) or huIL-18 premixed with an IL-18BP (20 min, room temperature). After 20 min at 37° C., cells were washed three times with ice-cold PBS and immediately frozen in liquid nitrogen. Cell pellets were resuspended in three times the packed cell volume in buffer A (20 mM Tris pH 7.6, 0.4M NaCl, 0.2 mM EDTA, glycerol (20% by volume), 1.5 mM MgCl$_2$, 2 mM dithiothreitol (DTT), 0.4 mM PMSF, 1 mM Na$_3$VO$_4$, 2 μg/ml each of leupeptin, pepstatin and aprotinin). Cell debris was removed by centrifugation (15,000×g, 15 min.), aliquots of the supernatant were frozen in liquid nitrogen and stored at −80° C. Protein concentration was determined by a Bradford assay (Bio-Rad) using bovine serum albumin as standard. A double-stranded oligonucleotide corresponding to NF-κB binding element (10 pmol, Promega) was labeled with [$^{32}$P] dCTP (300 Ci/mmol) and T4 polynucleotide kinase (New England Biolabs). Free nucleotides were removed by a spin column. Extracts (10 μg protein) of cells treated with IL-18 or IL-18 plus IL-18BP were incubated (15 min., room temperature) with the labeled probe ($3\times10^4$ cpm) together with poly dI.dC (500 ng, Pharmacia) and denatured salmon sperm DNA (100 ng, Sigma) in 20 μl buffer consisting of HEPES (pH 7.5, 10 mM), 60 mM KCl, 1 mM MgCl$_2$, 2 mM EDTA, 1 mM DTT and glycerol (5% by volume). The mixtures were then loaded onto 5% non-denaturing polyacrylamide gels. Electrophoresis was performed at 185 V in 0.5×TBE (40 mM Tris HCl, 45 mM boric acid and 2.5 mM EDTA). Gels were vacuum dried and autoradiographed overnight at −80° C. IL-18 was found to induce the formation of the p50 NF-?B homodimer and the p65/p50NF-κB heterodimer. Urinary as well as recombinant IL-18BP inhibited the activation of NF-κB by IL-18, as determined by an electrophoretic mobility shift assay with KG-1 cell extracts binding a radiolabeled oligonucleotide corresponding to the NF-κB consensus sequence.

Example 9

Expression of IL-18BP in *E. coli*, Yeast and Insect Cells

IL-18BP may also be produced by other recombinant cells such as prokaryotic cells, e.g., *E. coli*, or other eukaryotic cells, such as yeast and insect cells. Well known methods are available for constructing appropriate vectors, carrying DNA that codes for either IL-18BP and suitable for transforming *E. coli* and yeast cells, or infecting insect cells in order to produce recombinant IL-18BP. For expression in yeast cells, the DNA coding for IL-18BP (Example 6) is cut out and inserted into expression vectors suitable for transfection of yeast cells. For expression in insect cells, a DNA coding for IL-18BP is inserted into baculovirus and the insect cells are infected with said recombinant baculovirus. For expression in *E. coli*, the DNA coding for IL-18BP is subjected to site directed mutagenesis with appropriate oligonucleotides, so that an initiation ATG codon is inserted just prior to the first codon of mature IL-18BP. Alternatively, such DNA can be prepared by PCR with suitable sense and antisense primers. The resulting cDNA constructs are then inserted into appropriately constructed prokaryotic expression vectors by techniques well known in the art (Manatis, 1982).

Example 10

Construction of Adeno-associated Expression Vector for In Vivo Expression of IL-18BPa A functional gene coding for IL-18BPa is constructed based on plasmid pcDNA3 (Invitrogen, San Diego Calif.). The IL-18BP cDNA with a Kozak consensus sequence at the 5' end is ligated into the Xba I site of pcDNA3 in a way that destroys the restriction site. New Xba I sites are inserted by site-directed mutagenesis before the neomycin cassette (base 2151 of the original pcDNA3 sequence) and after the SV40 polyadenylation signal (base 3372 of the original pcDNA3 sequence). This construct is then cut with Xba I and the resulting 4.7 kb minigen is inserted at the Xba I site of plasmid psub201 as described (Snyder et al, 1996, Current Protocols in Human Genetics, Chapters 12.1.1-12.1.17, John Wiley & Sons). The resulting recombinant plasmid is cotransfected with the helper AAV plasmid pAAV/Ad into human T293 cells. The cultures are then infected with adenovirus as a helper virus and the cells are collected after 48-60 hours of incubation. The cells are subjected to 3 freeze-thaw cycles, cell debris is removed by centrifugation, and the supernatant is brought to 33% saturation with ammonium sulfate. The mixture is then centrifuged and rAAV is precipitated from the supernatant by bringing the ammonium sulfate to 50% saturation. The virus is further purified by CsCl, dialyzed and finally heated for 15 min at 56° C. to destroy any adenovirus.

Example 11

Construction of Recombinant Fusion Proteins of IL-18BP

The production of proteins comprising IL-18BP fused to the constant region of IgG2 heavy chain may be carried out as follows: the DNA of IL-18BP is subjected to site-directed mutagenesis with appropriate oligonucleotides so that a unique restriction site is introduced immediately before and after the coding sequences. A plasmid bearing the constant region of IgG2 heavy chain, e.g. pRKCO42Fc1 (Byrn, 1990) is subjected to similar site-directed mutagenesis to introduce the same unique restriction site as close as possible to Asp 216 of IgG1 heavy chain in a way that allows translation in phase of the fused protein. A dsDNA fragment, consisting of 5' non-translated sequences and encoding for IL-18BP is prepared by digestion at the unique restriction sites or alternatively by PCR with appropriately designed primers. The mutated pRKCD42Fc1 is similarly digested to generate a large fragment containing the plasmid and the IgG1 sequences. The two fragments are then ligated to generate a new plasmid, encoding a polypeptide precursor consisting of IL-18BP and about 227 C-terminal amino acids of IgG1 heavy chain (hinge region and CH2 and CH3 domains). The DNA encoding the fused proteins may be isolated from the plasmid by digestion with appropriate restriction enzymes and then inserted into efficient prokaryotic or eukaryotic expression vectors.

Example 12

Production of Chemically Modified IL-18BPs

In order to increase the half-life of the IL-18BPs in plasma, IL-18BPs which are chemically modified with polyethylene glycol (PEG) may be made. The modification may be done by cross linking PEG to a cysteine residue of the IL-18BP molecules. Mutant IL-18BPs may be constructed which contain an extra cysteine residue at the amino terminus, glycosylation sites, and the carboxyl terminus of each IL-18BP. The mutagenesis may be carried out by PCR using oligonucleotides containing the desired mutation. These mutant proteins are expressed in the usual manner as well known in the art. Pegylation of these proteins will be carried out and the activity will be assessed.

Example 13

Preparation of Polyclonal Antibodies to IL-18BP

Rabbits were initially injected subcutaneously with 5 μg of a pure preparation of the urinary IL-18BP, emulsified in complete Freund's adjuvant. Three weeks later, they were injected again subcutaneously with 5 μg of the IL-18BP preparation in incomplete Freund's adjuvant. Two additional injections of IL-18BP as solution in PBS were given at 10 day intervals. The rabbits were bled 10 days after the last immunization. The development of antibody level was followed by a radioimmunoassay. $^{125}$I-labeled IL-18BP (166,000 cpm) was mixed with various dilutions (1:50, 1:500, 1:5,000 and 1:50,000) of the rabbit serum. A suspension of protein-G agarose beads (20 μl, Pharmacia) was added in a total volume of 200 μl. The mixture was left for 1 hour at room temperature, the beads were then washed 3 times and bound radioactivity was counted. Rabbit antiserum to human leptin was used as a negative control. The titer of the IL-18R antiserum was between 1:500 and 1:5000, while that of the negative control was less than 1:50.

Example 14

Preparation of Monoclonal Antibodies to IL-18BP

Female Balb/C mice (3 months old) are first injected with 2 μg purified IL-18BP in an emulsion of complete Freund's adjuvant, and three weeks later, subcutaneously in incomplete Freund's adjuvant. Three additional injections are given at 10 day intervals, subcutaneously in PBS. Final boosts are given intraperitoneally 4 and 3 days before the fusion to the mouse showing the highest binding titer as determined by IRIA (see below). Fusion is performed using NSO/1 myeloma cell line and lymphocytes prepared from both the spleen and lymph nodes of the animal as fusion partners. The fused cells are distributed into microculture plates and the hybridomas are selected in DMEM supplemented with HAT and 15% horse serum. Hybridomas that are found to produce antibodies to IL-18BP are subcloned by the limiting dilution method and injected into Balb/C mice that had been primed with pristane for the production of ascites. The isotypes of the antibodies are defined with the use of a commercially available ELISA kit (Amersham, UK).

The screening of hybridomas producing anti-IL-18BP monoclonal antibodies is performed as follows: Hybridoma supernatants are tested for the presence of anti-IL-18BP antibodies by an inverted solid phase radioimmunoassay (IRIA). ELISA plates (Dynatech Laboratories, Alexandria, Va.) are coated with Talon-purified IL-18BPa-His6 (10 μg/ml, 100 μl/well). Following overnight incubation at 4° C., the plates are washed twice with PBS containing BSA (0.5%) and Tween 20 (0.05%) and blocked in washing solution for at least 2 hrs at 37° C. Hybridoma culture supernatants (100 μl/well) are added and the plates are incubated for 4 hrs at 37° C. The plates are washed 3 times and a conjugate of goat-anti-mouse horseradish peroxidase (HRP, Jackson Labs, 1:10,000, 100 μl/well) is added for 2 hrs at room temperature. The plates are washed 4 times and the color is developed by ABTS (2,2'-azino-bis (3-ethylbenzthiazoline-6-sulfonic acid, Sigma) with $H_2O_2$ as a substrate. The plates are read by an automatic ELISA reader. Samples giving OD that are at least 5 times higher than the negative control value are considered positive.

Example 15

Affinity Chromatography of IL-18BP with Monoclonal Antibodies

Antibodies against IL-18BP are utilized for the purification of IL-18BP by affinity chromatography. Ascitic fluid containing the monoclonal antibody secreted by the hybridoma is purified by ammonium sulfate precipitation at 50% saturation followed by extensive dialysis against PBS. About 10 mg of immunoglobulins are bound to 1 ml Affigel 10 (BioRad USA), as specified by the manufacturer.

250 ml of human urinary proteins (equivalent to 250 I of crude urine) are loaded on 0.5 ml of the anti IL-18BP antibody column at 4° C. at a flow rate of 0.25 ml/min. The column is washed with PBS until no protein is detected in the washings. IL-18BP is eluted by 25 mM citric acid buffer, pH 2.2 (8×1 column volume fractions) and immediately neutralized by 1 M $Na_2CO_3$. Further purification of this preparation is obtained by size exclusion chromatography.

Example 16

ELISA Test

Microtiter plates (Dynatech or Maxisorb, by Nunc) are coated with anti-IL-18BP monoclonal antibody (serum free hybridoma supernatant or ascitic fluid immunoglobulins) overnight at 4° C. The plates are washed with PBS containing BSA (0.5%) and Tween 20 (0.05%) and blocked in the same solution for at least 2 hrs at 37° C. The tested samples are diluted in the blocking solution and added to the wells (100 μl/well) for 4 hrs at 37° C. The plates are then washed 3 times with PBS containing Tween 20 (0.05%) followed by the addition of rabbit anti-IL-18BP serum (1:1000, 100 μl/well) for further incubation overnight at 4° C. The plates are washed 3 times and a conjugate of goat-anti-rabbit horseradish peroxidase (HRP, Jackson Labs, 1:10,000, 100 μl/well) was added for 2 hrs at room temperature. The plates were washed 4 times and the color is developed by ABTS (2,2'-azino-bis (3-ethylbenzthiazoline-6-sulfonic acid, Sigma) with $H_2O_2$ as a substrate. The plates are read by an automatic ELISA reader.

Example 17

Non-Glycosylated Human IL-18BP is Biologically Active

Purified recombinant IL-18BPa was tested for its ability to inhibit the biological activity of IL-18. IL-18BPa inhibited in a dose dependent manner the IFN-γ inducing activity of human and mouse IL-18 in murine splenocytes, PBMC and the human KG-1 cell line (FIG. 4).

Purified IL-18BPa having an $His_6$ tag at the C-terminus (1.5 μg, 50 μl) was adjusted to pH 7.5 and mixed with N-glycosidase F (3 μl, 500,000 U/ml, PNGase F, New England Biolabs). The mixture was incubated for 24 h at 37° C. under non-denaturing conditions. Aliquots from the sample and from undigested IL-18BP-$His_6$ were analyzed by SDS-PAGE under non-reducing conditions followed by immunoblotting with antibodies to IL-18PB. It was found that the ~40 kD band of IL-18BP-$His_6$ disappeared in the PNGase-treated fraction and a new ~20 kD band was obtained. The molecular mass of the product and the specificity of PNGase F indicated that IL-18BP-$His_6$ was fully deglycosylated.

The PNGase-treated fraction, undigested IL-18BP-$His_6$ and control sample containing PNGase in buffer were absorbed separately on Talon beads, washed with phosphate buffer and eluted with imidazole (100 mM). The eluted fractions were subjected to bioassay using human IL-18 (20 ng/ml), LPS (2 μg/ml) and murine splenocytes. The results are shown in the following table:

| Sample | IFN-? (ng/ml) |
| --- | --- |
| Control | 7.5 |
| Non-digested IL-18BP-$His_6$ | 0 |
| PNGase-treated IL-18BP-$His_6$ | 0 |

Therefore, it is concluded that deglycosylated IL-18BP is biologically active as a modulator of IL-18 activity.

PART II: Examples 18 to 25, Relating to the use of IL-18 Inhibitors in Liver Injury

Example 18

Production of IL-18BP-His Tag

Purified recombinant human IL18BP containing a his-tag (r-hIL-18BP-His tag) was produced in CHO cells. The production of recombinant proteins in eukaryotic cells is known by the person skilled in the art. Well known methods are available for constructing appropriate vectors, carrying DNA that codes for IL-18BP and suitable for transfection of eukaryotic cells in order to produce recombinant IL-18BP. For expression in cells, the DNA coding for IL-18BP (see, e.g. (Novick et al., 1999) is cut out and inserted into expression vectors suitable for transfection of cells. Alternatively, such DNA can be prepared by PCR with suitable sense and antisense primers. The resulting cDNA constructs are then inserted into appropriately constructed eukaryotic expression vectors by techniques well known in the art (Manaitis, 1982). The recombinant protein was purified to over 95% purity and found to be biologically active in-vitro and in-vivo with a high affinity to its ligand.

Example 19

Protective Effect of IL18BP Against Endotoxin-induced Death in the Murine Model

A murine model was used to test whether IL18BP, an inhibitor of IL-18, would protect mice against a high dose of lipopolysaccharides (LPS). LPS elicits acute liver injury, followed by rapid death of the mice.

4 mg/kg of recombinant, human IL-18BP (rhIL18BPhis) containing a his-tag (resulting from recombinant production of the protein) was injected intraperitoneally (i.p). into C57BL/6 mice. 1 h later, 60 mg/kg LPS were injected (lethal doses). The survival of mice was compared to a group of animals who received LPS alone (no IL18BP).

Five out of 7 mice injected with rhIL-18BP-his survived the LPS injection in contrast to the control mice, in which all animals died within 3 days.

Figure 5:
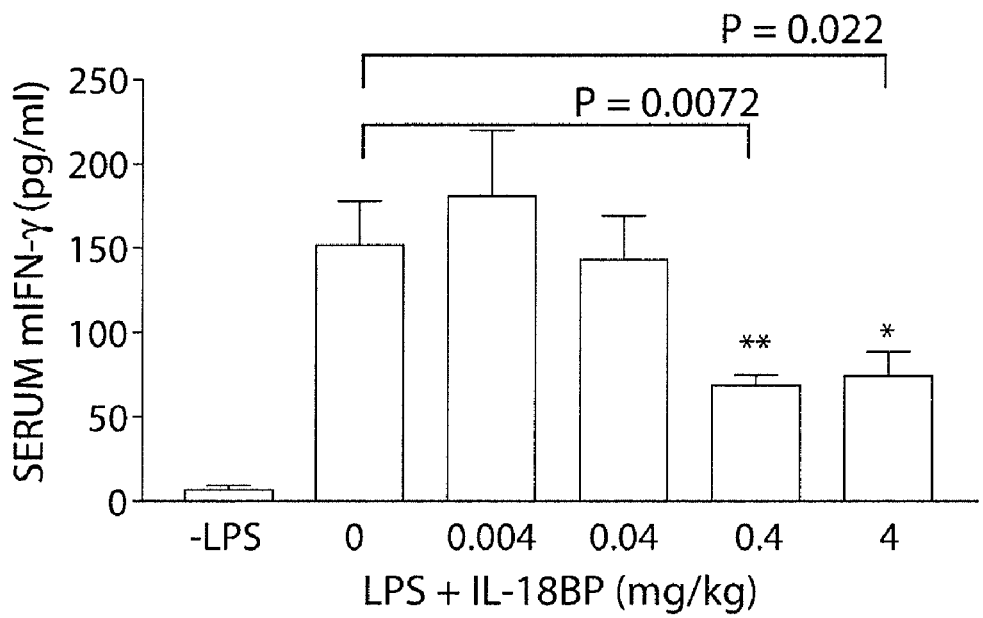
FIG. 5 shows a histogram depicting the serum levels of IFN-γ (pg/ml) after injection of various amounts of recombinant IL18BP (0; 0,04; 0,4; 4 mg/kg) into mice 1 h before the injection of LPS. Blood samples were taken 5 h after LPS injection and analyzed by ELISA for circulating IFN-γ.

Blood samples were taken 5 h after the LPS injection in the absence or presence of increasing doses of rhIL-18BP-his and analyzed by ELISA for circulating IFN-γ (FIG. 5). 0.4 and 4 mg/kg rhIL-18BP induced a 2 fold reduction in serum IFN-γ. This inhibition was lost at lower doses of rhIL-18BP (0.004 and 0.4 mg/kg).

Example 20

IL18BP has a Protective Effect Against Liver Injury in a Murine Model

A mouse model of fulminant hepatitis was used to test the effect of IL18BP. Mice develop acute liver injury when subjected to a sequential administration of Propionibacterium acnes (P. acnes) and lipopolysaccharide (LPS).

Figure 6:
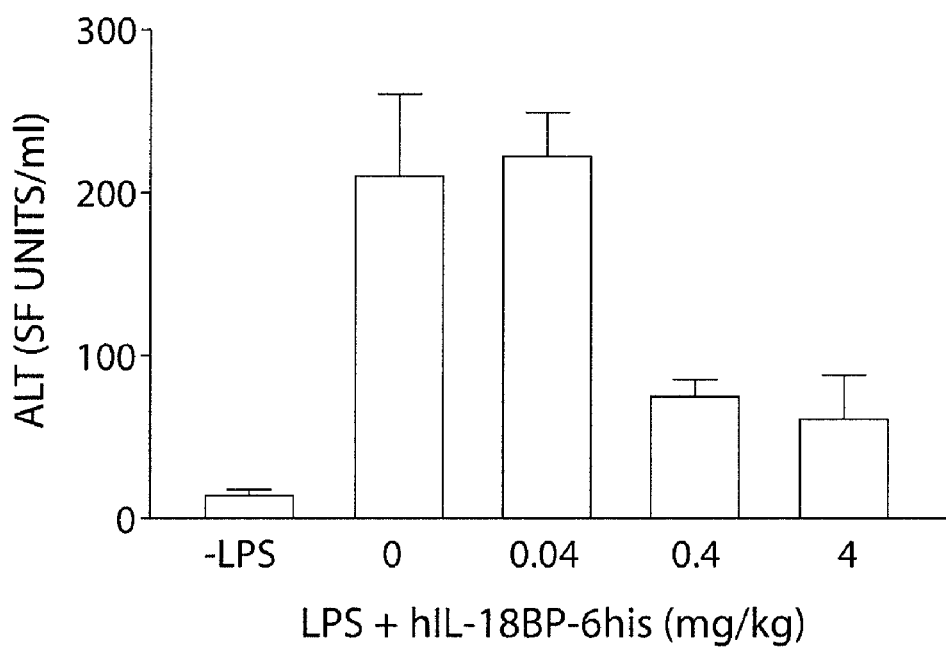
FIG. 6 shows a histogram depicting the serum levels of Alanine aminotransferase. Mice were injected with increasing doses of recombinant human IL18BP (0; 0,04; 0,4; 4 mg/kg) before injection of LPS into P. acnes sensitized mice. Blood samples were taken 5 h after LPS injection and serum levels of Alanine aminotransferase (ALT) were measured.

Mice were injected with increasing doses of rhIL-18BP-his (4; 0.4; 0.04; 0 mg/kg) at various times (1 h, 20 min, simultaneously) before the injection of LPS in C57BL/6 P. acnes sensitized mice. When rhIL-18BP-his was given i.p. at the same time as LPS, none of the mice survived and levels of circulating IFN-γ and TNF-α were unaffected. Surprisingly, rhIL-18BP (4 and 0.4 mg/kg) induced a 70% reduction of circulating Alanine aminotransferase (a marker of liver injury), as shown in FIG. 6.

In addition to this, the survival of mice was monitored (FIG. 7): When rhIL-18BP was given i.p. 20 minutes before LPS, the two highest doses of 11-18BP (4 and 0.4 mg/kg) delayed the death of the mice by 10 h as compared to the control mice who received NaCl instead of IL-18BP.

The results of the measurement of serum IFN-γ levels are shown in FIG. 8. rhIL-18BP (4 mg/kg) inhibited 90% of circulating IFN-γ levels and 80% of circulating Alanine aminotransferase (not shown).

When rhIL-18BP-his was given 1 h before LPS, survival curves and levels of circulating IFN-γ were similar to what was observed when rhIL-18BP-his was given 20 min before LPS, but levels of circulating Alanine aminotransferase were unaffected (not shown).

In addition to this, murine liver tissue was analyzed by hematoxilin-eosine staining, as well as by tunnel microscopy. The livers of mice, in which severe hepatitis had been induced before, showed severe necrosis as compared to normal liver tissue. In contrast to this, liver tissue of mice treated with IL-18BP showed significantly less necrotic foci than untreated mice.

Example 21

Anti-IL-18 Antibodies Protect Against Lethal Endotoxemia

In order to evaluate, whether blockade of IL-18 with IL-18 antibodies would protect mice against lethal doses of bacterial lipopolysaccharides, C57BL/6J mice were first injected with a neutralizing rabbit anti-mouse IL-18 antibody (polyclonal) or normal rabbit serum (NDS) as a control. 30 min after antibody treatment, a lethal dose of LPS derived either from *E. coli* (FIG. 9 A) or *S. thyphimurium* (FIG. 9B) was injected. Experiments involved 10-12 mice/group, and were performed twice on two different occasions.

As shown in FIG. 9A, treatment of the mice with the anti-IL-18 antiserum prevented the mortality induced by 40 mg/kg *E. coli* LPS. 100% of the mice survived after anti-IL-18 treatment vs. 10% survival in mice treated with normal rabbit serum ($p<0.005$).

FIG. 9 B shows that the antibody treated mice were also protected against *S. typhimurium* lethal effects (50% vs. 0% survival; $p<0.05$).

Example 22

Blockade of IL-18 and TNF-α Protects Mice from ConA- and PEA-induced Hepatotoxicity Two experimental models of hepatotoxicity were used to evaluate the role of IL-18 and TNF-α in liver injury. Injection of Concanavalin A (Con A) and Pseudomonas aeruginosa (PEA) into mice both induce liver injury, and are models of T cell mediated hepatitis.

C57BL/6J mice were pretreated with an anti-IL-18 antiserum or a soluble TNF-α receptor, TNFsRp55. Serum Alanine aminotransferase (ALT) levels were measured as indicators of hepatic injury (FIG. 10).

As shown in FIG. 10A, both IL-18 antiserum and soluble TNF-receptors significantly reduced ConA-induced serum ALT levels, as compared to a control injection of the vehicle alone (pyrogen free saline). A co-adminstration of soluble TNF receptor and IL-18 antiserum led to a complete inhibition of Con-A induced liver injury.

As shown in FIG. 10B, in PEA-injected mice, neutralization of either TNF-α inhibitors or anti-IL-18 antibodies resulted in 93% and 83% inhibition of serum ALT levels, respectively. A combined blockade of both resulted in 99% protection.

Example 23

Plasma Levels of IL-18-Binding Protein are Elevated in Patients with Chronic Liver Disease IL-18 BP plasma levels were measured in 133 patients with chronic liver disease (CLD) of varying etiologies and 31 healthy controls by a specific ELISA, using an IL-18BP monoclonal antibody.

Plasma levels of IL-18 BP were significantly higher in CLD patients (12.91 i 0.89 ng/ml; average±SEM) than in healthy subjects (4.96±0.43 ng/ml, $p<0.001$). Cirrhotic patients had signifcantly higher levels than patients with non-cirrhotic CLD (19.23±1.28 ng/ml, n=67, vs. 6.49±0.51 ng/ml, n=66, $p<0.001$). Patients with stage B of the Child-Pugh classification had higher levels of IL-18 BP than those with stage A (22.48±2.44 ng/ml vs. 9.57±1.25 ng/ml, $p<0.001$). However, there was no significant difference between Child B and C (22.48±2.44 ng/ml vs. 20.62±4.75 ng/ml, $p=0.7$). Plasma levels of IL-18 BP correlated positively with GOT, bilirubin and erythrocyte sedimentation rate. Negative correlation was found with prothrombin time.

In conclusion, the results show that IL-18 BP plasma levels are elevated in CLD and correlate with the severity of disease independent of the etiology of disease. Although an endogenous antagonist of the proinflammatory IL-18, increased levels of IL-18 BP seem not to be sufficient to counteract the overwhelming proinflammatory mediators in CLD.

Example 24

Inhibition of Alcoholic hepatitis by IL-18BP

Four groups of rats (5 per group) are fed ethanol and a diet containing corn oil by intragastric infusion for 4 weeks. Dextrose isocalorically replaces ethanol in control rats. The rats are injected daily with mouse IL-18BP (1 mg/kg), or saline. Pathological analysis is performed on liver sections and measurements of liver enzymes in serum, TNF-α, Fas ligand and IFN-γ are taken. Necroinflammatory injury and expression of liver enzymes, TNF-α, Fas ligand, and IFN-γ are seen in the ethanol-fed rats that were injected with saline.

Rats injected with mouse IL-18BP are protected from necroinflammatory injury and the levels of liver enzymes, TNF-α, Fas ligand and IFN-γ are significantly reduced (>90%).

Example 25

Inhibition of Concanavalin A-induced Hepatitis by IL-18BP

Balb/c mice are injected with 12 mg/kg Concanavalin A (Con A) with or without injection of murine IL-18BP (1 mg/kg), 2 h prior to Con A administration and then daily. Liver damage is evaluated by determining serum levels of liver enzymes, TNF-α, Fas ligand and IFN-γ. Hepatic histopathology is compared to mice treated with Concanavalin A only.

Pretreatment with IL-18BP significantly reduces serum levels of liver enzymes and TNF-α with no evidence of inflammation in histopathologic examination compared to control mice treated with Con A.

PART III: Examples 26 and 27 Relating to the use of IL-18 Inhibitors in Arthritis Example 26

Production of IL-18BP-His Tag

For the experiment described in detail in Example 27 below, recombinant human IL-18BP containing a his-tag of 6 residues (r-hIL-18BP-His tag) was produced in CHO cells and purified as described by Kim et al., 2000. The recombinant protein was purified to over 95% purity and found to be biologically active in-vitro and in-vivo with a high affinity to its ligand.

The production of recombinant proteins in other eukaryotic systems, with or without tags facilitating purification of the recombinant proteins, is known by the person skilled in the art. Well known methods are available for constructing appropriate vectors, carrying DNA that codes for IL-18BP and suitable for transfection of eukaryotic cells in order to produce recombinant IL-18BP. For expression in cells, the DNA coding for IL-18BP (see, e.g. Novick et al., 1999) is cut out from the cloning vector and inserted into expression vectors suitable for transfection of cells. Alternatively, such DNA can be prepared by PCR with suitable sense and antisense primers. The resulting cDNA constructs are then inserted into appropriately constructed eukaryotic expression vectors by techniques known in the art (Maniatis et al., 1982).

Example 27

Blockade of Endogenous IL-18 in a Murine Model of Arthritis

Methods

Induction of Collagen-induced Arthritis (CIA)

CIA was induced in male DBA/1 mice (8-12 weeks old) by immunisation with native type 11 bovine collagen (CII) as previously described (Plater-Zyberk et al., 1995). From day 25 post-CII immunisation, mice were examined daily for onset of disease.

Treatment with rhIL-18BP-6 his

Treatment of CII-immunised DBA/1 mice was started on the first appearance of clinical sign of disease. Recombinant, human IL-18BP containing a tag of 6 histidines (rh-IL-18BPa 6his) was used to neutralise endogenous IL18 in the collagen treated mice. rh-IL-18BP-6his was injected daily for 7 seven days at 5 different concentrations 10, 3, 1, 0.5, 0.25 mg/kg/injection intraperitoneally (i.p.). The placebo control mice received the vehicle only (0.9% NaCl).

Assessment of Disease Development

Clinical Evaluation (Clinical Scores)

From first appearance of clinical symptoms, mice were examined every day by an investigator blinded to the treatment. Each limb was graded for disease severity (scores 0-3.5, max score=14/mouse). The progression of edema (inflammation) was measured on the first paws that showed signs of disease using precision calipers (Proctest 2T, Kroeplin Langenmesstechnik)

Disease progression was assessed daily for 8 days post-onset at which time all mice were sacrificed and paws collected for histopathological examination.

Histological assessment of cartilage erosions and microscopical inflammation

At termination of the experiments, i.e. at day 8 post-onset, mice were killed and the paw that first developed sign of disease was dissected away. Joints were fixed, decalcified and embedded in paraffin. Standard sections (5 to 7 µm) of the joints were made and stained with hematoxylin/eosin/Safranin O. Each joint was scored by 2 investigators unaware of the treatment protocol (no destruction of cartilage or bone =0; localised cartilage erosions=1-2; more extended erosions=3; general cartilage destruction and presence of bone erosions=4). The final scores of each mouse was the mean of the result on all the scored joints. Microsopical inflammation or synovitis was scored from 0 to 4, as follows: no inflammation=0; slight thickening of lining layer and/or some infiltrating cells in sublining layer=1-2; thickening of lining layer and/more pronounced influx of cells of sublining layer=3; presence cells in the synovial space and synovium highly infiltrated with many inflammatory cells=4.

Determination of Anti-collagen Antibodies

Antibodies against bovine type II collagen were examined by using an enzyme-linked immunosorbent assay (ELISA). Titers of IgG1 and IgG2a were measured. Briefly, plates were coated with 10 µg of bovine collagen and thereafter-nonspecific binding sites were blocked with 0.1 M ethanolamin (Sigma). Serial 1:2 dilutions of the sera were added followed by incubation with isotype specific goat anti-mouse peroxidase (Southern Biotechnology Associates, Birmingham, Ala., USA) and substrate (5-aminosalicyclic acid, Sigma). Plates were read at 492 nm. Titers were expressed as mean±SD dilution, which gives the half-maximal value.

IL-6 Assays

Levels of IL-6 were determined by commercial ELISA (R&D systems, Minneapolis, Minn., USA). IL-6 bioactivity was determined by a proliferative assay using B9 cells. Briefly, $5\times10^3$ B9-cells in 200 µl 5% FCS-RPMI 1640 medium per well were plated in a round-bottom microtitre plate and incubated for 3 days using human recombinant IL-6 (R&D systems, Minneapolis, Minn., USA) as standards. At the end of the incubation, 0.5 µCi of $^3$[H]thymidine (NEN-Dupont, Boston, Mass., USA) was added per well. Three hours later, cells were harvested and thymidine incorporation was determined. Detection limit for the IL-6 bioassay was 1 pg/ml.

Statistical Analysis

Significance of differences was assessed by the Mann Whitney test using SigmaStat statistical analysis program and the GraphPad Prism program.

Results

A mouse experimental model, CIA (collagen induced arthritis), was used for assessing the effectiveness of IL-18BP as an agent for the treatment of arthritis. Administration of collagen and incomplete Freund's adjuvant in DBA/1 mice induces the development of an erosive, inflammatory arthritis and represents an ideal opportunity to explore the therapeutic potential of IL-18BP. To this end, endogenous IL-18 was neutralised using IL-18BP and the effect on various pathogenic parameters was evaluated.

A dose-related study was performed. Three groups of collagen-induced arthritic DBA/1 mice were treated therapeutically (i.e. after onset of disease) with 5 doses of IL-18BP i.p. (intraperitoneal). IL-18BP at concentrations of 10, 3, 1, 0.5 or 0.25 mg/kg was administered at the first clinical sign of disease. Injection of physiological saline (sodium chloride, NaCl) was used as a control. In addition to this, 10 000 IU of interferon β (IFN-β) were administered i.p. to assess the effect of IFN in this experimental model of arthritis. The effect on disease severity was monitored by daily visual scoring of each individual paw as described above. The mice were sacrificed at day 8 post-onset.

The following values were measured:
visual clinical scores (0-3.5 per paw) (FIG. 11A and B)
joint swelling/edema (in mm, measured with calipers) of first diseased paw, provided it was a hind paw (FIG. 12)
number of paws recruited into the disease (FIG. 13)
erosion scores of first diseased paw (0-4 cartilage destruction, FIG. 14).
Histopathological analysis of the paw that first developed arthritis (FIG. 15)
Levels of anti-collagen type 11 antibodies (FIG. 16)
Levels of IL-6 (FIG. 17).

Clinical Severity of Disease

As shown in FIGS. 11 A and B, the clinical severity of disease was significantly diminished in the groups treated with 1 mg/ml (P<0.01) and 0.5 mg/ml (0.01<P<0.05) of rhIL-18BP. Mice receiving the low dose of rhIL-18BP (0.25 mg/kg) or the high dose of 10 mg/kg had a clinical score similar to the placebo group. The dose of 1 mg/kg of IL-18BP was approximately as effective as Interferon β (designated IFNb in FIG. 11A).

Joint Inflammation and Paw Swelling (Edema)

Figure 12A:
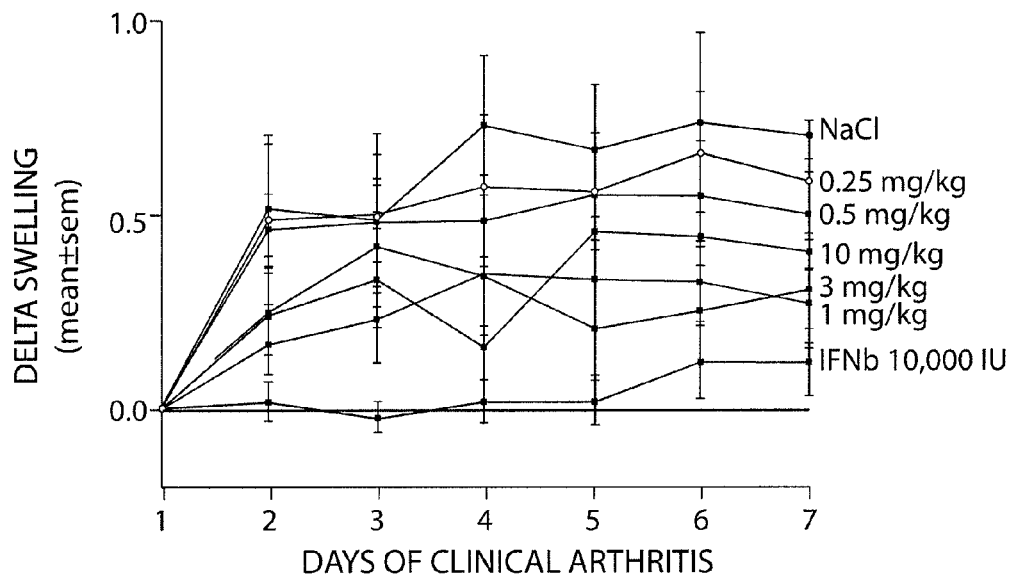
Figure 12B:
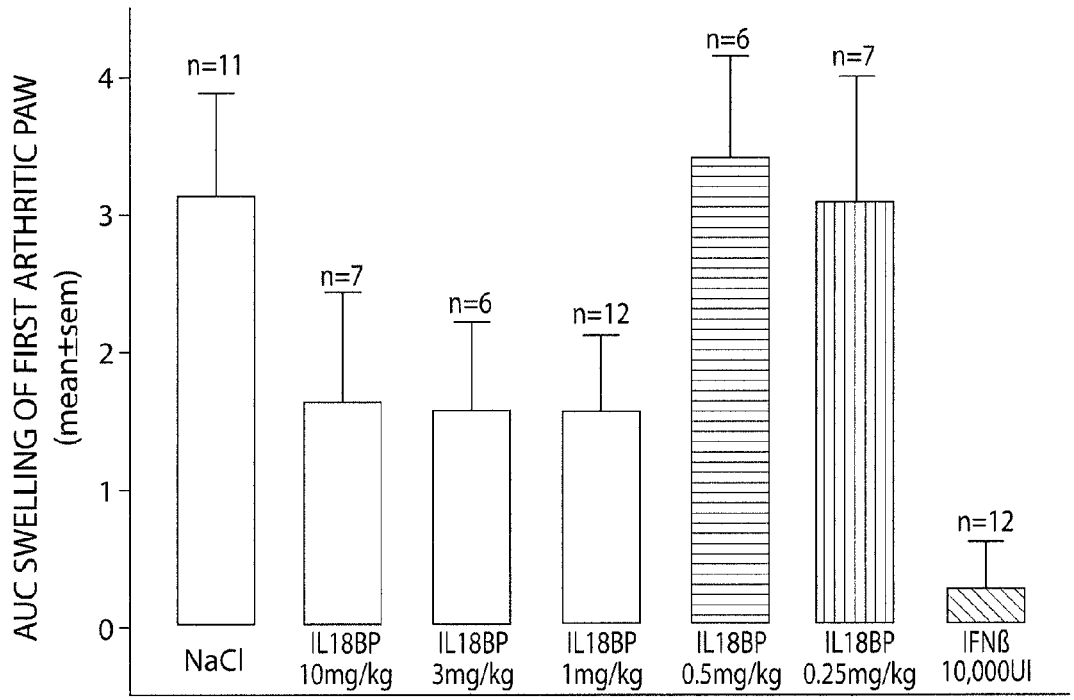

Macroscopical inflammation (swelling) was studied by measuring paw edema from day 1 after onset of disease until day 8, the end of the experiment. The results are shown in FIGS. 12 A and B. The effective doses of IL-18BP were 1, 3 and 10 mg/kg. Administration of lower doses did not result in a beneficial effect on the swelling of paws. As shown in FIGS. 12A and 12B, Interferon-β (IFNb) at a concentration of 10 000 IU showed a beneficial effect on paw swelling.

Microscopioc synovitis was examined at the end of the experiment on histopathological sections and was expressed as scores ("synovitis score"). The results of inflammation (swelling) and synovitis score are summarised in Table 1. Whilst treatment with rhIL-18BP at dosages 1 and 3 mg/kg resulted in a trend towards reduction of swelling, treatment with any dosage of IL-18BP had only a limited effect on the inflammatory synovitis (Table 1).

TABLE 1

EFFECT OF IL-18BP TREATMENT ON JOINT INFLAMMATION

| Treatment | | Swelling (AUC, mean ± sem) | Synovitis score (mean ± sem) |
|---|---|---|---|
| RhIL-18BP-6his | 3 mg/kg | 1.55 ± 0.64 | 2.17 ± 0.5 |
| | 1 mg/kg | 1.53 ± 0.60 | 1.98 ± 0.4 |
| | 0.5 mg/kg | 3.38 ± 0.70 | 1.92 ± 0.5 |
| | 0.25 mg/kg | 3.06 ± 0.90 | 2.08 ± 0.5 |
| Placebo | | 3.11 ± 0.77 | 2.23 ± 0.3 |

FIG. 13 shows that the number of paws affected by the disease was diminished after administration of IL-18BP. In particular, therapeutic injections of IL-18BP at doses of 1 and 0.5 mg/kg reduced the number of paws recruited into the disease, demonstrating that blockade of IL-18 in vivo halts the spreading of arthritis to additional joints. Treatment with 1 and 0,5 mg/kg of IL-18BP even appears capable to reverting some of the arthritic joints to normality.

Protection from Joint Destruction

Treatment of mice with rhIL-18BP resulted in protection of joints from destruction (FIG. 14). A semi-quantitative scoring system demonstrated that bone erosion showed a dose-related protective effect that was significant at 10 and 3 mg/kg ($P<0.05$, FIG. 14). Mice receiving 1 mg/kg of rhIL-18BP presented less erosion than mice receiving vehicle only. No protection was observed at doses of 0.5 mg/kg and 0.25 mg/kg. Interestingly, the effect on joint protection at doses of 3 and 10 mg/kg IL-18BP were comparable to or even more pronounced than the beneficial effect of 10 000 IU of Interferon β (IFN-β).

FIG. 15 shows the histology of a healthy (A) and a diseased (B) joint in comparison to a joint derived from an animal treated with IL-18BP (C). Sections were taken at the end of the experiment from those paws which first developed arthritis The joint from an arthritic mouse showed severe destructive arthritis with cartilage depletion and erosions and numerous infiltrating cells in the inflamed synovium. In the joint from a mouse treated with rhIL-18BP, the cartilage appeared almost normal despite the presence of inflammatory cells in the synovial space. There was not only a higher amount of cartilage, but the cartilage has also a smoother appearance.

Anti-IL-18 Treatment Modulates Levels of Anti-type II Collagen Antibodies

CIA mice have elevated levels of IgG1 and IgG2a anti-type II collagen antibodies in the circulation. Antibodies of the isotype IgG1 are associated to TH2 mediated diseases, whereas antibodies of the isotype IgG2a and IgG2b are associated to TH1 mediated diseases. Arthritis is usually classified as a TH1 mediated disease.

Anti-type II collagen (CII) IgG1 and IgG2a antibody isotypes were determined in the sera of animals that were treated with IL-18BP (FIG. 16). Levels of anti-CII of the IgG isotypes IgG1 and IgG2a were not significantly modified by IL-18BP treatment at day 4 or 8 (D4, D8) of clinical disease. However, a 2.6 and 3.4 fold decrease in collagen-specific IgG1/IgG2a ratios was observed after 8 days of rhIL-18BP-treatment, at 1 and 3 mg/kg respectively. SEQ ID NO:5 and SEQ ID NO:6 shows the experiment in which 3 mg/kg were used. Essentially the same results were obtained using an amount of 1 mg/kg of IL-18BP. The reduced IgG1/IgG2a ratio of anti-CII antibodies indicate a diminished concentration of anti-type 11 collagen antibodies of the isotype IgG2a and an elevated concentration of anti-type II collagen antibodies of the isotype IgG1, suggesting that there is an shift towards TH2-mediated disease in this model of arthritis.

Reduction of IL-6 Levels after IL-18 Neutralisation

To gain some insight into the effects of IL-18 blockade, IL-6 was measured in the sera of IL-18BP treated animals. FIG. 17 shows that the levels of bioactive IL-6 was significantly reduced in the animals having received IL-18BP treatment at all doses measured, i.e. at 1, 3 and 10 mg/kg as well as with Interferonβ (IFNβ). Immunoactive levels of IL-6 measured in the sera of the animals treated with 3 mg/kg rhIL-18BP were significantly reduced ($P<0.0023$) as compared with saline-treated animals. IL-6 serum levels of diseased animals treated with 1, 3 or 10 mg of IL-18BP or 10 000 IU of IFN-β were similar to normal mouse serum (NMS) derived from healthy animals, i.e. from those animals not having an inflammatory disease.

These findings demonstrate that IL-18 controls IL-6 levels during the onset of the disease. Since IL-6 is a marker of inflammation, these findings show that treatment of diseased mice with IL-18BP reduces inflammation in the animal.

From the experiments outlined above, the following conclusions can be drawn:

Administration of IL-18BP decreases the clinical severity of arthritis

IL-18BP inhibits further progression or spreading of the disease

Administration of IL-18BP decreases oedema

Administration of IL-18BP decreases cartilage destruction

Serum IL-6 levels are diminished and IgG1/IgG2a anti-CII ratios decreased after IL-18BP therapy.

The data presented above indicate that neutralisation of IL-18 bioactivity after disease onset represents a disease-modifying anti-rheumatic therapy. The results clearly demonstrate that IL18 blockade reduces the clinical progression of arthritis and more importantly stops progression of cartilage and bone destruction. IL18 blockade by IL-18BP, anti-IL-18 antibodies or by any other IL-18 blocking agent therefore represents a new disease-modifying anti-rheumatic therapy.

The foregoing description of the specific embodiments reveal the general nature of the invention so that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation.

REFERENCES

1. Afford, S. C., et al., Distinct patterns of chemokine expression are associated with leukocyte recruitment in alcoholic hepatitis and alcoholic cirrhosis. J Pathol, 1998. 186(1): p. 82-9.
2. Anderson, D. M., et al., A homologue of the TNF receptor and its ligand enhance T-cell growth and dendritic-cell function. Nature, 1997. 390(6656): p. 175-179.
3. Baroni, G. S., et al., Hepatic stellate cell activation and liver fibrosis are associated with necroinflammatory injury and Th1-like response in chronic hepatitis C. Liver, 1999. 19(3): p. 212-9.
4. Bird, G. L., et al., Increased plasma tumor necrosis factor in severe alcoholic hepatitis. Ann Intern Med, 1990. 112(12): p. 917-20.
5. Bollon, D. P., et al. (1980) J. Clin. Hematol. Oncol. 10:39-48.
6. Botstein, D., et al. (1982) Miami Wint. Symp. 19:265-274.
7. Broach, J. R., in "The Molecular Biology of the Yeast Saccharomyces: Life Cycle and Inheritance", Cold Spring Harbor Laboratory, Cold Spring Harbor, N.Y., pp. 445-470 (1981).
8. Broach, J. R., (1982) Cell 28:203-204.
9. Byrn R. A. et al., 1990, Nature (London) 344:667-670.
10. Car, B. D., V. M. Eng, B. Schnyder, L. Ozmen, S. Huang, P. Gallay, D. Heumann, M. Aguet, and B. Ryffel. 1994. Interferon gamma receptor deficient mice are resistant to endotoxic shock. J. Exp. Med. 179:1437-44 issn: 0022-1007.
11. Chater, K. F. et al., in "Sixth International Symposium on Actinomycetales Biology", Akademiai Kaido, Budapest, Hungary (1986), pp. 45-54).
12. Conti, B., J. W. Jahng, C. Tinti, J. H. Son, and T. H. Joh. 1997. Induction of interferon-gamma inducing factor in the adrenal cortex. J. Biol. Chem. 272:2035-2037.
13. Dao, T., K. Ohashi, T. Kayano, M. Kurimoto, and H. Okamura. 1996. Interferon-gamma-inducing factor, a novel cytokine, enhances Fas ligand-mediated cytotoxicity of murine T helper 1 cells. Cell-Immunol. 173:230-5 issn: 0008-8749.
14. Dayer, J-M (1999). J. Cin. Inv. 104, 1337-1339
15. DiDonato, J A, Hayakawa, M, Rothwarf, D M, Zandi, E and Karin, M. (1997), Nature 388, 16514-16517.
16. Elliott, M. J., Maini, R. N., Feldmann, M., Long-Fox, A., Charles, P., Bijl, H., and Woody, J. N., 1994, Lancet 344, 1125-1127.
17. Engelmann, H., D. Aderka, M. Rubinstein, D. Rotman, and D. Wallach. 1989. A tumor necrosis factor-binding protein purified to homogeneity from human urine protects cells from tumor necrosis factor toxicity. J. Biol. Chem. 264:11974-11980.
18. Engelmann, H., D. Novick, and D. Wallach. 1990. Two tumor necrosis factor-binding proteins purified from human urine. Evidence for immunological cross-reactivity with cell surface tumor necrosis factor receptors. J. Biol. Chem. 265:1531-1536.
19. Fantuzzi, G., et al., IL-18 regulation of IFN-g production and cell proliferation as revealed in interleukin-1b converting enzyme-deficient mice. Blood, 1998. 91: p. 2118-2125.
20. Fiore, G., et al., Liver tissue expression of CD80 and CD95 antigens in chronic hepatitis C: relationship with biological and histological disease activities. Microbios, 1999. 97(386): p. 29-38
21. Galle, P. R., et al., Involvement of the CD95 (APO-1/Fas) receptor and ligand in liver damage. J Exp Med, 1995. 182(5): p. 1223-30.
22. Gracie, A J, Forsey, R J, Chan, W L, Gilmour, A, Leung, B P, Greer, A R, Kennedy, K, Carter, R, Wei, X-Q, Xu, D., Field, M, Foulis, A, Liew, F Y, and McInnes, I B.(1999). J. Clin. Inv. 104: 1393-1401
23. Grantham (1974), Science, 185. 862-864.
24. Grove, J., et al., Association of a tumor necrosis factor promoter polymorphism with susceptibility to alcoholic steatohepatitis [see comments]. Hepatology, 1997. 26(1): p. 143-6.
25. Gryczan, T., "The Molecular Biology of the Bacilli", Academic Press, NY (1982), pp. 307-329).
26. Gutkind, J. S., et al., A novel c-fgr exon utilized in Epstein-Barr virus-infected B lymphcytes but not in mormal monocytes. Molec. Cell. Biol., 1991. 11: p.1500-1507.
27. Harada, K., et al., In situ nucleic acid hybridization of cytokines in primary biliary cirrhosis: predominance of the Th1 subset. Hepatology, 1997. 25(4): p. 791-6.
28. Heremans, H., J. Van Damme, C. Dillen, R. Dijkmans, and A. Billiau. 1990. Interferon gamma, a mediator of lethal lipopolysaccharide-induced Shwartzman-like shock reactions in mice. J. Exp. Med. 171:1853-69 issn: 0022-1007.
29. Hill, D. B., et al., Increased plasma interleukin-6 concentrations in alcoholic hepatitis. J Lab Clin Med, 1992. 119 (5): p. 547-52.
30. Hill, D. B., L. S. Marsano, and C. J. McClain, Increased plasma interleukin-8 concentrations in alcoholic hepatitis. Hepatology, 1993.18: p. 576-580.
31. Hiramatsu, N., et al., Immunohistochemical detection of Fas antigen in liver tissue of patients with chronic hepatitis C. Hepatology, 1994. 19(6): p. 1354-9.
32. Huang, Y. S., et al., Serum levels of interleukin-8 in alcoholic liver disease: relationship with disease stage, biochemical parameters and survival. J Hepatol, 1996. 24(4): p. 377-84.
33. Iio, S., et al., Serum levels of soluble Fas antigen in chronic hepatitis C patients. J Hepatol, 1998. 29(4): p. 517-23.
34. Izaki, K. (1978) Jpn. J. Bacteriol. 33:729-742).
35. John, J. F., et al. (1986) Rev. Infect. Dis. 8:693-704).
36. Kahiwamura, S., Okamura, H. (1998), Nippon. Rinsho. 56, pp. 1798-1806.
37. Kendall, K. J. et al. (1987) J. Bacteriol. 169:4177-4183).
38. Kim SH, Eisenstein M, Reznikov L, Fantuzzi G, Novick D, Rubinstein M, Dinarello Calif. Structural requirements of six naturally occurring isoforms of the IL-18 binding protein to inhibit IL-18. Proc Natl Acad Sci USA 2000;97: 1190-1195.
39. Knight D M, Trinh H, Le J, Siegel S, Shealy D, McDonough M, Scallon B, Moore M A, Vilcek J, Daddona P, et al. Construction and initial characterization of a mouse-human chimeric anti-TNF antibody.Mol Immunol 1993 Nov 30:16 1443-53
40. Kohno, K., J. Kataoka, T. Ohtsuki, Y. Suemoto, I. Okamoto, M. Usui, M. Ikeda, and M. Kurimoto. 1997. IFN-gamma-inducing factor (IGIF) is a costimulatory factor on the activation of Th1 but not Th2 cells and exerts its effect independently of IL-12. J. Immunol. 158:1541-1550.
41. Lee, M., et al., Expression of Th1 and Th2 type cytokines responding to HBsAg and HBxAg in chronic hepatitis B patients. J Korean Med Sci, 1999. 14(2): p. 175-81.

42. Lukkari, T. A., et al., Short-term ethanol exposure increases the expression of Kupffer cell CD14 receptor and lipopolysaccharide binding protein in rat liver. Alcohol Alcohol, 1999. 34(3): p. 311-9.

43. Luo, K. X., et al., In situ investigation of Fas/FasL expression in chronic hepatitis B infection and related liver diseases. J Viral Hepat, 1997. 4(5): p. 303-7.

44. Maliszewski, C. R., T. A. Sato, T. Vanden Bos, S. Waugh, S. K. Dower, J. Slack, M. P. Beckmann, and K. H. Grabstein. 1990. Cytokine receptors and B cell functions. I. Recombinant soluble receptors specifically inhibit IL-1- and IL-4-induced B cell activities in vitro. J. Immunol. 144:3028-3033.

45. Maniatis, T., in "Cell Biology: A Comprehensive Treatise, Vol. 3: Gene Expression", Academic Press, NY, pp. 563-608 (1980).

46. Maniatis et al., Molecular Cloning: A Laboratory Manual, Cold Spring Harbor Laboratory, New York, 1982.

47. Martinez, F., et al., Ethanol and cytokine secretion. Alcohol, 1992. 9(6): p. 455-8.

48. McClain, C. J., et al., Tumor necrosis factor and alcoholic liver disease. Alcohol Clin Exp Res, 1998. 22(5 Suppl): p. 248S-252S.

49. McClain, C. J. and D. A. Cohen, Increased tumor necrosis factor production by monocytes in alcoholic hepatitis. Hepatology, 1989. 9(3): p. 349-51.

50. Micallef, M. J., T. Ohtsuki, K. Kohno, F. Tanabe, S. Ushio, M. Namba, T. Tanimoto, K. Torigoe, M. Fujii, M. Ikeda, S. Fukuda, and M. Kurimoto. 1996. Interferon-gamma-inducing factor enhances T helper 1 cytokine production by stimulated human T cells: synergism with interleukin-12 for interferon-gamma production. Eur-J-Immunol 26:1647-51 issn: 0014-2980.

51. Mizushima, S. and Nagata, S. (1990) pEF-BOS, a powerful mammalian expression vector. Nucleic Acid Res. 18:5322-5328.

52. Nanji, A. A., et al., Activation of nuclear factor κ B and cytokine imbalance in experimental alcoholic liver disease in the rat. Hepatology, 1999. 30(4): p. 934-43.

53. Nakamura, K., H. Okamura, K. Nagata, T. Komatsu, and T. Tamura. 1993. Purification of a factor which provides a costimulatory signal for gamma interferon production. Infect-Immun 61:64-70 issn: 0019-9567.

54. Nakamura, K., H. Okamura, M. Wada, K. Nagata, and T. Tamura. 1989. Endotoxin-induced serum factor that stimulates gamma interferon production. Infect-Immun 57:590-5 issn: 0019-9567.

55. Nishimura, T. and A. Ohta, A critical role for antigen-specific Th1 cells in acute liver injury in mice. J. Immunol, 1999. 162: p. 6503-6509.

56. Novick, D., B. Cohen, and M. Rubinstein. 1994. The Human Interferon alpha/beta Receptor—Characterization and Molecular Cloning. Cell 77:391-400.

57. Novick, D., B. Cohen, and M. Rubinstein. 1992. Soluble Interferon-alpha Receptor Molecules Are Present in Body Fluids. FEBS Lett 314:445-448.

58. Novick, D., H. Engelmann, D. Wallach, and M. Rubinstein. 1989. Soluble cytokine receptors are present in normal human urine. J. Exp. Med. 170:1409-1414.

59. Novick, D, Kim, S-H, Fantuzzi, G, Reznikov, L, Dinarello, C, and Rubinstein, M (1999). Immunity 10, 127-136.

60. Ohlinger, W., et al., Immunohistochemical detection of tumor necrosis factor-α, other cytokines and adhesion molecules in human livers with alcoholic hepatitis. Virchows Arch A Pathol Anat Histopathol, 1993. 423(3): p. 169-76.

61. Okamura, H., H. Tsutsui, T. Komatsu, M. Yutsudo, A. Hakura, T. Tanimoto, K. Torigoe, T. Okura, Y. Nukada, K. Hattori, K. Akita, M. Namba, F. Tanabe, K. Konishi, S. Fukuda, and M. Kurimoto. 1995. Cloning of a new cytokine that induces IFN-gamma production by T cells. Nature 378:88-91.

62. Okamoto, T., et al., Induction of Fas ligand and Fas antigen mRNA expressions in interferon-γ transgenic mouse liver. Jpn J Pharmacol, 1998. 78(2): p. 233-5.

63. Okazaki, M., et al., Hepatic Fas antigen expression before and after interferon therapy in patients with chronic hepatitis C. Dig Dis Sci, 1996. 41(12): p. 2453-8.

64. Okamoto, T., K. Yamamura, and 0. Hino, The mouse interferon-γ transgene chronic hepatitis model (Review). Int J Mol Med, 1999. 3(5): p. 517-20.

65. Olee T, Hashimoto S, Quach J, Lotz M. (1999). J Immunol 162:2 1096-100

66. Parnet, P, Garka, K E, Bonnert, T P, Dower, S K, and Sims, J E. (1996), J. Biol. Chem. 271, 3967-3970.

67. Plater-Zyberk C, Bonnefoy J Y. Marked amelioration of established collagen-induced arthritis by treatment with antibodies to CD23 in vivo. Nat Med 1995;1 :781-785.

68. Saha N, Moldovan F, Tardif G, Pelletier J P, Cloutier J M, Martel-Pelletier J.(1999). Arthritis Rheum 42:8 1577-87.

69. Rothe, H., N. A. Jenkins, N. G. Copeland, and H. Kolb. 1997. Active stage of autoimmune diabetes is associated with the expression of a novel cytokine, IGIF, which is located near Idd2. J-Clin-lnves.t 99:469-74 issn: 0021-9738.

70. Sambrook, J., E. F. Fritsch, and M. T., Molecular Cloning: A laboratory manual. 2nd ed. ed. 1989, Cold Spring Harbor, New York: Cold Spring Harbor Laboratory.

71. Simonet, W. S., et al., Osteoprotegerin: a novel secreted protein involved in the regulation of bone density. Cell, 1997. 89(2): p. 309-319.

72. Sheron, N., et al., Elevated plasma interleukin-6 and increased severity and mortality in alcoholic hepatitis. Clin Exp Immunol, 1991. 84(3): p. 449-53.

73. Sompayrac, L. H. and K. L. Danna, Efficient infection of monkey cells with DNA of simian virus 40. Proc. Nat'l. Acad. Sci. USA, 1981. 78: p. 7575-7578.

74. Sparks, C. A., et al., Assignment of the nuclear mitotic apparatus protein NuMA gene to human chromosome 11q13. Genomics, 1993.17: p. 222-224.

75. Su, G. L., et al., CD14 and lipopolysaccharide binding protein expression in a rat model of alcoholic liver disease. Am J Pathol, 1998.152(3): p. 841-9.

76. Taieb, J., et al., Raised plasma soluble Fas and Fas-ligand in alcoholic liver disease [letter]. Lancet, 1998. 351(9120): p. 1930-1.

77. Triantaphyllopoulos, K A, Williams, R, Tailor, H, and Chernakovsky, Y (1999). Arthritis and Rheumatism 42, 90-99.

78. Tsutsui, H., K. Nakanishi, K. Matsui, K. Higashino, H. Okamura, Y. Miyazawa, and K. Kaneda. 1996. IFN-gamma-inducing factor up-regulates Fas ligand-mediated cytotoxic activity of murine natural killer cell clones. J. Immunol. 157:3967-73 issn: 0022-1767.

79. Tsuij, H., Mukaida, N., Harada A., Kaneko, S., Matsushita, E., Nakanuma, Y., Tsutsui, H., Okamura, H., Nakanishi, K., Tagawa,m Y, Iwakura, Y., Kobayashi, K., and Matsuschima, K.(1999), J. Immunol. 162, pp.1049-1055.

80. Tucci, A., James, H., Chicheportiche, R., Bonnefoy, J. Y., Dayer, J. M., and Zubler, R. H., 1992, J.Immunol. 148, 2778-2784.
81. Ushio, S., M. Namba, T. Okura, K. Hattori, Y. Nukada, K. Akita, F. Tanabe, K. Konishi, M. Micallef, M. Fujii, K. Torigoe, T. Tanimoto, S. Fukuda, M. Ikeda, H. Okamura, and M. Kurimoto. 1996. Cloning of the cDNA for human IFN-gamma-inducing factor, expression in *Escherichia coli*, and studies on the biologic activities of the protein. J. Immunol. 156:4274-4279.34. Okayama, H. and Berg, P. (1983) A cDNA cloning vector that permits expression of cDNA inserts in mammalian cells. Mol. Cell. Biol. 3:280-289.
82. Williams R O, Mason L J, Feldmann M, Maini R N. Synergy between anti-CD4 and anti-tumor necrosis factor in the amelioration of established collagen-induced arthritis. Proc Natl Acad Sci USA 1994 Mar. 29 91:7 2762-6.
83. Yasuda, H., et al., Identity of osteoclastogenesis inhibitory factor (OCIF) and osteoprotegerin (OPG): a mechanism by which OPG/OCIF inhibits osteoclastogenesis in vitro. Endocrinology, 1998. 139: p. 1329-1337.
84. Yoshimoto T, Takeda, K, Tanaka, T, Ohkusu, K, Kashiwamura, S, Okamura, H, Akira, S and Nakanishi, K (1998), J. Immunol. 161, 3400-3407.

We claim:

1. A method of treating a disease associated with an excess of IL-18, said method comprising administering to a subject in which such treatment is desired, a composition comprising:
   (a) a polypeptide comprising an amino acid sequence selected from the group consisting of AA1-AA197 of SEQ ID NO:6 and AA29-AA197 of SEQ ID NO:6
   (b) a mutein of any one of the sequences in (a), characterized in that the mutein
      i) has at least 90% identity to at least one of the sequences in (a);
      ii) comprises the amino acid sequence of SEQ ID NO: 10; and
      iii) binds IL-18
   in an amount sufficient to treat said disease in said subject.

2. The method of claim 1, wherein said disease associated with an excess of IL-18 is selected from the group consisting of autoimmune diseases, Type I diabetes, rheumatoid arthritis, graft rejections, inflammatory bowel disease, sepsis, multiple sclerosis, ischemic heart disease, ischemic brain injury, chronic hepatitis, acute hepatitis, psoriasis, chronic pancreatitis, and acute pancreatitis.

3. The method of claim 2 wherein the disease is rheumatoid arthritis.

4. The method according to any one of claims 1-3, wherein said subject is a human.

5. The method of claim 1, wherein the polypeptide is glycosylated at one or more sites.

6. The method of claim 1, wherein the polypeptide is not glycosylated.

7. The method of claim 1, wherein the polypeptide further comprises at least one moiety attached to one or more functional groups which occur as one or more side chains on the amino acid residues or the N- or C-terminal groups.

8. The method of claim 7, wherein said at least one moiety is a polyethylene glycol moiety.

9. The method of claim 1, wherein the polypeptide is circularly permutated.

10. The method of claim 1, wherein the polypeptide is a non-viral protein.

11. The method of claim 1, wherein the polypeptide is a human protein.

12. The method of claim 1, wherein the polypeptide is a fused protein.

13. The method of claim 1, wherein the polypeptide comprises an Ig fusion.

14. The method of claim 1, wherein the polypeptide is soluble.

15. The method of claim 1, wherein the polypeptide is pegylated.

* * * * *

UNITED STATES PATENT AND TRADEMARK OFFICE
CERTIFICATE OF CORRECTION

PATENT NO. : 7,696,154 B2 Page 1 of 1
APPLICATION NO. : 11/724737
DATED : April 13, 2010
INVENTOR(S) : Daniela Novick et al.

It is certified that error appears in the above-identified patent and that said Letters Patent is hereby corrected as shown below:

Claim 2, col. 81, line 4, grafi should read graft.

Signed and Sealed this

Twenty-fifth Day of May, 2010

David J. Kappos
*Director of the United States Patent and Trademark Office*